US012653738B2

(12) United States Patent
Harrison et al.

(10) Patent No.: US 12,653,738 B2
(45) Date of Patent: Jun. 16, 2026

(54) MEDICAL TRANSPORTER APPARATUS AND METHODS WITH SMART SYSTEM

(71) Applicant: SYNAPTIVE MEDICAL INC., Toronto (CA)

(72) Inventors: Daniel Gavin Harrison, Toronto (CA); William Wai-Leung Lau, Toronto (CA); Murtasim Syed, Toronto (CA); Fiona Khor, Toronto (CA)

(73) Assignee: SYNAPTIVE MEDICAL INC.

( * ) Notice: Subject to any disclaimer, the term of this patent is extended or adjusted under 35 U.S.C. 154(b) by 45 days.

(21) Appl. No.: 18/637,909

(22) Filed: Apr. 17, 2024

(65) Prior Publication Data

US 2024/0342027 A1     Oct. 17, 2024

Related U.S. Application Data

(60) Provisional application No. 63/496,430, filed on Apr. 17, 2023.

(51) Int. Cl.
    *A61G 7/018*        (2006.01)
    *A61B 5/055*        (2006.01)
    (Continued)

(52) U.S. Cl.
    CPC .............. *A61G 7/018* (2013.01); *A61B 5/055* (2013.01); *A61G 7/012* (2013.01); *A61G 7/0508* (2016.11); *A61G 7/0527* (2016.11); *A61G 7/08* (2013.01); *A61G 2210/30* (2013.01); *A61G 2210/50* (2013.01)

(58) Field of Classification Search
    CPC ...... A61G 7/018; A61G 7/012; A61G 7/0508; A61G 7/0527; A61G 7/08; A61G 2210/30; A61G 2210/50; A61G 2203/44; A61G 1/02; A61G 13/06; A61B 5/055; A61B 5/704; A61B 6/0407
    See application file for complete search history.

(56) References Cited

U.S. PATENT DOCUMENTS 4,287,422 A * 9/1981 Kuphal ................ A61B 6/0407
                                                        5/601
2010/0031443 A1 2/2010 Georgiev et al.
                    (Continued)

FOREIGN PATENT DOCUMENTS

JP        2013106676        6/2013

OTHER PUBLICATIONS

Search report issued by the Intellectual Property Office of the UK in relation to GB Application No. GB2405419.9 dated Sep. 8, 2021, 2 pgs.

*Primary Examiner* — Jonathan Liu

(57) ABSTRACT

A medical transporter apparatus and methods, involving: a frame; at least one side-rail operably coupled with the frame; at least one lift member operably coupled with the frame; at least one actuator operably coupled with the at least one lift member, the at least one actuator configured to adjust an elevation of the frame by actuating the at least one lift member; a docking mechanism operable with the frame for facilitating docking of the frame in relation to an imaging apparatus; and a weighing mechanism, the weighing mechanism being at least one of operably coupled with the frame and integrated with the frame, whereby a patient is weighable, and whereby elevation of the frame is electronically adjustable.

13 Claims, 60 Drawing Sheets

(51) Int. Cl.
| | |
|---|---|
| *A61G 7/012* | (2006.01) |
| *A61G 7/05* | (2006.01) |
| *A61G 7/08* | (2006.01) |

(56) References Cited

U.S. PATENT DOCUMENTS

| | | | |
|---|---|---|---|
| 2011/0030142 A1* | 2/2011 | Karwal | A61G 7/0507 |
| | | | 5/608 |
| 2014/0296692 A1 | 10/2014 | Iizuka et al. | |
| 2018/0289575 A1 | 10/2018 | Hiratsuka et al. | |
| 2020/0155402 A1 | 5/2020 | Luybanksy | |
| 2020/0405178 A1 | 12/2020 | Shi et al. | |
| 2021/0196533 A1* | 7/2021 | Derenne | A61G 1/0268 |
| 2022/0008016 A1* | 1/2022 | Harrison | A61G 3/001 |
| 2022/0226178 A1* | 7/2022 | Johnson | A61G 1/013 |

* cited by examiner

71

70

$E_2$

150

150

175

175

H

240

22          22

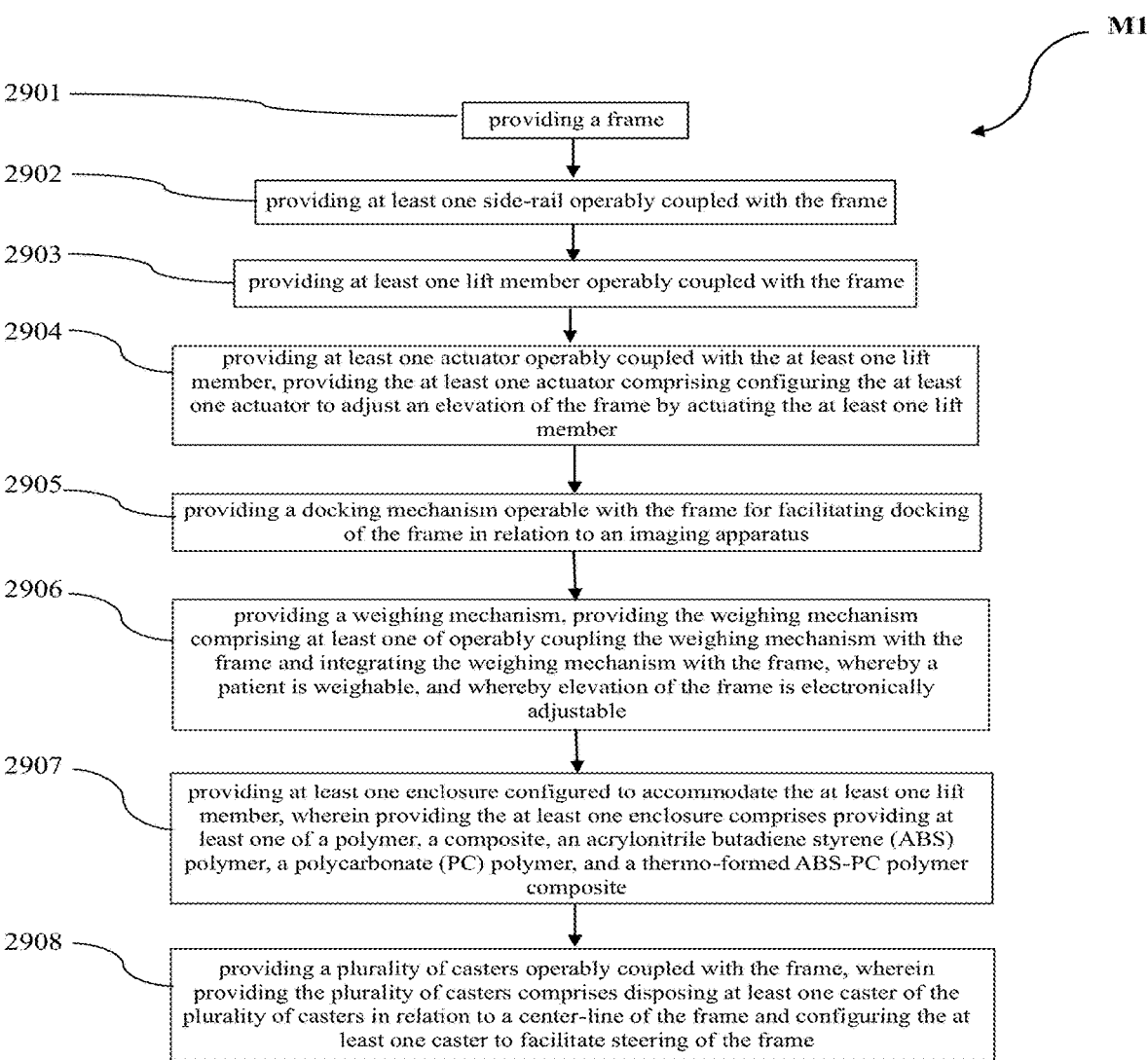

M1

2901 — providing a frame

2902 — providing at least one side-rail operably coupled with the frame

2903 — providing at least one lift member operably coupled with the frame

2904 — providing at least one actuator operably coupled with the at least one lift member, providing the at least one actuator comprising configuring the at least one actuator to adjust an elevation of the frame by actuating the at least one lift member 2905 — providing a docking mechanism operable with the frame for facilitating docking of the frame in relation to an imaging apparatus 2906 — providing a weighing mechanism, providing the weighing mechanism comprising at least one of operably coupling the weighing mechanism with the frame and integrating the weighing mechanism with the frame, whereby a patient is weighable, and whereby elevation of the frame is electronically adjustable 2907 — providing at least one enclosure configured to accommodate the at least one lift member, wherein providing the at least one enclosure comprises providing at least one of a polymer, a composite, an acrylonitrile butadiene styrene (ABS) polymer, a polycarbonate (PC) polymer, and a thermo-formed ABS-PC polymer composite 2908 — providing a plurality of casters operably coupled with the frame, wherein providing the plurality of casters comprises disposing at least one caster of the plurality of casters in relation to a center-line of the frame and configuring the at least one caster to facilitate steering of the frame

FIG. 29

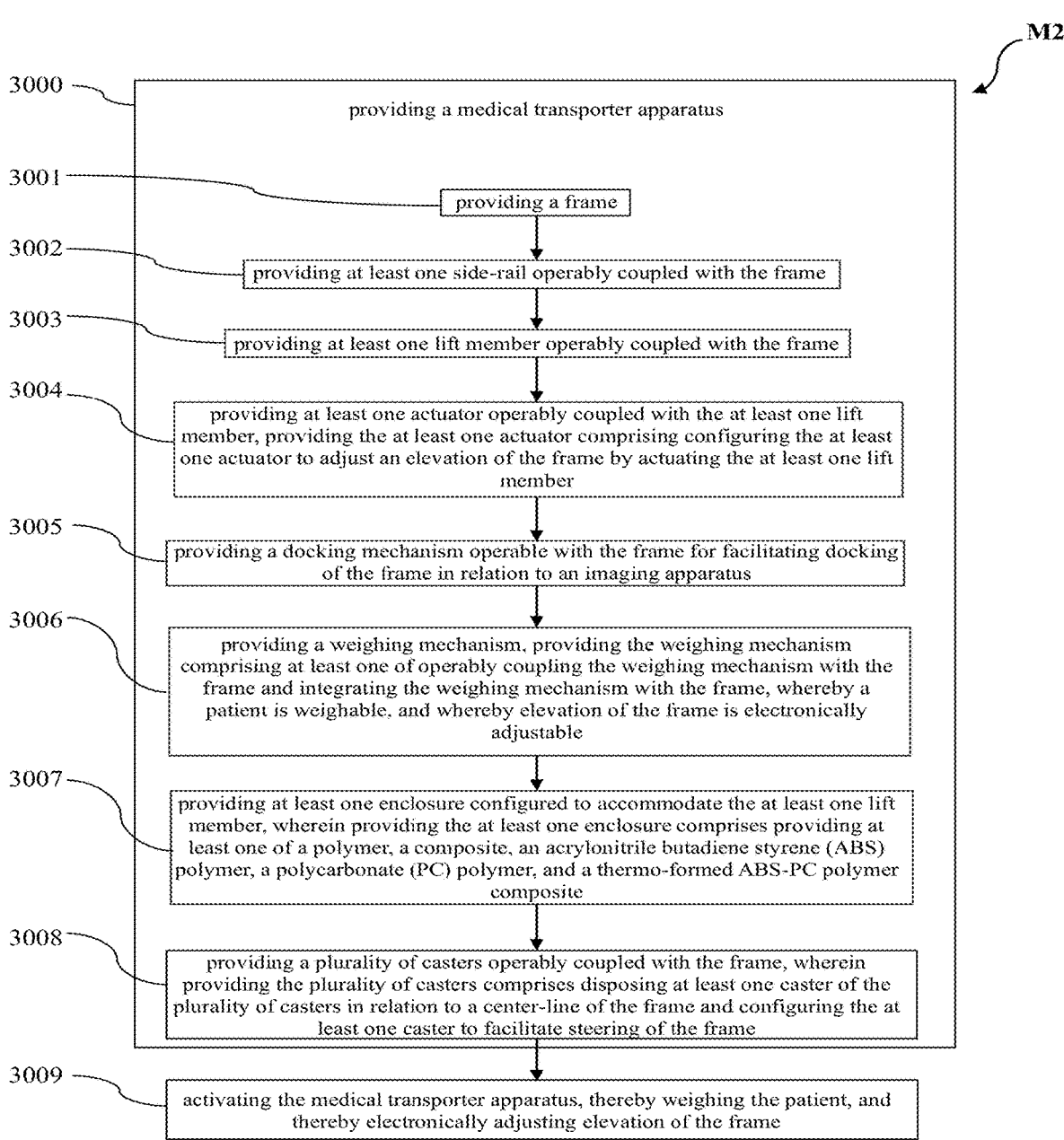

M2

3000 — providing a medical transporter apparatus

3001 — providing a frame

3002 — providing at least one side-rail operably coupled with the frame

3003 — providing at least one lift member operably coupled with the frame

3004 — providing at least one actuator operably coupled with the at least one lift member, providing the at least one actuator comprising configuring the at least one actuator to adjust an elevation of the frame by actuating the at least one lift member 3005 — providing a docking mechanism operable with the frame for facilitating docking of the frame in relation to an imaging apparatus 3006 — providing a weighing mechanism, providing the weighing mechanism comprising at least one of operably coupling the weighing mechanism with the frame and integrating the weighing mechanism with the frame, whereby a patient is weighable, and whereby elevation of the frame is electronically adjustable 3007 — providing at least one enclosure configured to accommodate the at least one lift member, wherein providing the at least one enclosure comprises providing at least one of a polymer, a composite, an acrylonitrile butadiene styrene (ABS) polymer, a polycarbonate (PC) polymer, and a thermo-formed ABS-PC polymer composite 3008 — providing a plurality of casters operably coupled with the frame, wherein providing the plurality of casters comprises disposing at least one caster of the plurality of casters in relation to a center-line of the frame and configuring the at least one caster to facilitate steering of the frame 3009 — activating the medical transporter apparatus, thereby weighing the patient, and thereby electronically adjusting elevation of the frame

FIG. 30

MEDICAL TRANSPORTER APPARATUS AND METHODS WITH SMART SYSTEM

CROSS REFERENCE TO RELATED APPLICATION(S)

The document is a Nonprovisional Patent Application claiming the benefit of, and priority to, U.S. Provisional Patent Application Ser. No. 63/496,430, entitled "PATIENT TRANSPORTER FOR MRI WITH INTEGRATED SCALE AND ELECTRONIC HEIGHT ADJUSTMENT," filed on Apr. 17, 2023, and all of which are hereby incorporated by reference in their entirety.

FIELD

Generally, the present disclosure relates to patient transport apparatuses and methods. More particularly, the present disclosure relates to patient transport apparatuses and methods for use with MRI machines. Even more particularly, the present disclosure relates to patient transport apparatuses and methods that are interfaceable with MRI machines.

BACKGROUND

In the related art, various patient transporters have been used for performing a variety of medical procedures. For example, a related art modular intervention bed has been used with a medical tomographic imaging system, the bed having an associated patient transport device and an imaging device. The modular intervention bed has a trestle configured to engage a patient transport device, with the trestle having an intervention area. A patient couch movably mounted on the trestle, with the patient couch defining an opening corresponding to the intervention area. The couch has a plurality of patient mats with each mat connected to at least one other mat, a pair of rollers mounted on each mat in a spaced apart relationship with each roller proximate to an outside edge of each mat. The modular intervention bed can be reconfigured by adding or removing a mat, thereby moving the intervention area and opening to correspond with the portion of a patient under investigation during an intervention procedure guided by a medical tomographic imaging system. However, this related art modular intervention bed merely uses rollers and does not have any features for safely interfacing and interlocking with the medical tomographic imaging system.

Another related art apparatus involves a patient support apparatus used with navigation and guidance systems and has control systems with one or more image, radar, and/or laser sensors to detect objects and determine if a likelihood of collision exists, wherein the control system controls the speed and steering of the patient support apparatus to reduce the likelihood of collision. The control system may be adapted to autonomously drive the patient support apparatus, to transmit a message to a remote device indicating whether it is occupied by a patient or not, and/or to transmit its route to the remote device. The remote device may determine an estimate of a time of arrival of the patient support apparatus at a particular destination and/or determine a distance of the patient support apparatus from the particular destination. However, this related art patient support apparatus does not have features for safely interfacing and interlocking with an MRI machine. Rather, this related art patient support apparatus uses materials that are incompatible with MRI and is configured for only patient transport within a hospital.

Yet another related art system involves a patient positioning system for use with an imaging system, wherein a palette for an imaging system is provided that includes a base portion movably connected to the imaging system and an extender portion removably connected to the base portion. The extender portion together with the base portion supports an object to be imaged by the imaging system. However, this related art patient positioning system also merely uses rollers and does not have any features for safely interfacing and interlocking with the imaging system.

Yet still another related art system involves a transport bed having a lifting mechanism, a bed body, and a table base, wherein the bed body and the table base are connected through the lifting mechanism. A controlling device is arranged on the base seat of the table base. At least two cross beams are arranged on the bed frame, the position corresponding with the cross beams of the backside of the bed board is provided with a smooth sliding face which is beneficial for the bed board to slide left and right along the cross beams. Two sides of the bed frame are movably provided with protecting boards used for fixing the bed board. When the bed board moves on the cross beams of the bed frame, due to the fact a friction factor is quite small, medical staff can move the bed board to medical equipment. The bed-frame has nonmagnetic materials. However, this related art transport bed also merely uses rollers and does not have any features for safely interfacing and interlocking with an imaging system.

Yet still another related art system involves a patient bed for use with an NMR imaging system. An expanded diagnostic NMR installation with operating functionality contains an NMR imaging apparatus with a patient bed for transporting a patient into an imaging volume of the NMR imaging apparatus. An operating column for receiving the patient bed is arranged next to the NMR imaging apparatus at a fixed distance therefrom along the longitudinal direction of motion of the patient bed. The operating column contains a swinging mechanism for rotating or pivoting the patient bed around a vertical axis. However, this related art transport bed merely docks with an operating column and does not have any features for safely interfacing and interlocking with an imaging system.

Therefore, a need exists in the related art, for a mechanical transport system that can move a patient from an intensive care unit (ICU) to a magnetic resonance imaging (MRI) machine without having to lift the patient from one surface to another surface, e.g., that eliminates a need for transferring patient from one type of medical bed to another type of medical bed, and that facilitates quickly scanning a patient.

SUMMARY

The present disclosure addresses at least many of the foregoing challenges experienced by related art. The subject matter of the present disclosure involves a medical transporter or transporter apparatus and methods that facilitate moving a patient from an intensive care unit (ICU) to a magnetic resonance imaging (MRI) machine without having to lift the patient from one surface to another surface, e.g., that eliminates a need for transferring patient from one type of medical bed to via a safer docking-and-undocking mechanism. The docking-and-undocking mechanism comprises: at least a five-way interlocking feature configured to quick-connect and quick disconnect in relation to an MRI machine and an MRI head coil; and a sensor system for safety detection.

In accordance with an embodiment of the present disclosure, a smart system for coupling a medical transporter with an imaging apparatus, comprises: a smart docking module comprising at least one coupler responsive to a controller operable by a set of executable instructions, the smart docking module comprising a non-magnetic material; and the smart docking module configured by the controller to automatically perform at least one of: position, dock, engage, latch, lock, interlock, release, emergency-release, quick-release, disengage, emergency-disengage, and quick-disengage the medical transporter in relation to the imaging apparatus.

In accordance with another embodiment of the present disclosure, a method of fabricating a smart system for coupling a medical transporter or transporter apparatus with an imaging apparatus, comprising: providing a smart docking module comprising providing at least one coupler responsive to a controller operable by a set of executable instructions, providing the smart docking module comprising providing a non-magnetic material; and providing the smart docking module comprising configuring the smart docking module, by the controller, to automatically perform at least one of: position, dock, engage, latch, lock, interlock, release, emergency-release, quick-release, disengage, emergency-disengage, and quick-disengage the medical transporter in relation to the imaging apparatus.

In accordance with another embodiment of the present disclosure, a method of coupling a medical transporter or transporter apparatus with an imaging apparatus by way of a smart system, comprising: providing the smart system, providing the smart system comprising: providing a smart docking module comprising providing at least one coupler responsive to a controller operable by a set of executable instructions, providing the smart docking module comprising providing a non-magnetic material; and providing the smart docking module comprising configuring the smart docking module, by the controller, to automatically perform at least one of: position, dock, engage, latch, lock, interlock, release, emergency-release, quick-release, disengage, emergency-disengage, and quick-disengage the medical transporter in relation to the imaging apparatus; and activating the smart system, thereby automatically docking the medical transporter with the imaging apparatus.

In accordance with another embodiment of the present disclosure, a medical transporter or transporter apparatus comprises: a frame; at least one side-rail operably coupled with the frame; at least one lift member operably coupled with the frame; at least one actuator operably coupled with the at least one lift member, the at least one actuator configured to adjust an elevation of the frame by actuating the at least one lift member; a docking mechanism operable with the frame for facilitating docking of the frame in relation to an imaging apparatus; and a weighing mechanism, the weighing mechanism being at least one of operably coupled with the frame and integrated with the frame, whereby a patient is weighable, and whereby elevation of the frame is electronically adjustable.

In accordance with another embodiment of the present disclosure, a method of fabricating a medical transporter or transporter apparatus comprises: providing a frame; providing at least one side-rail operably coupled with the frame; providing at least one lift member operably coupled with the frame; providing at least one actuator operably coupled with the at least one lift member, providing the at least one actuator comprising configuring the at least one actuator to adjust an elevation of the frame by actuating the at least one lift member; providing a docking mechanism operable with the frame for facilitating docking of the frame in relation to an imaging apparatus; and providing a weighing mechanism, providing the weighing mechanism comprising at least one of operably coupling the weighing mechanism with the frame and integrating the weighing mechanism with the frame, whereby a patient is weighable, and whereby elevation of the frame is electronically adjustable.

In accordance with another embodiment of the present disclosure, a method of weighing a patient and automatically adjusting elevation of a frame, by way of a medical transporter or transporter apparatus, comprises: providing a medical transporter, providing the medical transporter comprising: providing a frame; providing at least one side-rail operably coupled with the frame; providing at least one lift member operably coupled with the frame; providing at least one actuator operably coupled with the at least one lift member, providing the at least one actuator comprising configuring the at least one actuator to adjust an elevation of the frame by actuating the at least one lift member; providing a docking mechanism operable with the frame for facilitating docking of the frame in relation to an imaging apparatus; and providing a weighing mechanism, providing the weighing mechanism comprising at least one of operably coupling the weighing mechanism with the frame and integrating the weighing mechanism with the frame, thereby weighing a patient, and thereby elevation of the frame is electronically adjustable.

Some of the features in the present disclosure are broadly outlined in order that the section entitled Detailed Description is better understood and that the present contribution to the art may be better appreciated. Additional features of the present disclosure are described hereinafter. In this respect, understood is that the present disclosure is not limited in its application to the details of the components or steps set forth herein or as illustrated in the several figures of the being carried out in various ways. Also, understood is that the phraseology and terminology employed herein are for the purpose of the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

FIG. 29 is a flow diagram illustrating a method of fabricating a smart system for determining a patient's weight and automatically adjusting elevation of a medical transporter bed based on the patient's weight, in accordance with an embodiment of the present disclosure.

FIG. 30 is a flow diagram illustrating a method of determining a patient's weight and automatically adjusting elevation of a medical transporter bed based on the patient's weight by way of a smart system, in accordance with an embodiment of the present disclosure.

Figure 1A:
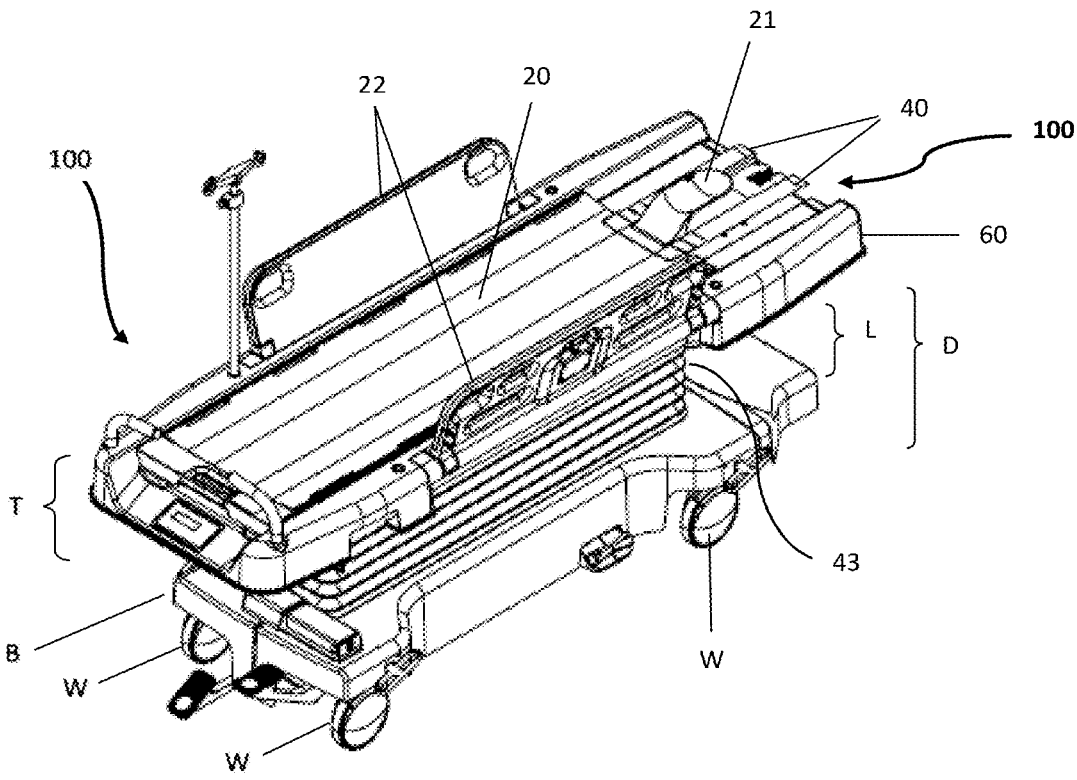
FIG. 1A is a diagram illustrating a perspective view of a medical transporter, such as an MRI transporter, adaptable for operation by a smart system, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

Referring to FIG. 1A, this diagram illustrates, in a perspective view, a medical transporter 100, such as an MRI transporter, adaptable for operation by a smart system, the smart system comprising a smart docking module D (FIG. 2A), in accordance with an embodiment of the present disclosure. Components of the smart system are disposable within at least one of a base B, a table T, and a lift portion L of the medical transporter 100. The smart system is configured to couple the medical transporter 100 with medical equipment, such as an imaging apparatus I, e.g., an MRI machine (FIG. 3), by way of a docking module D. The docking module D comprises a non-magnetic material and at least one coupler (not shown).

Still referring to FIG. 1A, the docking module D is responsive to a controller (not shown) operable by a set of executable instructions; and the docking module D is configured by a controller (not shown) to automatically perform at least one of: position, dock, engage, latch, lock, interlock, release, emergency-release, quick-release, disengage, emergency-disengage, and quick-disengage the medical transporter 100 in relation to medical equipment, such as the imaging apparatus I. In further embodiments, the docking module may be controlled by the user by actuating the foot pedals. In further embodiments, the controller comprises at least one of: a computer, a processor, a processing unit, a power source, a memory device, and a safety device. The at least one coupler comprises at least one latch. In further embodiments, the controller is disposed in relation to the smart system, either wired or wirelessly; and, alternatively, the controller is remotely disposed. Alternatively, the docking module is manually or mechanically operable in the absence of a controller. For example, the sensors and the logic of the interlocks could be considered "automatic" and "smart", but the act of docking is purely manual and controlled only by the user.

Still referring to FIG. 1A, the smart system further comprises the medical transporter 100 itself as well, wherein the medical transporter 100 comprises: a table T, a bed 20, a base B having at least one wheel W; and a lift portion L, the lift portion L coupling the table T with the base B, and the lift portion L configured to adjust elevation of the table T in relation to the base B. The smart system further comprises a deployment mechanism having a motor-and-rail system 40 for facilitating at least one of: deployment of the bed 20 from the table T and into a scanning volume $V_s$ of the imaging apparatus I; return of the bed 20 from the scanning volume $V_s$ of the imaging apparatus I to the table T; deployment of an active docking module of the docking module D from the base B to a passive docking module of the docking module D coupled with a receiver portion R (FIG. 5) of the imaging apparatus I; and return of active docking module to the base B from the passive docking module coupled with the receiver portion R of the imaging apparatus I; and a self-positioning mechanism for automatically aligning the bed 20 with the scanning volume $V_s$ of the imaging apparatus I and the at least one smart coupler, e.g., the latching mechanism, configured to couple the bed 20 with the patient positioner 25 of the imaging apparatus I in at least one orthogonal direction. The bed 20 further comprises a tongue portion 21 (FIGS. 4A and 4B) configured to interface with an MRI head coil (not shown) of the imaging apparatus I. The lift portion L comprises a housing 43, a weighing mechanism 51, and a lifting mechanism 52 (FIG. 5). The housing 43 comprises a bellows configuration, by example only. The lifting mechanism 52 comprises an elevation adjustment mechanism (FIG. 5) configured to adjust elevation of the table T in relation to the base B in at least one manner of manually, mechanically, electronically, and automatically. In further embodiments, the motor system is entirely housed within the imaging apparatus wherein the medical transporter is passive.

Figure 1B:
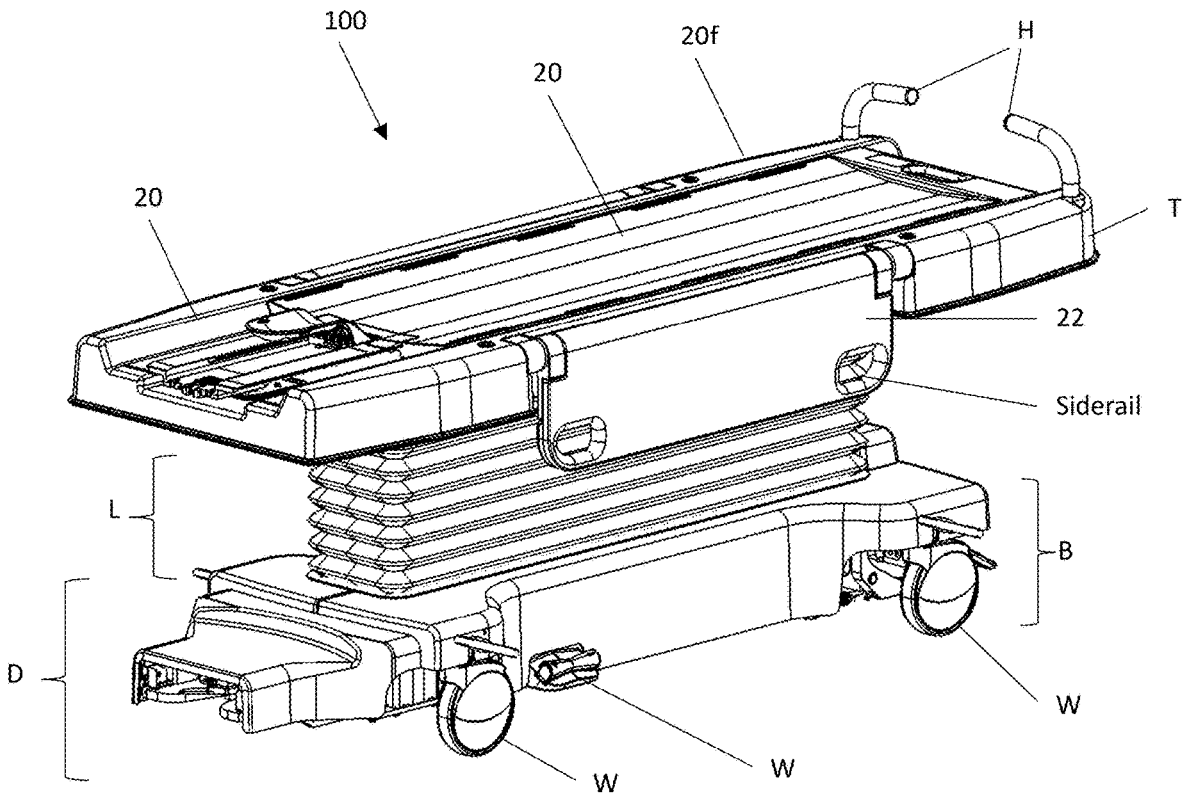
FIG. 1B is a diagram illustrating a perspective view of a medical transporter, such as an MRI transporter, adaptable for operation by a smart system, the transporter having various enclosures, in accordance with an embodiment of the present disclosure.
Figure 1C:
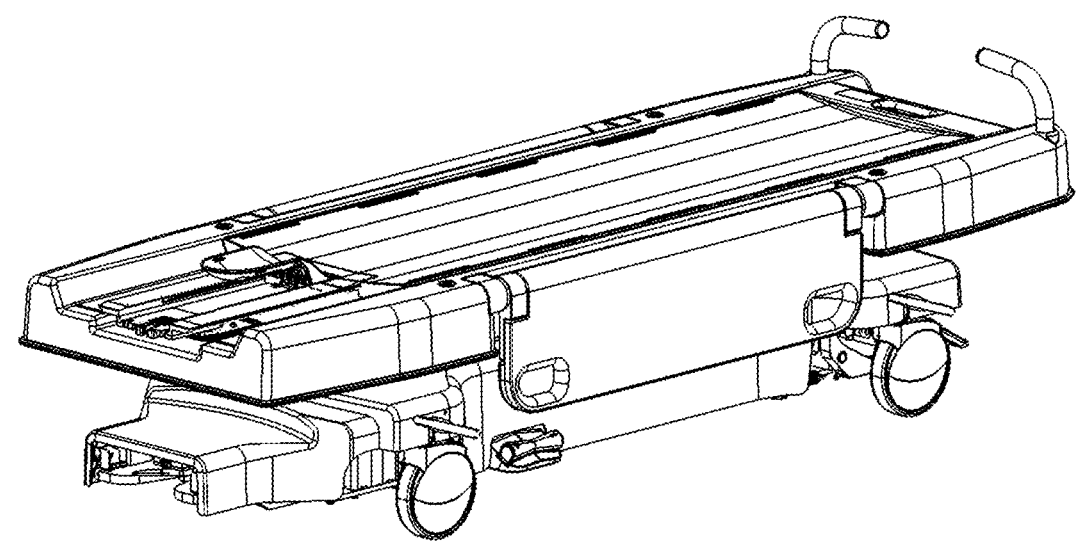
Figure 3:
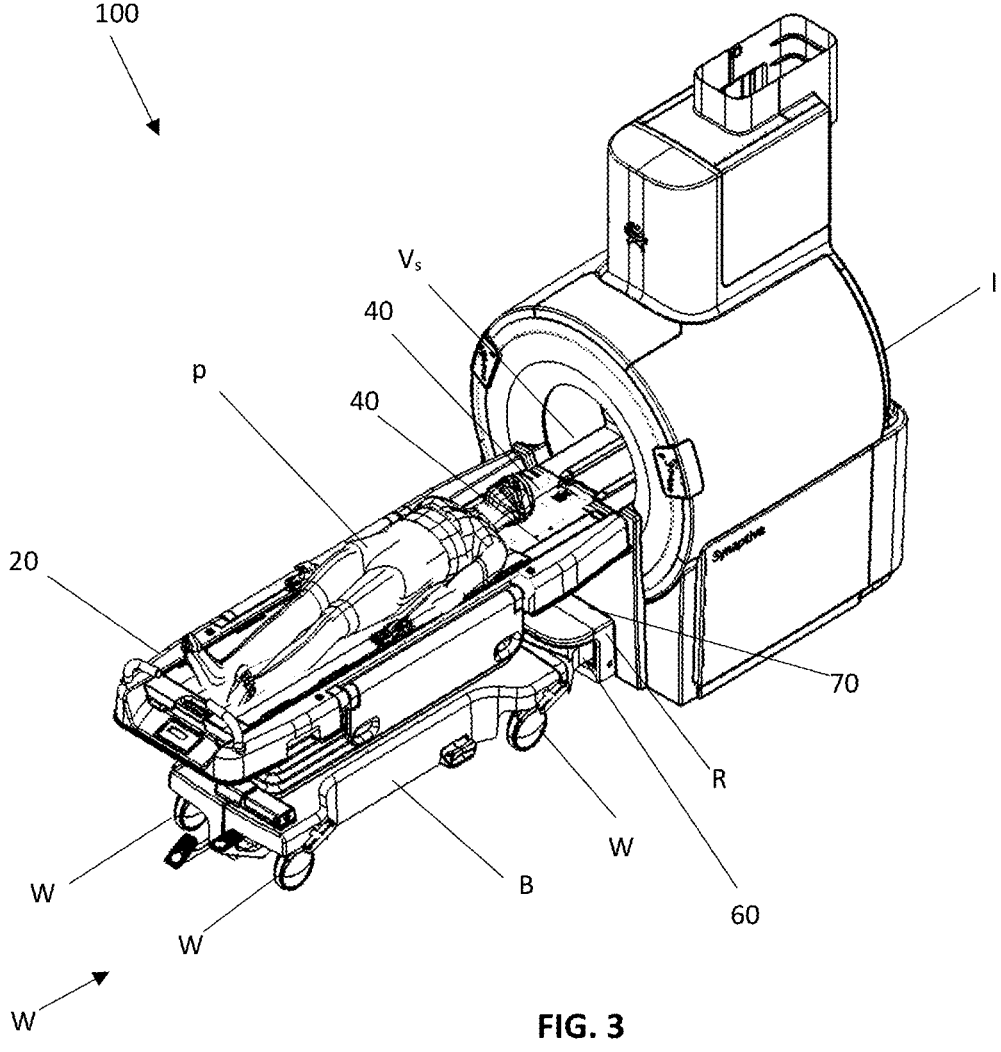
FIG. 3 is a diagram illustrating a perspective view of a medical transporter, implementable with a smart system, docked, by way of a docking module, in relation to a piece of medical equipment, in accordance with an embodiment of the present disclosure.

Still referring to FIG. 1A and ahead to FIG. 1B, the smart system further comprises: at least one indicator 60 (FIG. 3) disposable in relation to the medical transporter 100 and configured to indicate a real-time position of the medical transporter 100; and at least one detector 70 (as shown in FIG. 3) disposable in relation to the imaging apparatus I and configured to detect the at least one indicator 60. The at least one indicator 60 comprises at least one of: at least one tracking marker, at least one fluorescent tracking marker, and at least one infrared tracking marker. The at least one detector 70 comprises at least one of: at least one sensor, at least one optical sensor, at least one photo-sensor, at least one photo-detector, at least one electric eye, at least one infrared sensor, and at least one photo-interrupter. The smart system further comprises: a user interface, the user interface comprising at least one of: a foot pedal, e.g., a foot pedal 81 (FIGS. 4A and 4B), a handle, e.g., a handle, a joystick, and a graphic user interface, the user interface (not shown) facilitating at least one of activating, controlling, and manually overriding at least one of: the at least one coupler, the deployment mechanism, and the self-positioning mechanism. The self-positioning mechanism comprises at least one of: a patient positioner, a belt-drive system, and a cable carrier system.

Referring to FIG. 1B, this diagram illustrates a perspective view of a medical transporter 100, such as an MRI transporter, adaptable for operation by a smart system, the transporter 100 having various enclosures, in accordance with an embodiment of the present disclosure. The various enclosures comprise an upper enclosure 101 configured to accommodate the table T, a lower enclosure 102 configured to accommodate the base B, and a dock cover 103 configured to accommodate the docking module D.

Figure 2A:
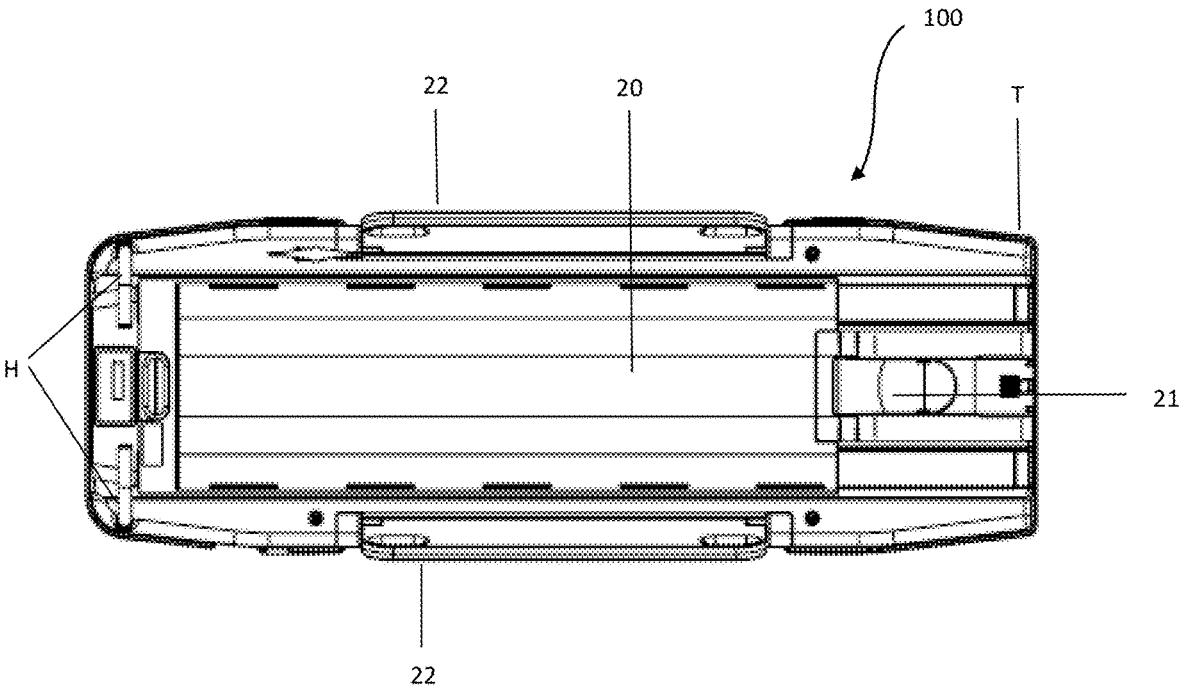
FIG. 2A is a diagram illustrating a plan view of a medical transporter, such as an MRI transporter, implementable with a smart system, in accordance with an embodiment of the present disclosure.

Referring to FIG. 2A, this diagram illustrates, in a plan view, a medical transporter 100, such as an MRI transporter, implementable with a smart system, in accordance with an embodiment of the present disclosure. The transporter 100 comprises a table T, a bed 20 operably coupled with the table T, a base B, and a lifting portion L configured to couple the table T with the base B and to adjust elevation of the table T in relation to the base B (FIGS. 1A and 1B). The bed 20 further comprises a tongue portion 21 (FIGS. 4A and 4B) configured to interface with an MRI head coil (not shown) of the imaging apparatus I.

Figure 2B:
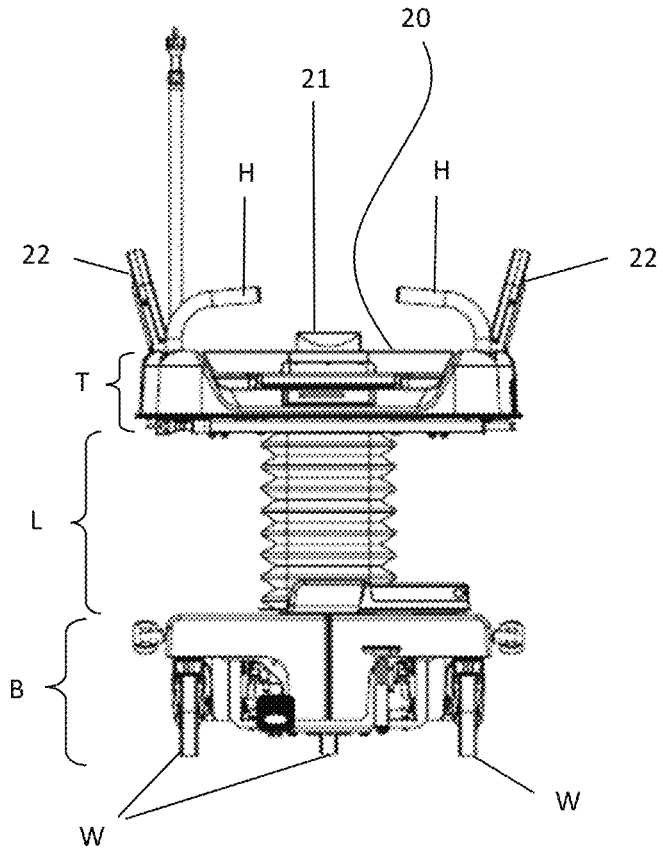
FIG. 2B is a diagram illustrating a front view of the medical transporter, as shown in FIG. 2A, in accordance with an embodiment of the present disclosure.

Referring to FIG. 2B, this diagram illustrates, in a front view, the medical transporter 100, as shown in FIG. 2A, in accordance with an embodiment of the present disclosure. The transporter 100 further comprises handles H operably coupled with the table T and configured to facilitate manual movement of the transporter 100. The transporter 100 further comprises side rails 22 operably coupled with the table T and configured to secure a patient P on the bed 20. The lift portion L comprises a housing 43, a weighing mechanism 51, and a lifting mechanism 52 (FIG. 5). The housing 43 comprises a bellows configuration, by example only. The lifting mechanism 52 comprises an elevation adjustment mechanism (FIG. 5) configured to adjust elevation of the table T in relation to the base B in at least one manner of manually, mechanically, electronically, and automatically.

Figure 2C:
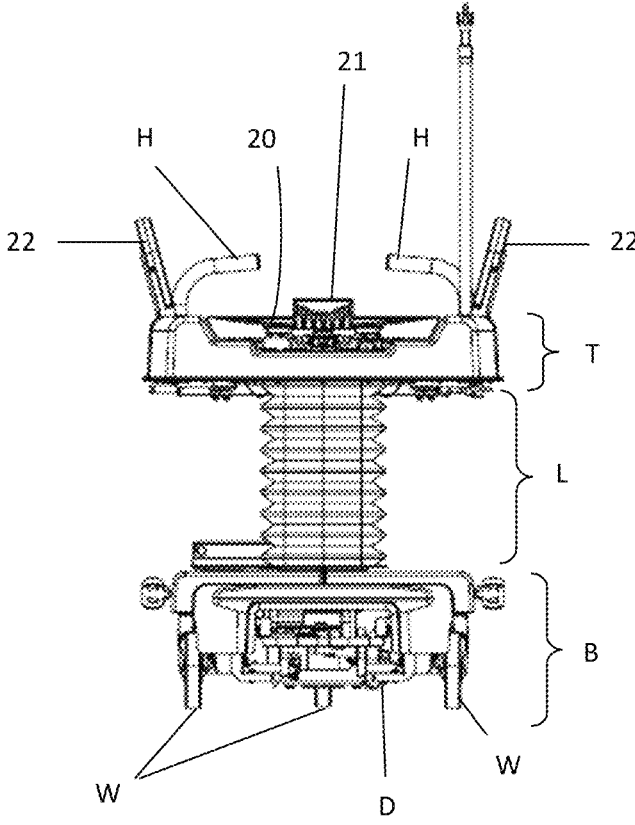
FIG. 2C is a diagram illustrating a rear view of the medical transporter, as shown in FIGS. 2A and 2B, in accordance with an embodiment of the present disclosure.

Referring to FIG. 2C, this diagram illustrates, in a rear view, the medical transporter 100, as shown in FIGS. 2A and 2B, in accordance with an embodiment of the present disclosure. The transporter 100 further comprises handles H operably coupled with the table T and configured to facilitate manual movement of the transporter 100. The lift portion L comprises a housing 43, a weighing mechanism 51, and a lifting mechanism 52 (FIG. 5). The housing 43 comprises a bellows configuration, by example only. The lifting mechanism 52 comprises an elevation adjustment mechanism (FIG. 5) configured to adjust elevation of the table T in relation to the base B in at least one manner of manually, mechanically, electronically, and automatically. The docking module D is shown.

Figure 2D:
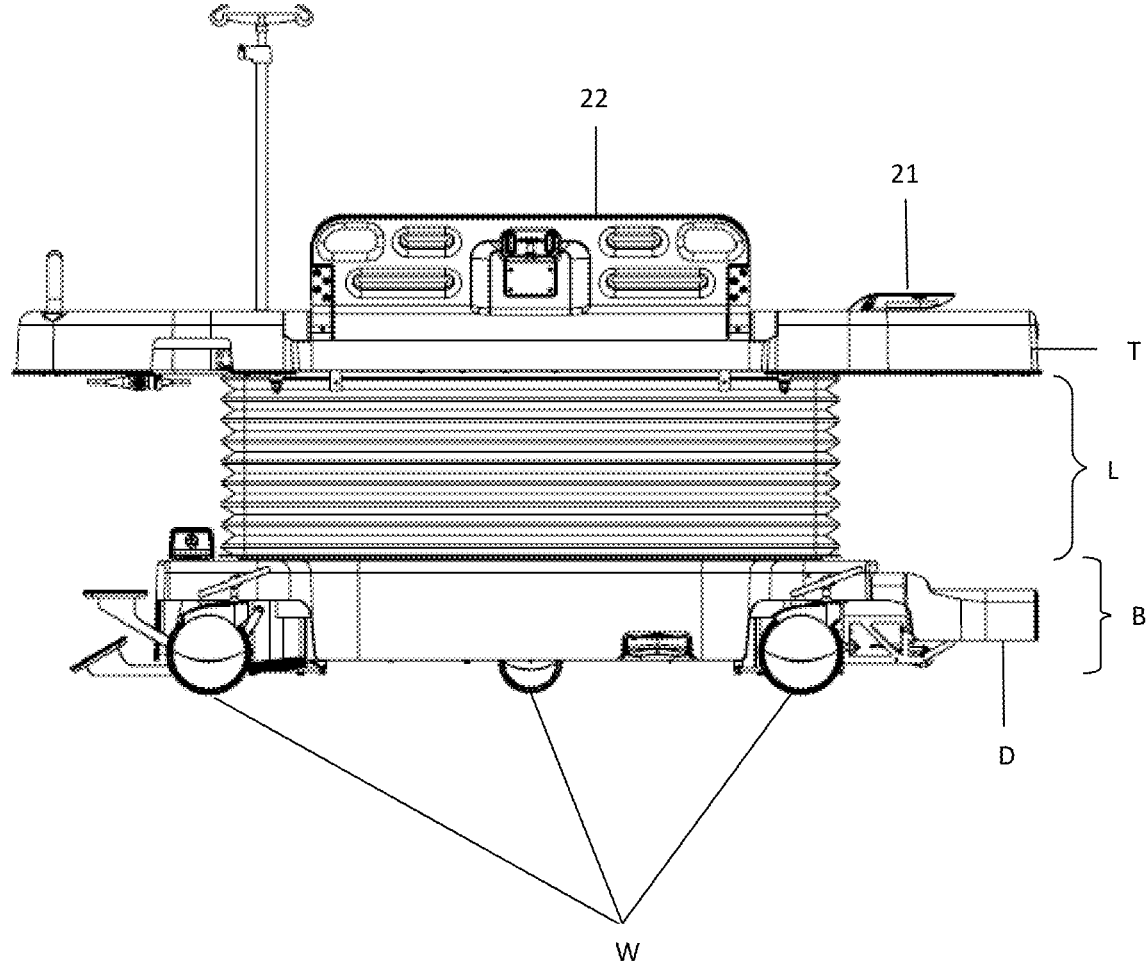
FIG. 2D is a diagram illustrating a side view of the medical transporter, as shown in FIGS. 2A-2C, in accordance with an embodiment of the present disclosure.

Referring to FIG. 2D, this diagram illustrates, in a side view, the medical transporter 100, as shown in FIGS. 2A-2C, in accordance with an embodiment of the present disclosure. The lift portion L comprises a housing 43, a weighing mechanism 51, and a lifting mechanism 52 (FIG. 5). The housing 43 comprises a bellows configuration, by example only. The lifting mechanism 52 comprises an elevation adjustment mechanism (FIG. 5) configured to adjust elevation of the table T in relation to the base B in at least one manner of manually, mechanically, electronically, and automatically. The transporter 100 further comprises side rails 22 operably coupled with the table T and configured to secure a patient P on the bed 20.

Figure 2E:
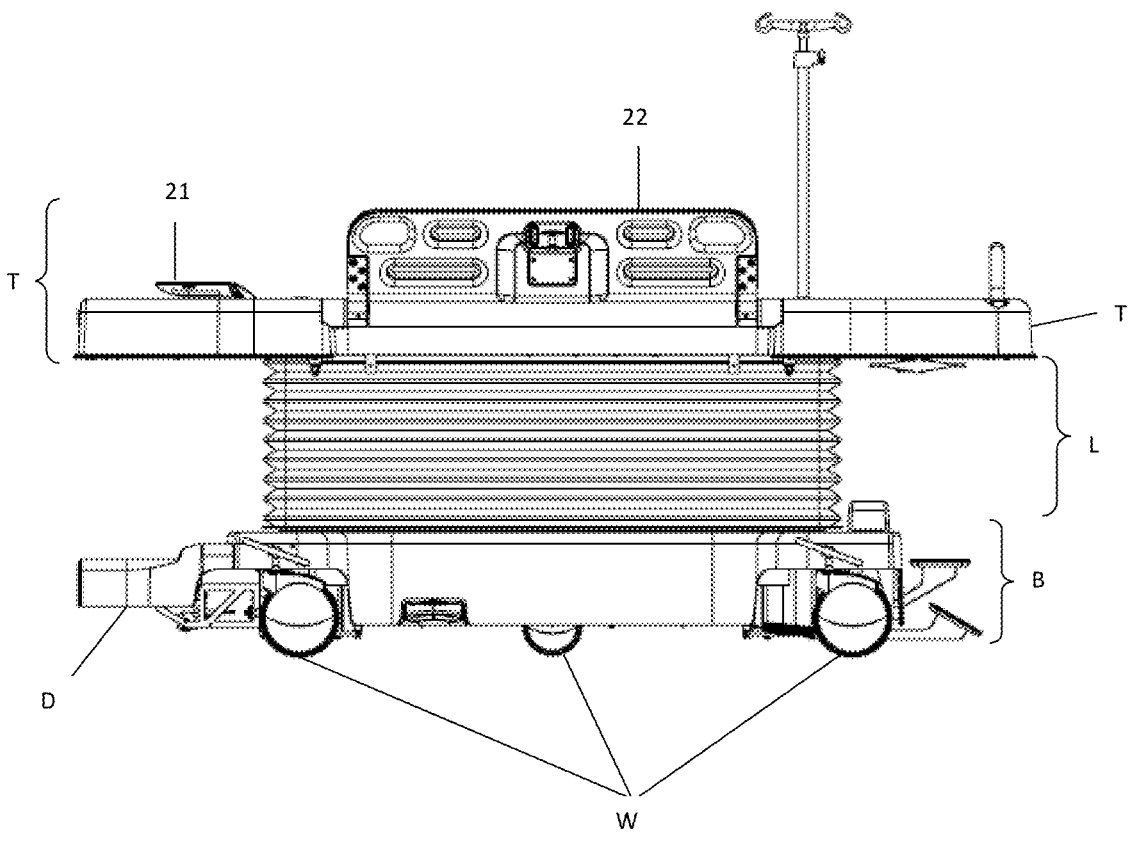
FIG. 2E is a diagram illustrating an opposing side view of the medical transporter, as shown in FIGS. 2A-2D, in accordance with an embodiment of the present disclosure.

Referring to FIG. 2E, this diagram illustrates, in an opposing side view, the medical transporter 100, as shown in FIGS. 2A-2D, in accordance with an embodiment of the present disclosure. The lift portion L comprises a housing 43, a weighing mechanism 51, and a lifting mechanism 52 (FIG. 5). The housing 43 comprises a bellows configuration, by example only. The lifting mechanism 52 comprises an elevation adjustment mechanism (FIG. 5) configured to adjust elevation of the table T in relation to the base B in at least one manner of manually, mechanically, electronically, and automatically. The transporter 100 further comprises side rails 22 operably coupled with the table T and configured to secure a patient P on the bed 20.

Referring to FIG. 3, this diagram illustrates, in a perspective view, a medical transporter 100, such as an MRI transporter, implementable with a smart system, docked, by way of a docking module, in relation to a piece of medical equipment, such as an imaging apparatus, in accordance with an embodiment of the present disclosure. Components of the smart system S are disposable within at least one of a base B, a table T, and a lift portion L of the medical transporter A. The smart system S is configured to couple the medical transporter A with medical equipment, such as an imaging apparatus I, e.g., an MRI machine (FIG. 1B), by way of a smart docking module D. The smart docking module D comprises a non-magnetic material and at least one coupler (FIG. 5). The apparatus 100 accommodates a patient P as shown.

Figure 4A:
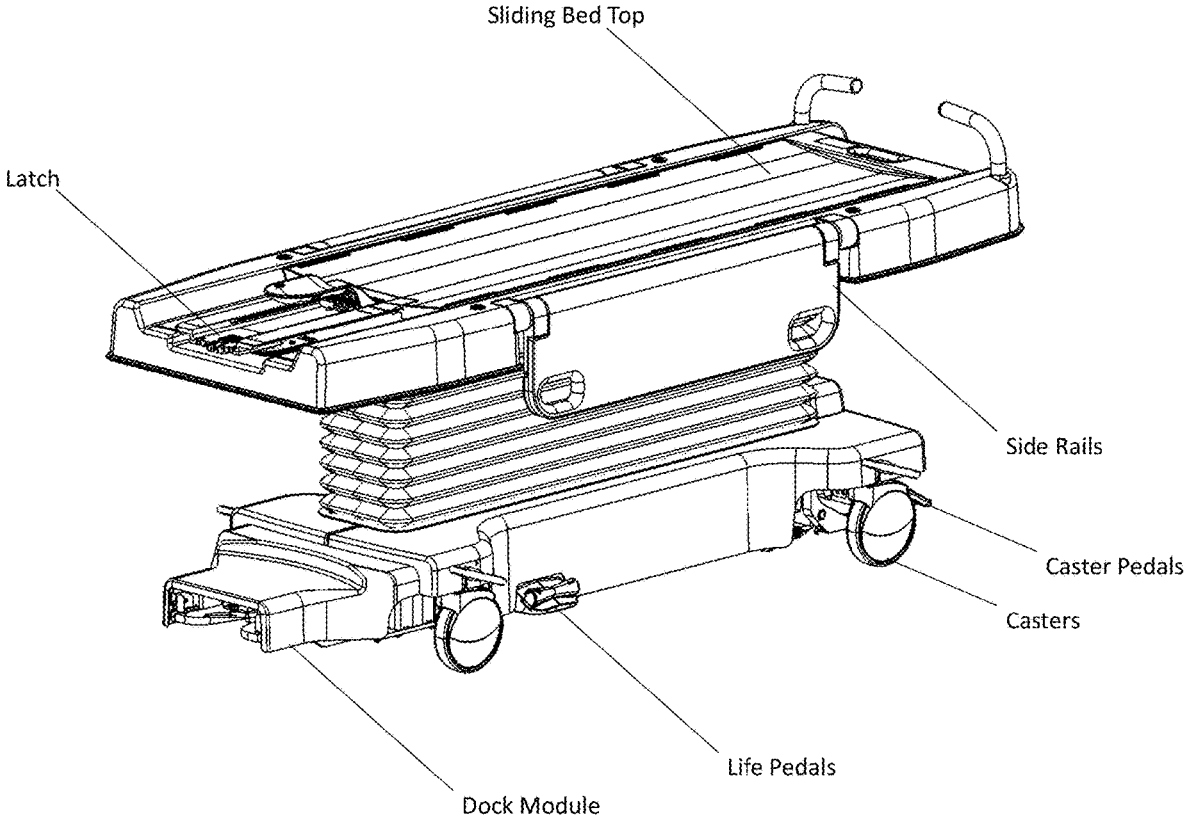
FIG. 4A is a diagram illustrating a perspective view of a medical transporter, the bed configured to slide along a motor-and-rail system, and the bed being disposed in a forward position, in accordance with an embodiment of the present disclosure.
Figure 5:
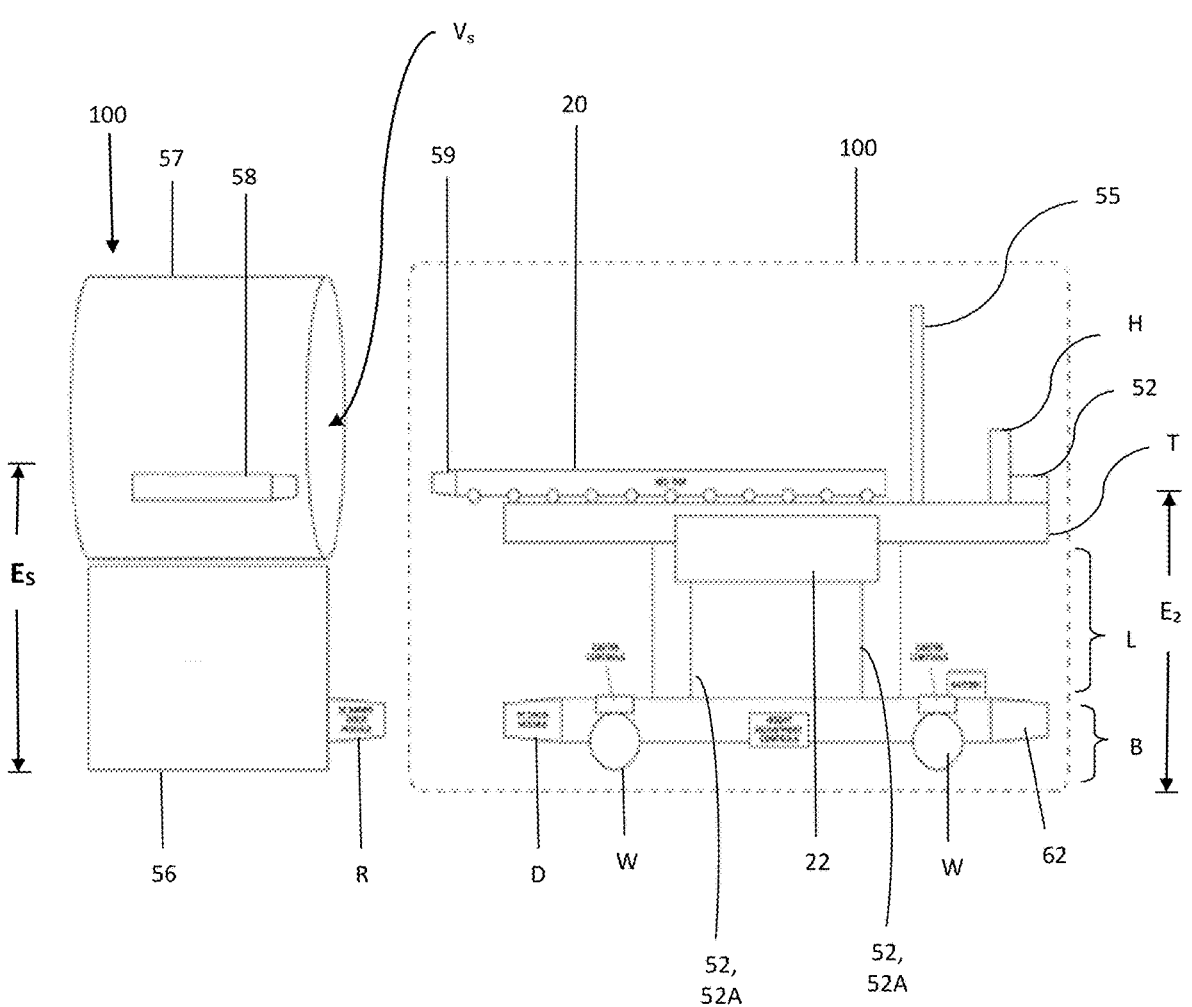
FIG. 5 is a schematic diagram of a medical transporter, as shown in FIGS. 1A-4B, the transporter implementable with a smart system, the smart system configured to determine a patient's weight and to automatically adjust elevation of the bed based on the patient's weight, in accordance with an embodiment of the present disclosure.

Referring to FIG. 4A, this diagram illustrates, in a perspective view, a medical transporter 100, the bed 20 configured to slide along a motor-and-rail system 40 (FIG. 1A), and the bed 20 being disposed in a forward position, in accordance with an embodiment of the present disclosure. The forward position is a deployed position for the bed 20. The transporter 100 further comprises at least one wheel pedal 63 operably coupled with at least one wheel W. The transporter 100 further comprises at least one latch 46 operably coupled with the patient positioner. The transporter 100 further comprises at least one lift pedal 61 operably coupled with the lifting mechanism 52.

Figure 4B:
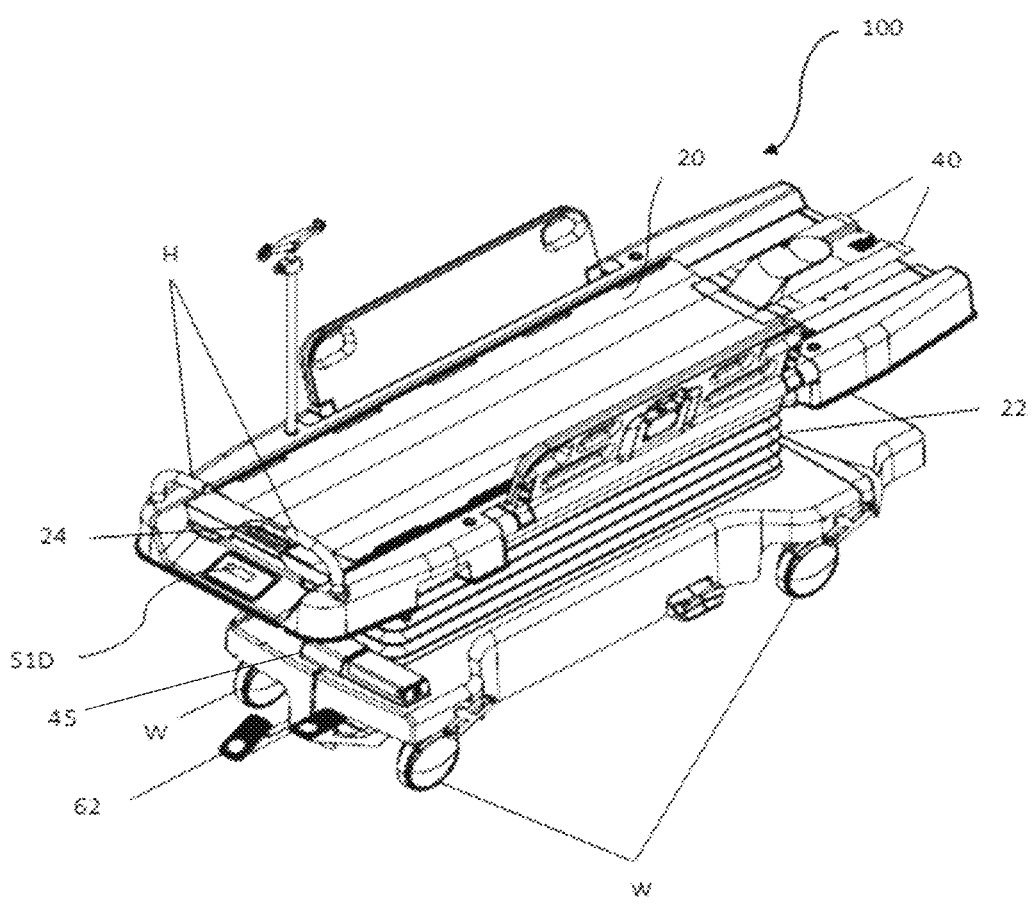
FIG. 4B is a diagram illustrating a perspective view of a medical transporter, as shown in FIG. 4A, the bed configured to slide along a motor-and-rail system, and the bed being disposed in an aft position, in accordance with an embodiment of the present disclosure.

Referring to FIG. 4B, this diagram illustrates, in a perspective view of a medical transporter 100, as shown in FIG. 4A, the bed 20 configured to slide along the motor-and-rail system 40 (FIG. 1A), and the bed 20 being disposed an aft position, in accordance with an embodiment of the present disclosure. The aft position is an undeployed position for the bed 20. The weighing mechanism 51 further comprises a display 51d configured to show the weight of the patient. The smart system further comprises at least one power supply 45, such as at least one battery. The transporter 100 further comprises at least one dock pedal 62 operably coupled with the docking module D. The transporter 100 further comprises an emergency release mechanism 24.

Referring to FIG. 5, this schematic diagram illustrates a medical transporter 100, as shown in FIGS. 1A-4B, the transporter implementable with a smart system, the smart system configured to manually adjust elevation of the bed 20. In the alternative, the elevation of the bed 20 can be adjusted automatically based on the patient's weight, wherein the transporter 100 is ready to dock with an imaging system I, such as an MRI machine, in accordance with an embodiment of the present disclosure. In further embodiments, the sensors and the logic of the interlocks could be considered "automatic" and "smart", but the act of docking is manual and controlled only by the user. The transporter 100 is further configured to at least one of: operate with a Synaptive® Medical MR System, to transport a patient P to, and from, a MR room, e.g., with assistance of two operators in its maneuver, to accommodate a safe working load in a range of up to approximately 250 kg, to fit within hospital corridors, thereby allowing smooth maneuvering, slide the bed 20 into the magnet bore of an MRI machine for scanning, and determine accuracy of positioning in the bore for scans by way of a bed motion system of the smart system.

Still referring to FIG. 5, the base B of the transporter 100 comprises a plurality of wheels W. For example, the plurality of wheels W comprises four primary casters, equipped with a total lock, and one centrally-mounted directionally-locking caster for steering, wherein all the casters are simultaneously actuated through one of four pedals mounted by each primary caster. The pedals rotate to an angle in a range of up to approximately 30 degrees to place the casters into one of the following states: (a) a braking state, wherein a red side of caster pedal is disposed in a "down" position, wherein all casters are locked, and whereby the transporter 100 is unable to move; (b) a neutral state, wherein the caster pedal is disposed in a horizontal position, and wherein all casters are unlocked and free to swivel; and (c) a steering state, wherein a green side of the caster pedal is in a "down" position, and wherein the centrally-mounted directionally-locking caster is directionally locked, whereby a pivot is triggered to facilitate steering.

Still referring to FIG. 5, the transporter 100 comprises at least one handle H. For example, the at least one handle H comprises a plurality of handles operably coupled with table T, e.g., proximate the foot (aft section) of the table T to facilitate maneuvering. The dock and undock operation is controlled through a set of two foot pedals: one dock pedal 62 to dock the transporter 100 with the imaging apparatus I, e.g., an MRI scanner. and the other dock pedal 62 to undock the transporter 100 from the imaging apparatus I. The bed 20 is moved in and out of the bore or scanning volume $V_s$ of the imaging portion 57 of the imaging apparatus I via the bed motion system (not shown) of the smart system. The bed motion system is configured to operably couple with the bed 20 by way of a latching mechanism 59. Latching is automatic, as instructed by the latch system of the smart system, when the transporter 100 is docked and disposed at a scanning height $E_s$. The bed motion system comprises an emergency release system that enables a user to unlatch the bed 20 and remove the bed 20 from the bore or scanning volume $V_s$ in an event of an emergency. The transporter 100 comprises various pole interfaces 55, e.g., four poles, to accommodate a plurality of intravenous (IV) drip bags. For patient safety during transport and scanning, the transporter 100 is equipped with side rails 22 and provisions (not shown) for straps. Enclosures (FIG. 1B), e.g., for the table T, the base B, and the docking module D, on the transporter 100 provide protection against mechanical hazards associated with various parts of the imaging apparatus I as well as the apparatus 100 itself.

Still referring to FIG. 5, the bed 20 is configured to support the patient P. The bed 20 is configured to slide into the bore or scanning volume V_s to position the patient P at the scanning position. A head rest (not shown) is coupled with the bed 20 and is configured to support the patient's head and a head coil. The dimensions of the bed 20 are selected to fit a patient P with shoulder width in a range of up to approximately 532 mm and height in a range of up to approximately 1901 mm. The bed 20, including the head rest, comprises a biologically-compatible padding for patient comfort. The bed 20 is further configured to accommodate at least one strap (not shown) for restraining a patient's body during transport or scanning if needed. A profile of the bed 20 matches that of the accessible bore or scanning volume V_s of the imaging apparatus I, whereby safe positioning of the patient P for scanning is facilitated.

Still referring to FIG. 5, the docking module D facilitates mechanical coupling of the transporter 100 to the scanner. The docking operation is controlled by way of a plurality of dock pedals 62, e.g., two foot pedals (FIG. 4B). By pressing one dock pedal 62, the docking module D docks with a receiver portion R of a base 56 of an imaging apparatus I. By pressing the other dock pedal 62 (not shown), the docking module D undocks from the receiver portion R of the base 56 of the imaging apparatus I. For a successful docking operation, the transporter 100 must be aligned with a scanner portion 57 of the imaging apparatus I. However, to account for human error, such as experienced in the related art, some tolerance is provided.

Still referring to FIG. 5, once the transporter 100 is within an allowable lateral and angular range, the docking module D guides the transporter 100 into position, by way of a smart system, as an operator pushes the transporter 100 toward the imaging apparatus I. When one dock pedal 62 is pressed, the docking module D draws the transporter 100 into a position that facilitates the bed motion system to successfully latch the transporter 100 and locks the transporter 100 in place, e.g., with the receiver portion R of the base 56. A secondary undocking feature (not shown) is provided on the transporter 100 for servicing and maintenance in an event of failure of the docking module D.

Still referring to FIG. 5, the latching mechanism 59 is configured to mechanically couple the bed 20 with the bed motion system, e.g., comprising a patient positioner 58 of the imaging apparatus I for positioning of the patient P in a bore or scanning volume V_s of the imaging portion 57 of the imaging apparatus I. The latching mechanism 59 comprises a dock-latch interlock configured to automatically unlatch the bed 20 from the bed motion system by pressing the other dock pedal 62, e.g., an undock pedal. The transporter 100 further comprises an emergency release feature 24 (FIG. 4B), e.g., a single fault-tolerant manual emergency release, configured to decouple the latching mechanism 59 from the patient positioner 58 during an emergency through an actuator (not shown), e.g., disposed at the foot (aft portion) of the bed 20.

Still referring to FIG. 5, the lift portion L comprises a lifting mechanism 52, the lifting mechanism 52 comprising an electromechanical lifter (not shown) which adjusts elevation of table T, and effectively that of the bed 20, in relation to the base B of the transporter 100. At a maximum height, the bed 20 aligns with the imaging portion 57 of the imaging apparatus I to allow for a smooth travel of the bed 20 into the bore or scanning volume V_s of the imaging portion 57 of the imaging apparatus I. A minimum height is selected in a range below approximately the average working height of hospital staff personnel to allow for easy transfer of a patient P onto the transporter 100. The transporter 100 further comprises a feature configured to calibrate the maximum height by service personnel to account for slight variations in installation height of the imaging apparatus I. The lift mechanism 52 and weighing mechanism 51, e.g., comprising a scale, are powered by a power supply, such as at least one removable, rechargeable, battery, e.g., at least one lithium (Li) ion battery. A battery charger (not shown) may be disposed in a control room, by example only. At least one power supply and at least one charger is provided with each transporter 100 to ensure continuous workflow even if a power supply is drained or fails. The transporter 100 further comprises the at least one power supply and the at least one charger.

Still referring to FIG. 5, the side rails 22 comprise movable side rails, for example, which can be locked in an upright locked configuration (FIG. 28A) to provide protection against mechanical hazards associated with moving the transporter 100. The side rails 22 can also be locked in a horizontal flat position (FIG. 28B) or rotated down (FIG. 28C) for ease of patient transfers.

Still referring to FIG. 5, the weighing mechanism 51 comprises a scale configured to determine a weight of a patient P disposed on the bed 20 when not undergoing scanning. The scale is deactivated when the bed 20 is extended and after a certain amount of time of inactivity and when prompted by the user. The tare value of the scale system persists until the scale is tared again, even after the scale is deactivated.

Figure 6:
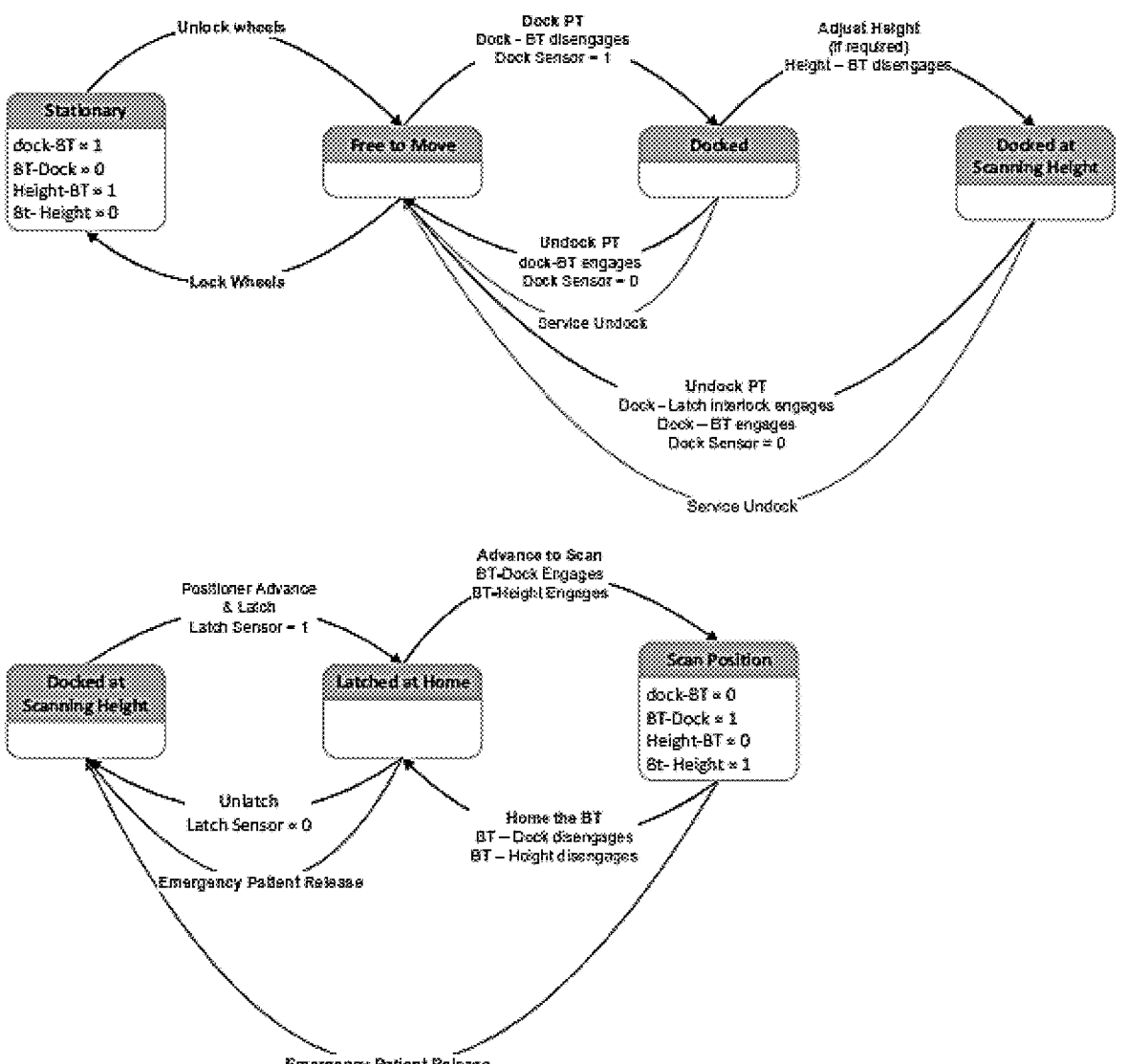
FIG. 6 is a diagram illustrating the workflow of the interlock logic of a smart system, comprising a weighing mechanism and a lifting mechanism, for controlling operation of a medical transporter, in accordance with an embodiment of the present disclosure.

Referring to FIG. 6, this diagram illustrates workflow of a smart system, comprising a weighing mechanism 51 and a lifting mechanism 52, for controlling operation of a medical transporter 100, in accordance with an embodiment of the present disclosure. The smart system is dynamically operable and comprises at least one interlock operable by switch logic. For example, the smart system comprises a plurality of interlocks, e.g., five interlocks, to ensure the patient's safety during transport and scanning. This workflow diagram shows operational relationships among various input elements and various output elements. The smart system controls workflow by way of a controller or processor operable by way of a set of executable instructions storable in relation to a memory, e.g., a nontransient memory device. In further embodiment, the controls may be mechanical and may not include controllers or processors. One exception is the "BT-Height" interlock where the position of the bed may be fully retracted in order for the user to actuate the lift mechanism. This is controlled by a switch that is mounted on the table T and actuated by the bed 20 when the bed 20 is fully retracted. The lift mechanism may only move when this switch is depressed. The controller may be operably coupled with any combination of elements of the present disclosure, including any combination of interlocks in the plurality of interlocks. Examples of the interlocks are described as follows.

Still referring to FIG. 6, a dock-bed interlock ("Interlock #1") prevents the bed 20 from extending in relation to the table T when the transporter 100 is undocked from the imaging apparatus I. In docking, the dock-bed interlock is disengaged, wherein the transporter 100 is docked with the imaging apparatus I, and wherein the bed 20 is permitted to extend in relation to the table T. In undocking, the dock-bed interlock is engaged, wherein the transporter 100 is undocked from the imaging apparatus I, and wherein the bed 20 is prohibited from extending in relation to the table T.

Still referring to FIG. 6, a bed-dock interlock ("Interlock #2") prevents the transporter 100 from undocking when bed 20 is extended. In docking, the bed-dock interlock is engaged, wherein the transporter 100 is docked with the imaging apparatus I, and wherein the bed 20 is permitted to extend in relation to the table T. In relation to undocking, the bed-dock interlock is disengaged, wherein the transporter 100 is undocked from the imaging apparatus I, and wherein the bed 20 is permitted to retract in relation to the table T.

Still referring to FIG. 6, a height-bed interlock ("Interlock #3") prevents the bed 20 from extending when the table T of the transporter 100 is not disposed at an elevation compatible with a geometry of the bore or scanning volume $V_s$ of the imaging portion 57 of the imaging apparatus I, e.g., a scanning height $E_s$. When the table T is disposed at an elevation in a range lower than that of the scanning height $E_s$, the height-bed interlock is engaged, wherein the bed 20 is prohibited from extending in relation to the table T. When the table T is disposed at an elevation in a range compatible with that of the scanning height $E_s$, the height-bed interlock is disengaged, wherein the bed 20 is permitted to extend in relation to the table T.

Still referring to FIG. 6, the bed-height interlock ("Interlock #4") prevents the table 20 from lowering or moving in relation to the base B while the bed 20 is extended. When the bed-height interlock is engaged, the transporter 100 is docked, wherein the table T is disposed at an elevation compatible with the scanning height $E_s$, wherein the bed 20 is extended in relation to the table T, and wherein the table T is prohibited from moving in a vertical direction in relation to the base B. When the bed-height interlock is disengaged, the transporter 100 is undocked, wherein the bed 20 is retracted in relation to the table T, and wherein the table T is permitted to move in a vertical direction in relation to the base B.

Still referring to FIG. 6, a dock-latch interlock ("Interlock #5") ensures that the latch disengages before transporter 100 moves away from the imaging apparatus I during an undocking operation. When the dock-latch interlock is engaged, the transporter 100 is undocked and the patient positioner 58 (FIG. 5) is prohibited from coupling with the bed 20. When the dock-latch interlock is disengaged, the transporter 100 is docked and the patient positioner 58 (FIG. 5) is permitted to couple with the bed 20 by way of the latch.

Still referring to FIG. 6, a height-sensor interlock ("Interlock #6") communicates with the smart system, if the table T of the transporter 100 is disposed at a scanning height $E_s$, by interrupting a photo-interrupter sensor coupled with the docking module D, photo-interrupter sensor disposed in relation to an outboard portion of the docking module, e.g., on the scanner side dock assembly. When the heightsensor interlock is engaged, the table T of the transporter 100, as docked, is disposed at the scanning height $E_s$, wherein a flag (not shown) rotates in a direction, whereby photo-interrupter sensor is interrupted, e.g., prohibited from sensing. When the height-sensor interlock is disengaged, the table T of the transporter 100, as undocked, is lowered in relation to the scanning height $E_s$, wherein a flag (not shown) rotates in an opposite direction, whereby photo-interrupter sensor is permitted to sense.

Still referring to FIG. 6, shows the transition between different states of the transporter 100 as well as the status of the plurality of interlocks, e.g, a status of each of ("Interlock #1") through ("Interlock #4"). When the transporter 100 is in transport mode, the dock-bed interlock and dock-latch interlock are engaged. When the transporter 100 is lower than a scanning height $E_s$, the height-bed interlock is engaged. As soon as the transporter 100 is docked with the imaging apparatus I by activating the dock pedal 62, the dock-bed interlock and dock-latch interlock disengage, wherein the dock sensor is activated. The height-bed interlock may still be engaged at this point as the height (elevation) of the table T in relation to the base B can be adjusted while the transporter 100 is docked. When the transporter 100 is elevated to a scanning height $E_s$, the height-bed interlock disengages, wherein the height sensor is activated. When the transporter 100 is docked and at the scanning height $E_s$, both the dock sensor and the height sensor are activated. When both the dock sensor and the height sensor are activated, the imaging apparatus I, e.g., a scanner, recognizes that the transporter 100 is docked, wherein the bed motion system extends the patient positioner 58 from the bore or scanning volume $V_s$ of the imaging portion 57 of the imaging apparatus I, and whereby the patient positioner 58 is permitted to couple with, e.g., latch to, the bed 20. The bed 20 is pulled into the bore or scanning volume $V_s$ when an "advance to scan" button is pressed, e.g., by a user. The bed-height interlock and bed-dock interlock engage once the bed 20 is extended, wherein the table T of the transporter 100 is prohibited from lowering in relation to the base B, and wherein the transporter 100 is prohibited from undocking from the imaging apparatus I. To remove the patient P, the steps of the foregoing process are performed in a reverse order after the operator presses a "home" button operably coupled with an interface of the bed motion system.

Still referring to FIG. 6, in an emergency release operation, the emergency release mechanism 24 (FIG. 4B) is actuated, wherein the bed 20 unlatches from the bed motion system, and wherein the bed 20 is permitted to be manually moved onto the table T of the transporter 100 by an operator. The transporter 100 can then be undocked. The emergency patient release mechanism 24 requires activation through a lever located at the foot of the bed 20 of the transporter 100. A pull force is then transferred to the latch, whereby the latch opens. The transporter 100 further comprises a secondary transmission mechanism (not shown), for redundancy, to ensure that the emergency patient release mechanism 24 is single-fault tolerant.

Figure 7:
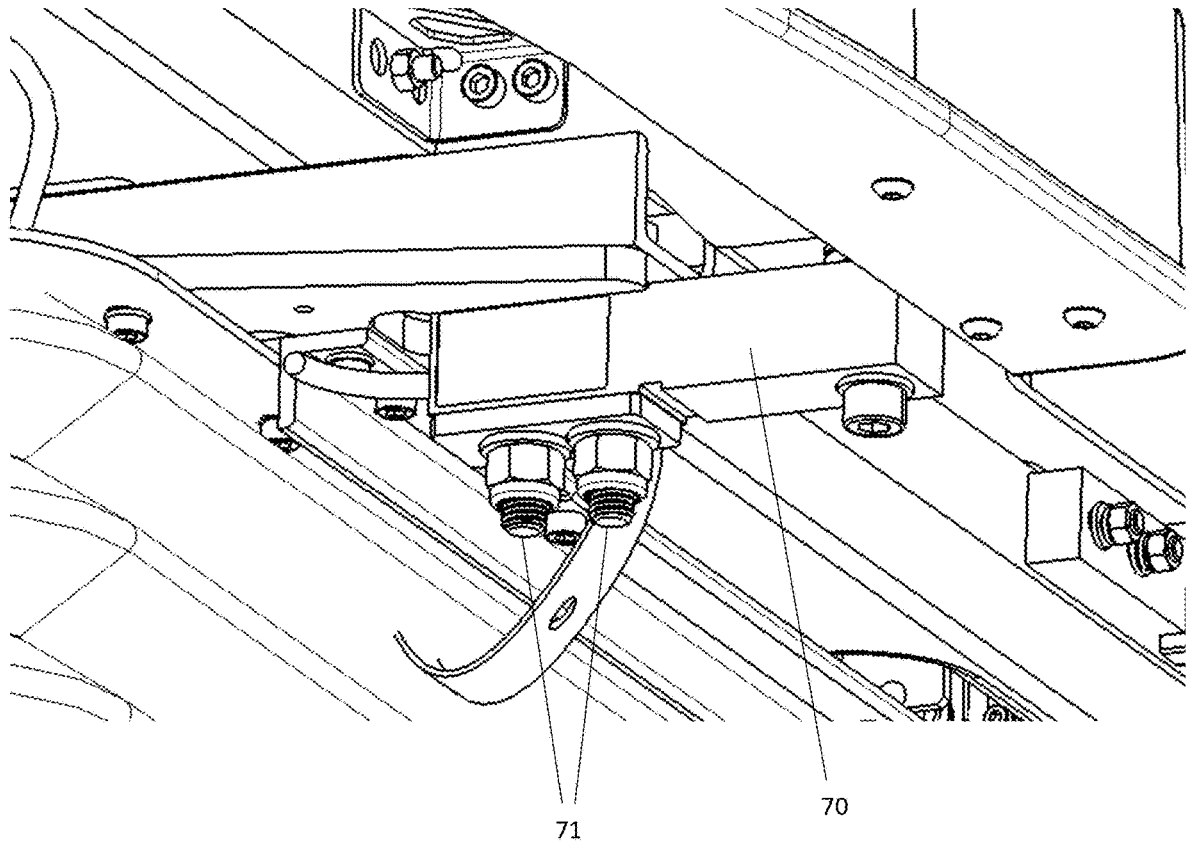
FIG. 7 is a diagram illustrating a perspective view of a plurality of load cells of a weighing mechanism, operable by a smart system implementable with a medical transporter, in accordance with an embodiment of the present disclosure.

Referring to FIG. 7, this diagram illustrates, in a perspective view, a plurality of load cells 70 of a weighing mechanism 51, operable by a smart system implementable with a medical transporter 100, in accordance with an embodiment of the present disclosure. The weighing mechanism 51 comprises a scale, the scale comprises a plurality of load cells 70, comprising four load cells 70, by example only, wherein each load cell 70 is disposed in relation to each corner of the table T. The weighing mechanism 51 further comprises at least one of: a scale indicator, a power box, a junction box, and a disconnect switch disposed between the bed 20 and the weighing mechanism 51.

Still referring to FIG. 7, the plurality of load cells 70 comprises at least one stainless-steel single-ended shear-beam load cell, e.g., having an "IEC IP67" rating from "Group Four Transducers." The IEC IP67 standard determines whether the electronic device is dust-tight and is also protected against the effects of temporary immersion in water. For example, the weighing mechanism 51 is configured to handle weight of a patient P in a range of up to approximately 551 lbs (250 kg). For example, the weighing mechanism 51 is configured to measure weight of a patient P lying on the bed 20 when not undergoing scanning. The weighing mechanism 51 comprises dimensions of each load cell having \an overall length of approximately 5.37 inches, a width of approximately 1.19 inches, and a thickness of approximately 1.19 inches. The scale is configured to couple with a scale indicator, the scale indicator configured to display the weight of the patient P, to change the units of measure, and to tare the value.

Still referring to FIG. 7, all components in the transporter 100 that comprise a ferromagnetic material are securely fastened in place to eliminate any projectile risk. The load cells 70 are likewise fastened and may be fastened with two bolts (not shown), e.g., "M12" bolts, with lock-nuts 71, wherein the bolts are torqued to a specified value to eliminate any projectile risk. The weighing mechanism 51 does not comprise any magnetic materials that electronic components in both the scale indicator and the scale power box would comprise.

Still referring to FIG. 7, by example only, the scale indicator comprises a display resolution (as shown in display 51D in FIG. 4B) to one decimal place of the unit of measurement. For example, the scale displays six digits in total; and weight can be displayed to at least 1 decimal place of the unit of measurement. The location of the decimal place can be adjusted in the software settings. The capacity of the scale comprises a range of approximately 100 kg to approximately 400 kg over a safe working load of the transporter 100, by example only. When inside and outside the magnet room, the scale comprises an accuracy of at least approximately +/−1.3 kg for weights less than 45 kg and an accuracy of at least approximately +/−3% or better for weights greater than or equal to approximately 45 kg. The scale indicator is configured to display information in a font and a font size that is ergonomically optimized for most users. The scale is configured to display a weight in at least one unit of: kilograms and pounds. The scale is configured to deactivate when any of the following occurs: (a) the bed 20 is extended, (b) after approximately 30 minutes of inactivity, (c) when prompted by a user. However, the scale is configured to retain a tare value, even after deactivation, until the scale is tared again after reactivation. Further, the tare value of the scale persists through a power cycle.

Figure 8:
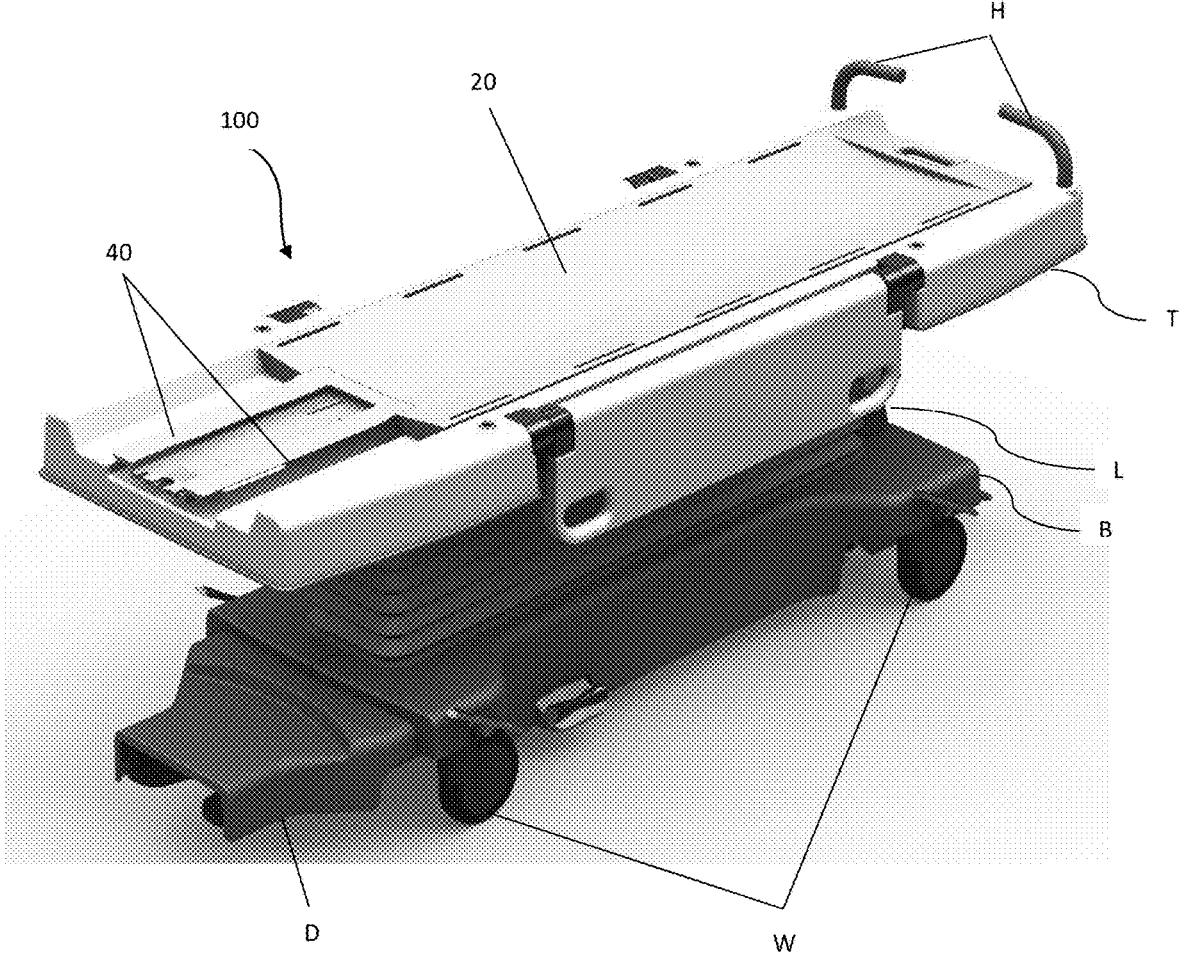
FIG. 8 is a diagram illustrating a perspective view of a medical transporter, without any exposed cables, in accordance with an embodiment of the present disclosure.

Referring to FIG. 8, this diagram illustrates, in a perspective view, a medical transporter 100, without any exposed cables (not shown), in accordance with an embodiment of the present disclosure. By example only, the transporter 100 further comprises at least one of cables and wires (not shown) configured to internally route. For instance, the cables and/or wires are routed away from any moving parts wherever possible; and, when not possible, the cables and/or wires are securely fastened, e.g., to a housing or enclosure. All cables and/or wires are routed beneath the frame and/or enclosures and will be secured with fasteners, such as cable ties and screw-in cable clips.

Figure 9:
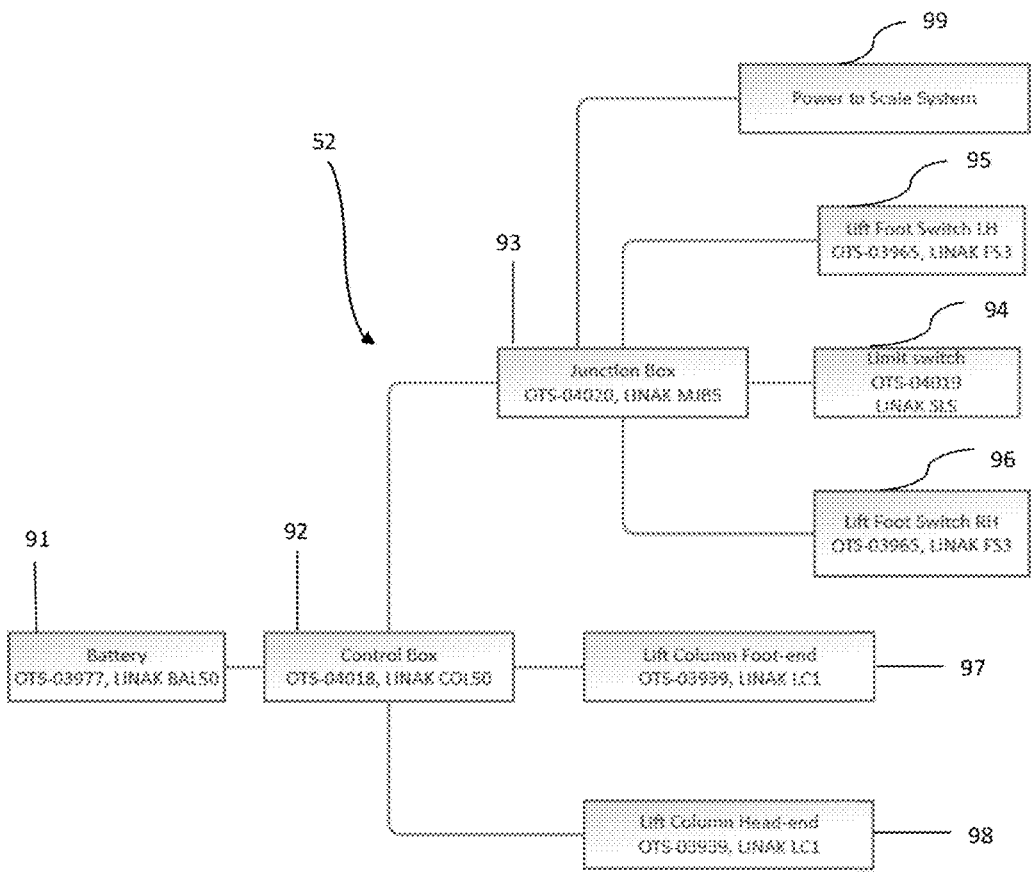
FIG. 9 is a schematic diagram illustrating components of a smart system, comprising a wiring mechanism and lifting mechanism, for controlling operation of a medical transporter, in accordance with an embodiment of the present disclosure.

Referring to FIG. 9, this schematic diagram illustrates components of a smart system, comprising a weighing mechanism 51, a power mechanism 99 and lifting mechanism 52, for controlling operation of a medical transporter 100, in accordance with an embodiment of the present disclosure. The lifting mechanism 52 is configured to adjust elevation of the table T of the transporter 100 in relation to the base B of the transporter 100, e.g., to facilitate adjusting elevation and improving accuracy for scanning a patient P of any size, shape, or weight, and to facilitate loading and unloading of the patient P, e.g., in relation to ergonomics.

Still referring to FIG. 9, the lift mechanism 52 comprises: at least one lifter, such as at least one lift column 52a (FIG. 5), e.g., a foot-end lift column 97 and a head-end lift column 98, at least one power supply 91, such as at least one battery, a control box 92, at least one lift control interface, such as a user-facing lift control, e.g., a left-hand lift foot-switch 95 and a right-hand lift foot switch 96, a junction box 93, a limit switch 94, and at least one interface 99 for a charger, such as an external charger for recharging at least one power supply 91 (not shown). The lift mechanism 52 further comprises at least one element (not shown) of: at least one associated cable, at least one associated cable coupler, at least one motor cables, a control cable, at least one lift column screws, at least one lift column cable lock, and a service handset configured to set the height for the table T, e.g., an initial scanning height, for the lift mechanism 52 to dispose the table T. The lift mechanism 52 is operable by way of a controller operably coupled with the lifting mechanism 52 or with the smart system, the controller comprising a processor operable by way of a set of executable instructions storable in relation to a memory, e.g., a non-transient memory device, set of executable instructions configuring the processor to instruct the components, as shown in FIG. 9, to performs various actions. At least one other power supply, such as at least one other battery, is configured to couple with the at least one interface 99 and to power the weighing mechanism 51, comprising the scale, for at least approximately 16 hours and to complete at least approximately 24 complete up/down cycles with an approximately 100-kg load, without requiring charging.

Figure 10A:
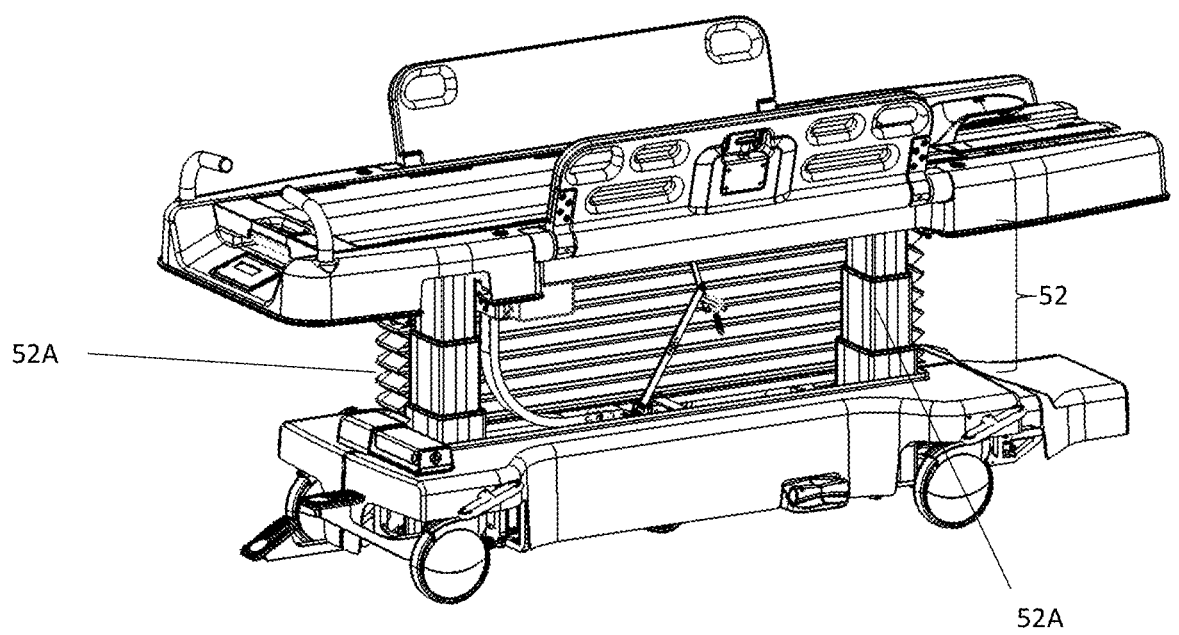
FIG. 10A is a diagram illustrating a perspective view of a medical transporter having a slidable bed, the transporter implementable with a smart system, comprising a weighing feature and an electromechanical elevator, in accordance with an embodiment of the present disclosure.

Referring to FIG. 10A, this diagram illustrates, in a perspective view, a medical transporter 100, the transporter 100 implementable with a smart system, comprising a weighing mechanism 51 and lifting mechanism 52, for controlling operation of a medical transporter 100, the lift mechanism 52 comprising at least one lift column 52a (FIG. 5), in accordance with an embodiment of the present disclosure. By example only, the at least one lift column 52a comprises an "LC1" lift columns from LINAK®. The at least one lift column 52a is configured to handle a push-load capacity in a range of up to approximately 4000 N and a pull-load capacity in a range of up to approximately 2000 N as well as comprise a safety factor of at least 2.5. The at least one lift column 52a comprises a stroke in a range of up to approximately 400 mm and a build-in dimensional of approximately 350 mm. The at least one lift column 52a comprises a dynamic bending moment in a range of up to approximately 350 N-m, a static bending moment in a range of up to approximately 500 N-m, and an ingress protection rating of "IPX4." IPX4 is a rating that offers protection against splashes of water, making them suitable for workouts or light rain.

Figure 10B:
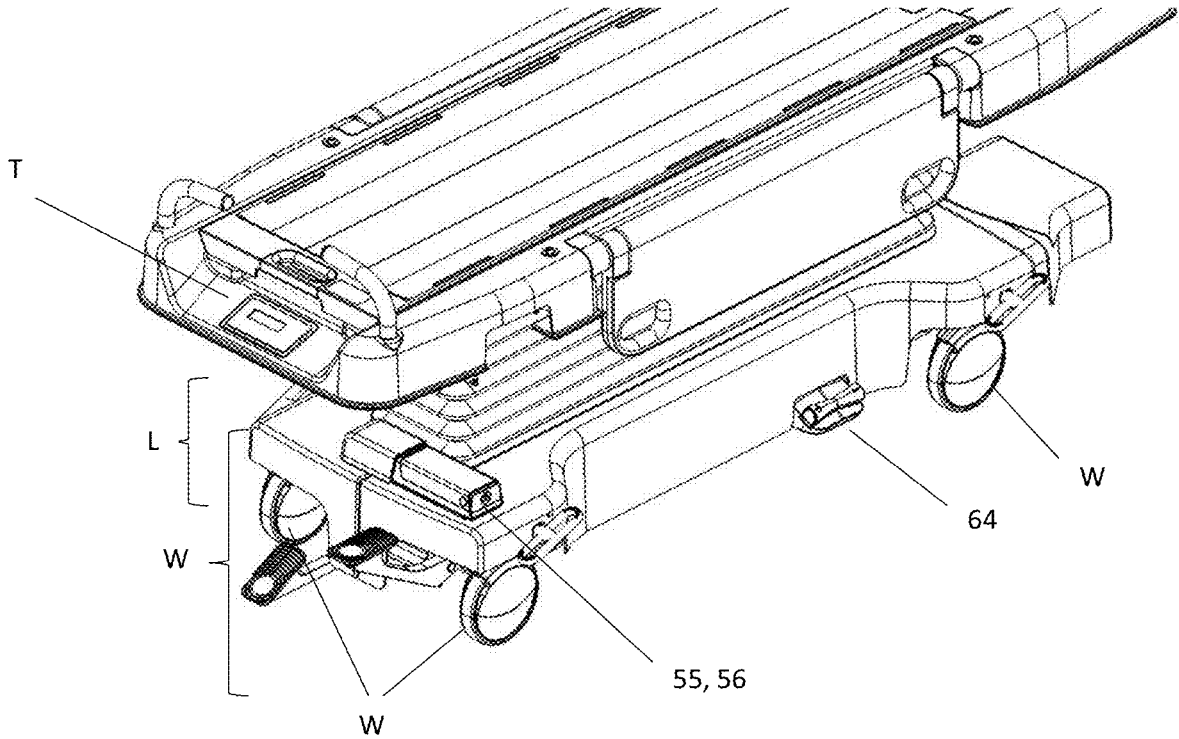
FIG. 10B is a diagram illustrating a cutaway perspective view of the medical transporter, as shown in FIG. 10A, the transporter implementable with a smart system, comprising a weighing mechanism and lifting mechanism, for controlling operation of a medical transporter, in accordance with an embodiment of the present disclosure.

Referring to FIG. 10B, this diagram illustrates, in a cutaway perspective view of the medical transporter, as shown in FIG. 10A, the transporter 100 implementable with the smart system, comprising a weighing mechanism 51 and lifting mechanism 52, for controlling operation of a medical transporter 100, the lift mechanism 52 further comprising at least one of a user interface, such as a user-facing control 64, e.g., a foot-switch, a power interface, a power supply, such as a battery 65, and a control feature 66, such as a control box, in accordance with an embodiment of the present disclosure.

Figure 10C:
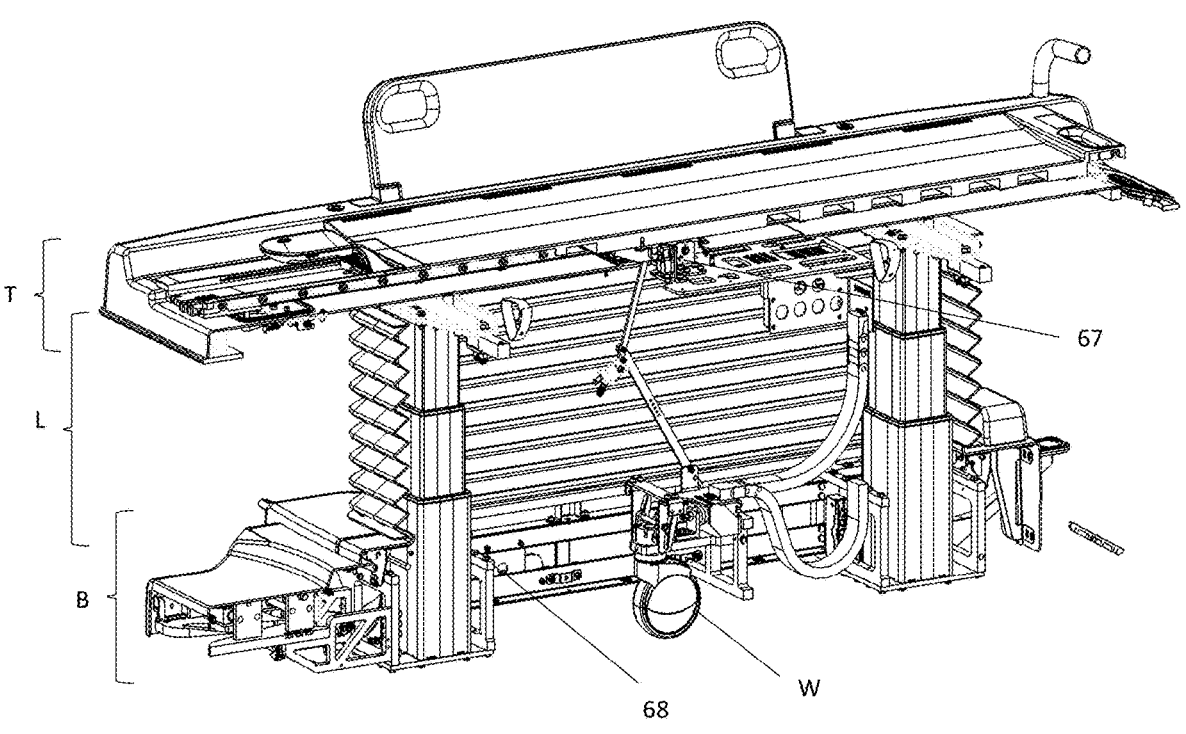
FIG. 10C is a diagram illustrating a perspective view of the medical transporter, as shown in FIG. 10A, the transporter implementable with a smart system, comprising a weighing mechanism and lifting mechanism, for controlling operation of a medical transporter, in accordance with an embodiment of the present disclosure.

Referring to FIG. 10C, this diagram illustrates, in a cutaway perspective view of the medical transporter 100, as shown in FIG. 10A, the transporter 100 implementable with the smart system, comprising a weighing mechanism 51 and lifting mechanism 52, for controlling operation of a medical transporter 100, the lift mechanism 52 further comprising at least one of a switch, such as a limit-switch 67, and a junction box 68, in accordance with an embodiment of the present disclosure.

Figure 10D:
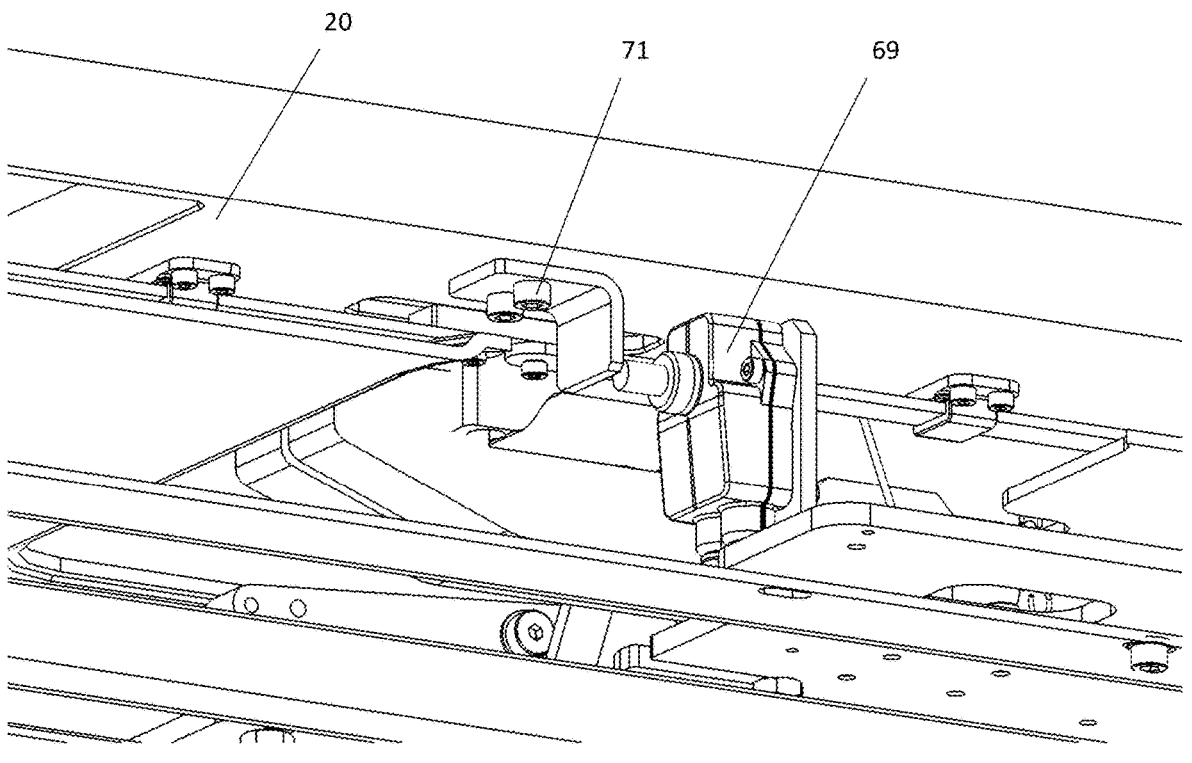
FIG. 10D is a diagram illustrating a cutaway perspective view of the medical transporter, as shown in FIG. 10A, the smart system further comprising a bed switch for an electromechanical bed actuator (not shown), in accordance with an embodiment of the present disclosure.

Referring to FIG. 10D, this diagram illustrates, in a cutaway perspective view of the medical transporter 100, as shown in FIG. 10A, the smart system further comprising a bed switch 69, such as a LINAK® SLS switch, for an electromechanical bed actuator (not shown), in accordance with an embodiment of the present disclosure. When the bed 20 is still in a retracted position, the L-angled bracket 71 coupled with the bed 20, e.g., on a lower surface of the bed 20, engages with the bed switch 69, thereby activating the bed switch 69, e.g., turning it "ON." The lift column 52*a* is, therefore, enabled when the bed 20 is in its retracted position. When the bed 20 moves forward to its extended position, an L-angled bracket 71, coupled with the bed 20, e.g., on a lower surface of the bed 20, disengages from the bed switch 69, thereby deactivating the bed switch 69, e.g., turning it "OFF." The lift column 52*a* is, therefore, disabled when the bed 20 is in its extended position.

Figure 10E:
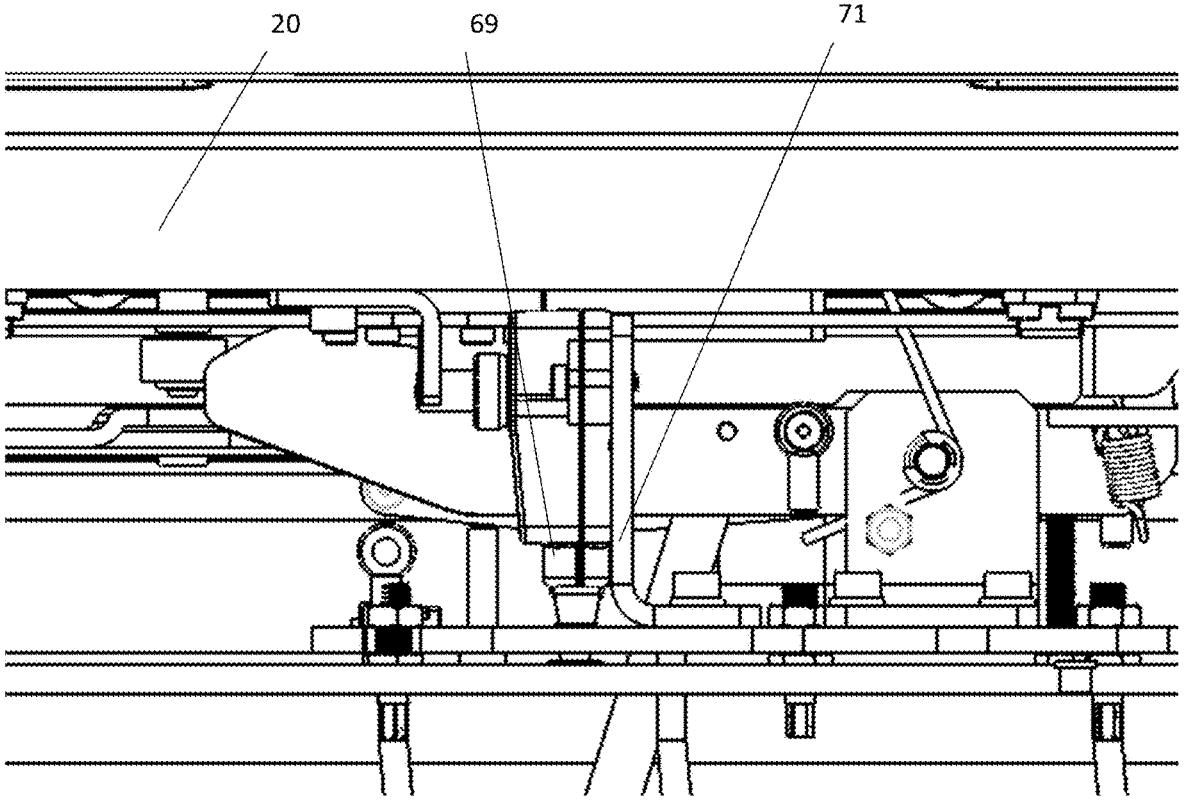
FIG. 10E is a diagram illustrating a cutaway side view of the medical transporter, as shown in FIG. 10D, wherein the bed switch is in an "ON" position when the bed is in a retracted position, such as an undeployed position, in accordance with an embodiment of the present disclosure.

Referring to FIG. 10E, this diagram illustrates, in a cutaway side view, the medical transporter 100, as shown in FIG. 10D, wherein the bed switch 69 is in an "ON" position when the bed 20 is in a retracted position, such as an undeployed position, for an electromechanical bed actuator (not shown), in accordance with an embodiment of the present disclosure. When the bed 20 is still in a retracted position, the L-angled bracket 71 coupled with the bed 20, e.g., on a lower surface of the bed 20, engages with the bed switch 69, thereby activating the bed switch 69, e.g., turning it "ON." The lift column 52*a* is, therefore, enabled when the bed 20 is in its retracted position.

Figure 10F:
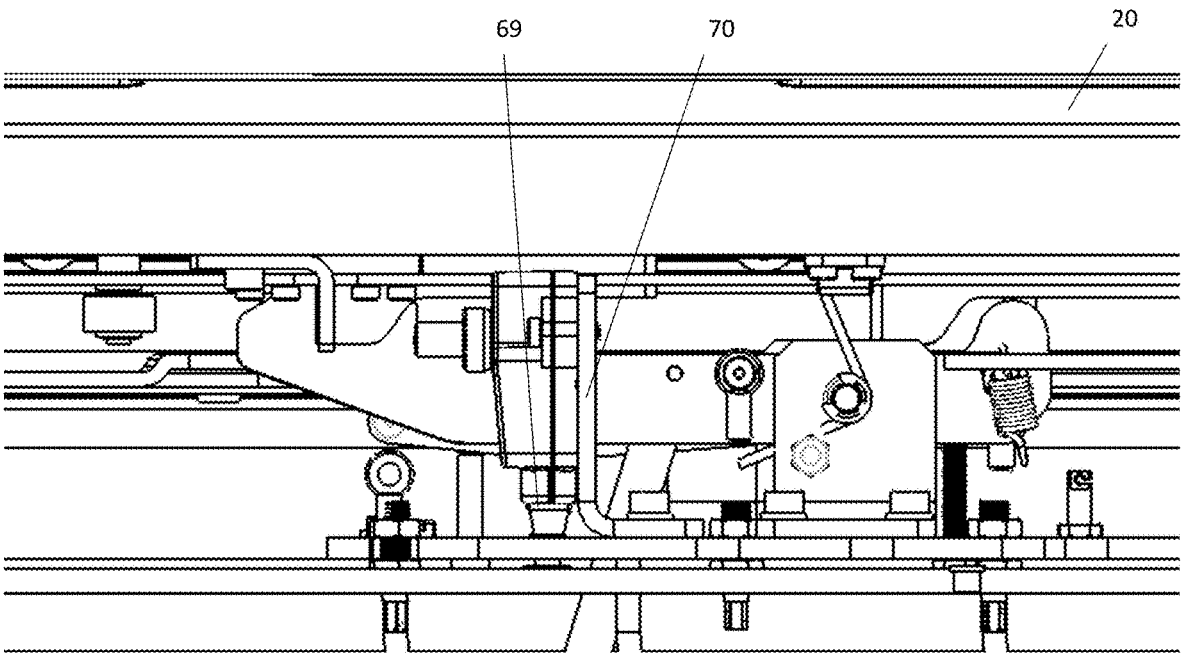
FIG. 10F is a diagram illustrating a cutaway side view of the medical transporter, as shown in FIG. 10D, wherein the bed switch is in an "OFF" position when the bed is in an extended position, such as deployed position, in accordance with an embodiment of the present disclosure.

Referring to FIG. 10F, this diagram illustrates, in a cutaway side view, the medical transporter 100, as shown in FIG. 10D, wherein the bed switch 69 is in an "OFF" position when the bed 20 is in an extended position, such as deployed position, for an electromechanical bed actuator (not shown), in accordance with an embodiment of the present disclosure. When the bed 20 moves forward to its extended position, the L-angled bracket 71, coupled with the bed 20, e.g., on a lower surface of the bed 20, disengages from the bed switch 69, thereby deactivating the bed switch 69, e.g., turning it "OFF." The lift column 52*a* is, therefore, disabled when the bed 20 is in its extended position.

Figure 11A:
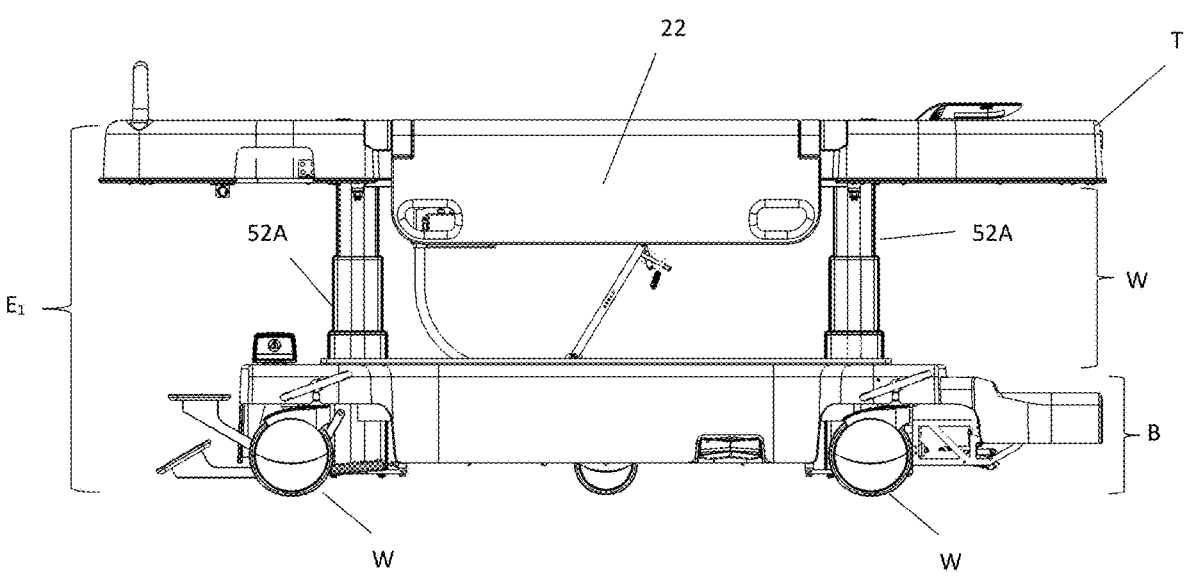
FIG. 11A is a diagram illustrating a side view of a medical transporter, implementable with a smart system, in accordance with an embodiment of the present disclosure.

Referring to FIG. 11A, this diagram illustrates, in a side view, a medical transporter 100, implementable with a smart system, wherein the bed 20 is disposed at an adjusted height, e.g., an adjusted height $E_2$, the adjusted elevation achieved by way of a lifting mechanism 52, comprising the lift column 52*a*, in accordance with an embodiment of the present disclosure. Elevation of the table T of the transporter 100, and, effectively that of the bed 20, is adjustable by the lifting mechanism 52. A highest elevation comprises a range of up to a scanning height $E_s$ as defined as an Acceptance Criteria in corresponding requirements. The highest elevation is adjustable by service personnel within a range of approximately 885 mm to approximately 900 mm above the floor elevation. The lift columns 52*a* comprise a maximum stroke of 400 mm; therefore, the transporter 100 has a maximum height well over 900 mm. The service handset (not shown) and memory (not shown) of the lifting mechanism 52 allows a trained operator to adjust and set the adjusted height $E_2$ of the lift columns 52*a* to match the scanning height $E_s$ of imaging apparatus I, e.g., as defined by a magnet (not shown) of an MRI machine (not shown). According to further embodiments of the disclosure, adjustment of the patient transported is configured and adjusted by the service team and not by users. The highest elevation (i.e. scanning height) is set by service during installation and checked at every preventive maintenance interval and is locked and is not changed by the user.

Still referring to FIG. 11A, a position of the bed 20 does not deviate by more than approximately 2 degrees during vertical displacement, e.g., during an elevation adjustment. The lift columns 52*a* are configured to synchronously operate even when the bed 20 is unevenly loaded, e.g., with the natural weight distribution of a patient P. The controller for the lifting mechanism 52 further comprises at least one encoder (not shown) configured to prohibit movement of the lifting columns 52*a*, wherein damage to the lifting mechanism 52 is prevented. To calibrate or re-calibrate the lifting mechanism 52, a "down" control button or other interface is pressed until the lift columns 52*a* fully retract. An audible beep indicates that calibration or re-calibration is complete and that the encoders are reset and properly functioning, whereby operating the lifting mechanism is immediately resumable. The force required for electrically operated functions comprises a range of less than approximately 5 N. The lift columns 52*a* are configured to operate at a speed in a range of up to approximately 0.1 m/s and an acceleration in a range of up to approximately 1.1 m/s². According to further embodiments of the disclosure, calibration and/or re-calibration of the system is also performed by the service team and not by the users. In the event of drift, the user can lower the bed all the way which will zero the encoders and correct for drift. The "calibration" (including the audible feedback) is only to set the scanning height of the bed and can only be done by service team.

Still referring to FIG. 11A, the lifting mechanism 52 is permitted to operate by the smart system only if all the following conditions are determined, by the smart system, to exist: (a) a continuous activation of a single lift mechanism control has occurred, (b) the bed 20 is retracted, and (c) the power supply is connected with sufficient charge. An SLS switch prevents any movement of the lift columns 52*a* unless the SLS switch is pressed. If the lifting mechanism 52 receives a plurality of commands, the lifting mechanism 52 is prohibited from responding to any command of the commands and is configured to stop vertical movement if the lift columns 52*a* are in motion; and the lifting mechanism 52 remains at a constant vertical position (elevation) until the plurality of commands is released and a new command is received. The controller is configured to stop motion of the lifting mechanism 52 in the presence of conflicting commands; and motion of the lifting mechanism 52 cannot resume until all input commands are released and a new command is received. When raised to the scanning height $E_s$, the transporter 100 is enabled for operation with the bed motion system.

Figure 11B:
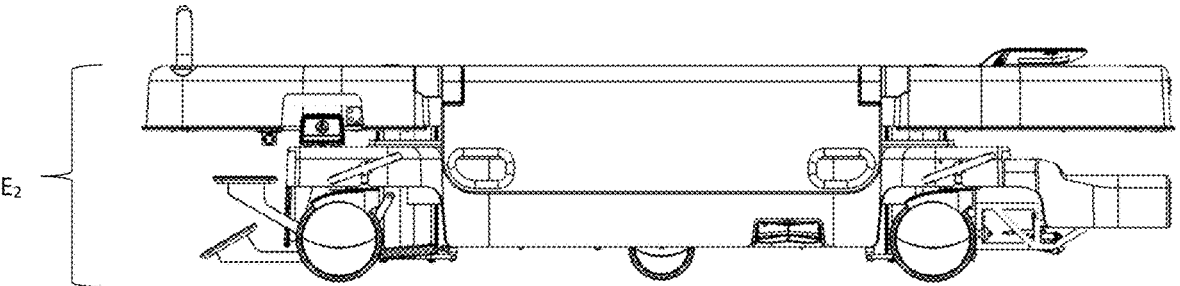
FIG. 11B is a diagram illustrating a side view of the medical transporter, as shown in FIG. 11A, wherein the bed is disposed at its original height, in accordance with an embodiment of the present disclosure.

Referring to FIG. 11B is a diagram illustrating a side view, the medical transporter, as shown in FIG. 11A, wherein the bed 20 is disposed at its original height $E_1$, in accordance with an embodiment of the present disclosure. Elevation of the table T of the transporter 100, and, effectively that of the bed 20, is adjustable by the lifting mechanism 52. A lowest elevation comprises a range of up to approximately 643 mm above a floor, e.g., of an imaging room. A floor elevation of the transporter 100, having the largest possible diameters, e.g., casters having a diameter of approximately 200 mm and comply with the industry standard for hospital beds (DIN EN 12531).

Figure 12:
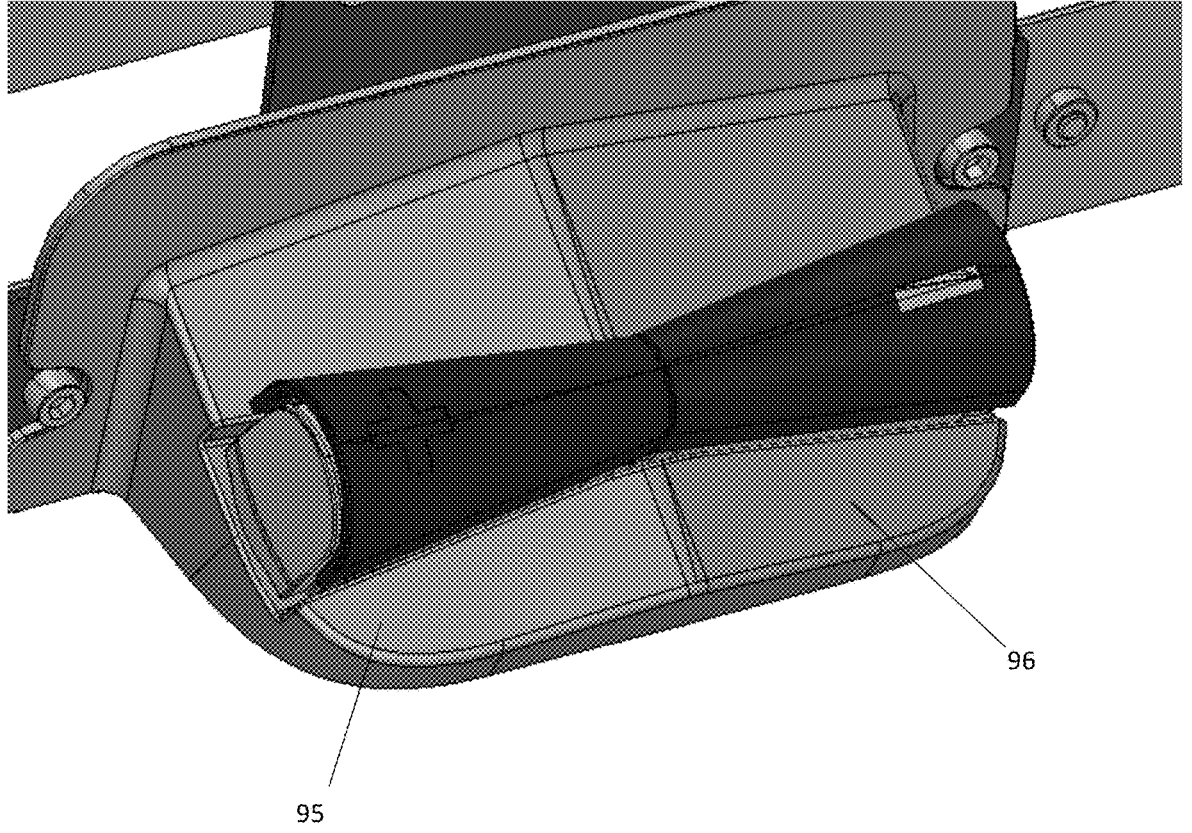
FIG. 12 is a diagram illustrating a perspective view of a user-facing lift control, such as a foot-switch, of a smart system, implementable with a medical transporter 100, in accordance with an embodiment of the present disclosure.

Referring to FIG. 12, this diagram illustrates, in a perspective view, a user-facing lift control, such as a foot-switch e.g., a left-hand lift foot-switch 95 and a right-hand lift foot switch 96, of a smart system (FIG. 9), implementable with a medical transporter 100, in accordance with an embodiment of the present disclosure. The foot-switches 95, 96 are configured to control elevation instruction to the lift columns 52a (i.e., raise or lower). The foot-switches 95, 96 comply with an IEC 60601-1 standard and may be constructed from a single moulded part.

Figure 13A:
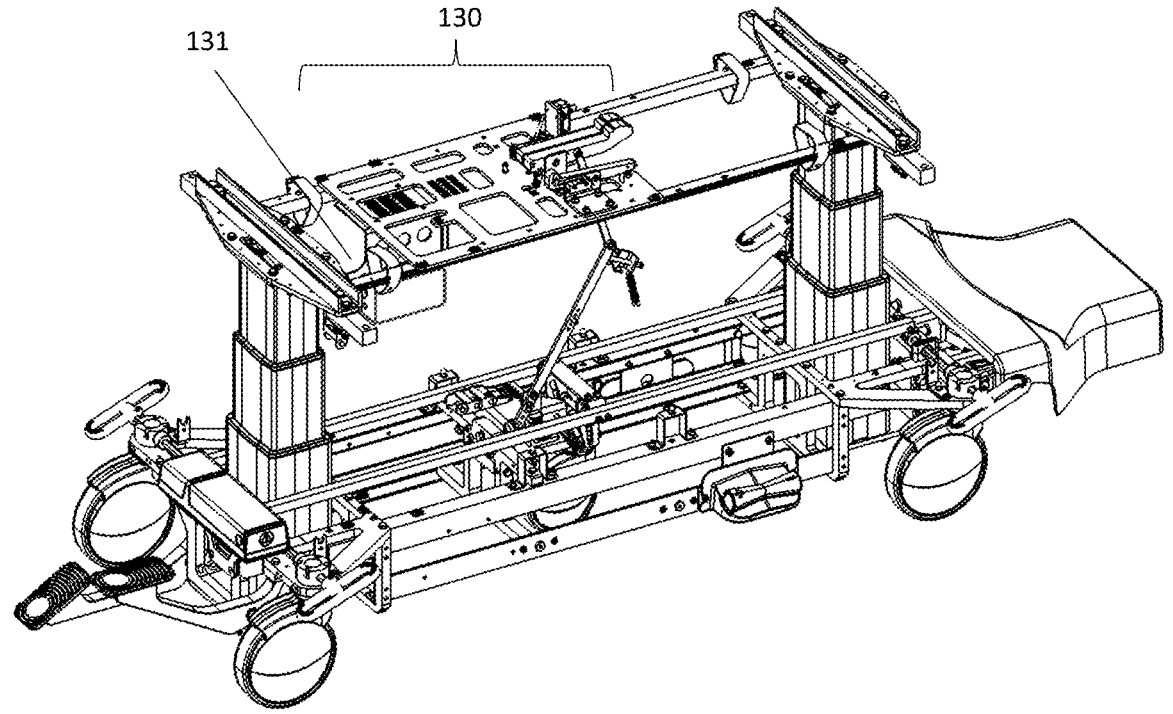
FIG. 13A is a diagram illustrating a perspective view of an interlock sub-assembly of a smart system, implementable with a medical transporter, in accordance with an embodiment of the present disclosure.

Referring to FIG. 13A, this diagram illustrates, in a perspective view, an interlock sub-assembly 130 of a smart system, implementable with a medical transporter 100, in accordance with an embodiment of the present disclosure. The interlock sub-assembly 130 comprises a plurality of components, at least some of which, are configured to couple with the table T of the transporter 100, e.g., in relation to an upper side thereof, as well as with the bed 20, e.g., in relation to a lower side thereof, for example. In fabricating the transporter 100, the plurality of components of the interlock sub-assembly 130 is configured to assemble, for instance, on a bench, prior to coupling the interlock sub-assembly 130 with the upper side of the table T and the lower side of the bed 20.

Referring to FIG. 13A, this diagram illustrates, in a closeup perspective view, an interlock sub-assembly 130 of a smart system, implementable with a medical transporter 100, as shown in FIG. 13A, in accordance with an embodiment of the present disclosure. The interlock sub-assembly 130 comprises at least one switch 132, at least one interlock arm 133, and at least one mounting bracket 134. A cable bracket (not shown) configured to couple with an interlock system is also configured to couple with a plate 131 of the interlock sub-assembly 130, e.g., is prior to coupling the interlock sub-assembly 130 with the table T of the transporter 100, e.g., in relation to an upper side thereof, as well as with the bed 20, e.g., in relation to a lower side thereof.

Figure 13B:
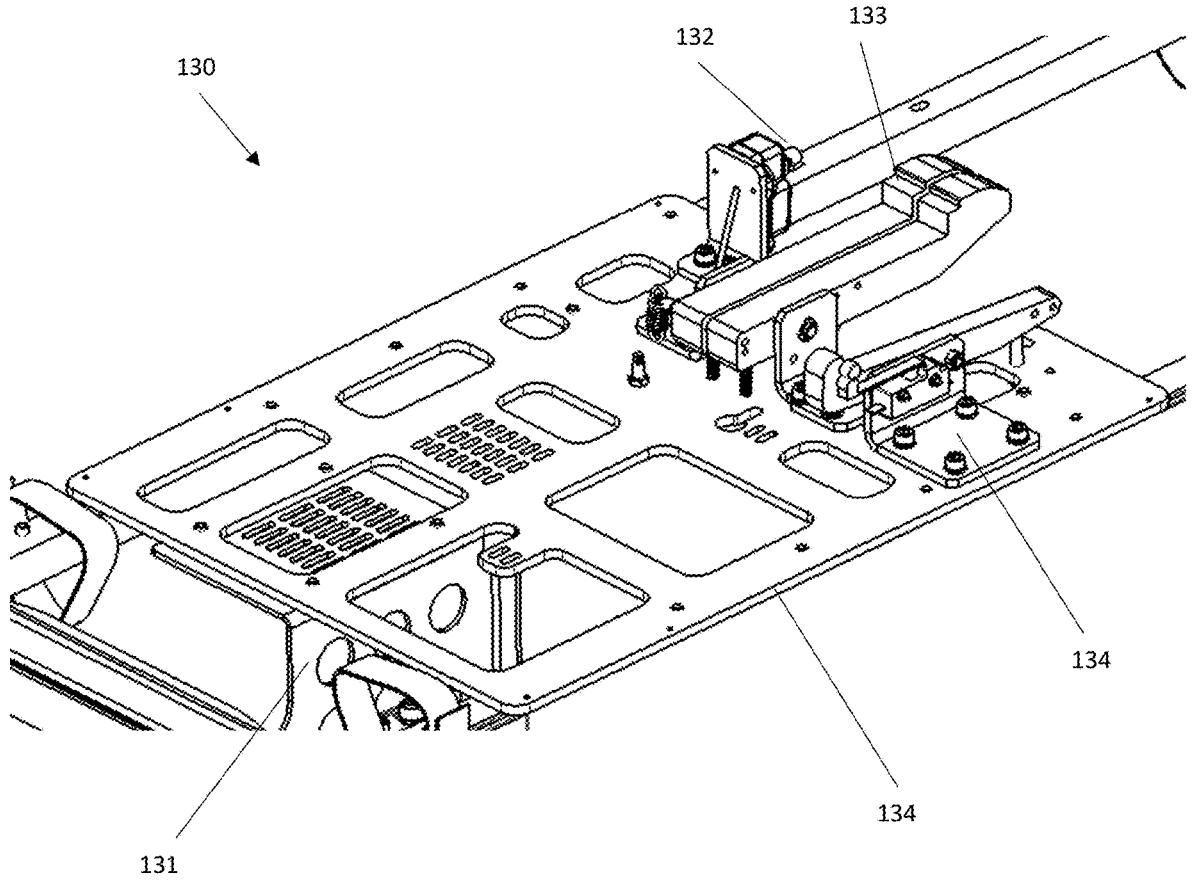
FIG. 13B is a diagram illustrating a closeup perspective view of an interlock sub assembly of a smart system, implementable with a medical transporter, as shown in FIG. 13A, in accordance with an embodiment of the present disclosure.
Figure 14:
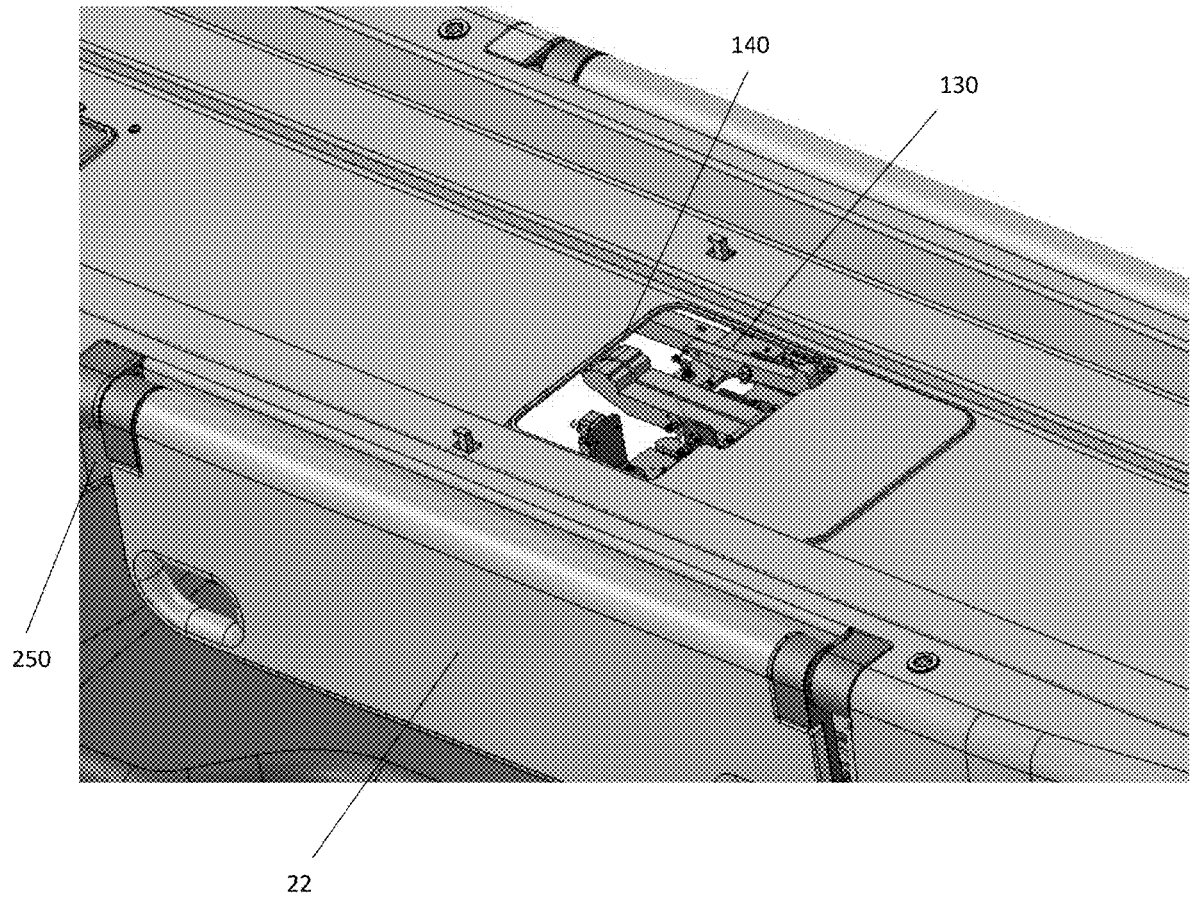
FIG. 14 is a diagram illustrating a closeup perspective view of a port for facilitating access to the interlock sub assembly, as shown in FIGS. 13A and 13B, such as for servicing thereof, in accordance with an embodiment of the present disclosure.

Referring to FIG. 14, this diagram illustrates, in a closeup perspective view, a port 140 for facilitating access to the interlock sub-assembly 130, as shown in FIGS. 13A and 13B, such as for servicing thereof, in accordance with an embodiment of the present disclosure. In fabrication, cable routing (not shown) is performed prior to assembly of enclosures. For service and adjustment, the interlock sub-assembly 130 is accessible via the port 140 of a top enclosure, e.g., an enclosure 250 (FIG. 25), after moving or removing the bed 20. The bed 20 comprises a mass in a range of up to approximately 20 kg, e.g., approximately one third that of related art beds in related art transporters. Thus, the bed 20 readily slides for accessing the port 140.

Figure 15:
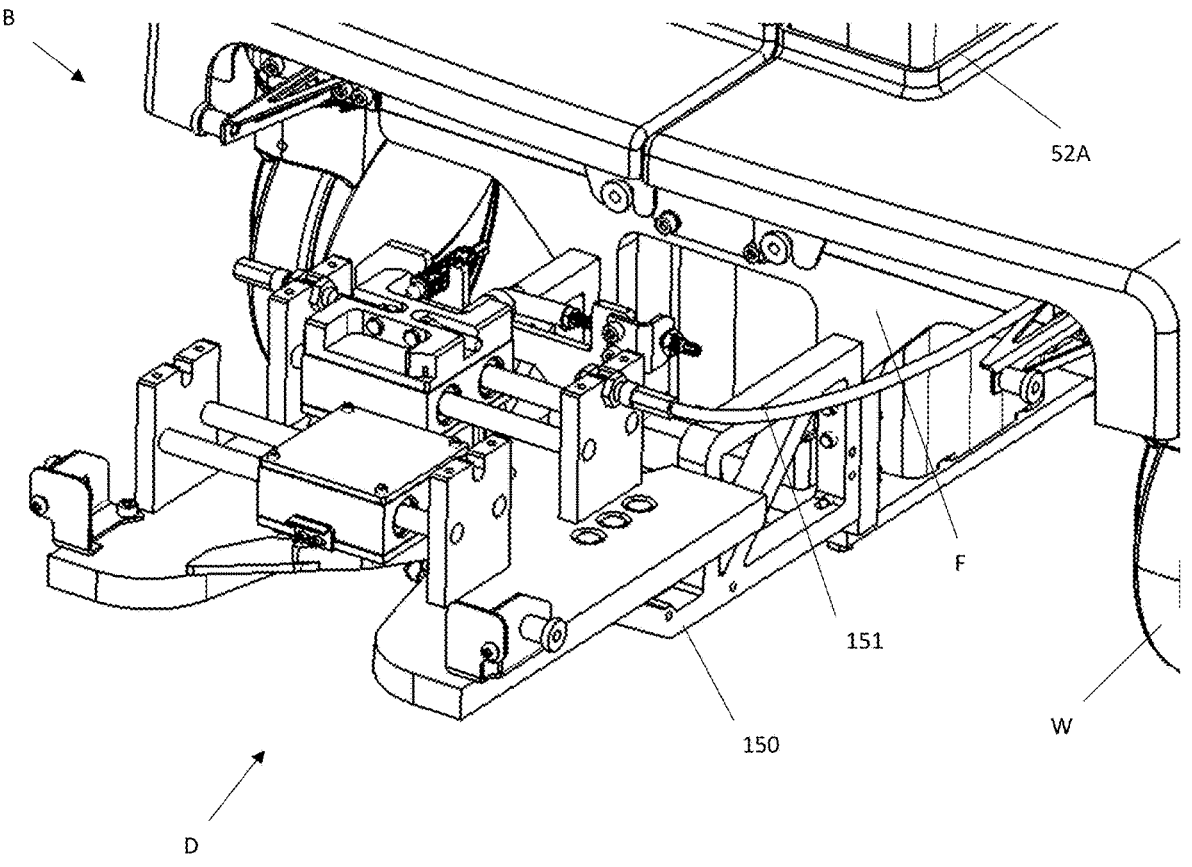
FIG. 15 is a diagram illustrating a cutaway perspective view of a cable, such as an interlock cable, for a docking module, of a smart system, implementable with a medical transporter, in accordance with an embodiment of the present disclosure.

Referring to FIG. 15, this diagram illustrates, in a cutaway perspective view, a cable 150, such as an interlock cable, for a docking module D, of a smart system, implementable with a medical transporter 100, wherein the cable is 150 routed to a base B of the transporter 100, in accordance with an embodiment of the present disclosure. The cable 150 comprises fittings that interface with the interlock inputs and outputs.

Figure 16:
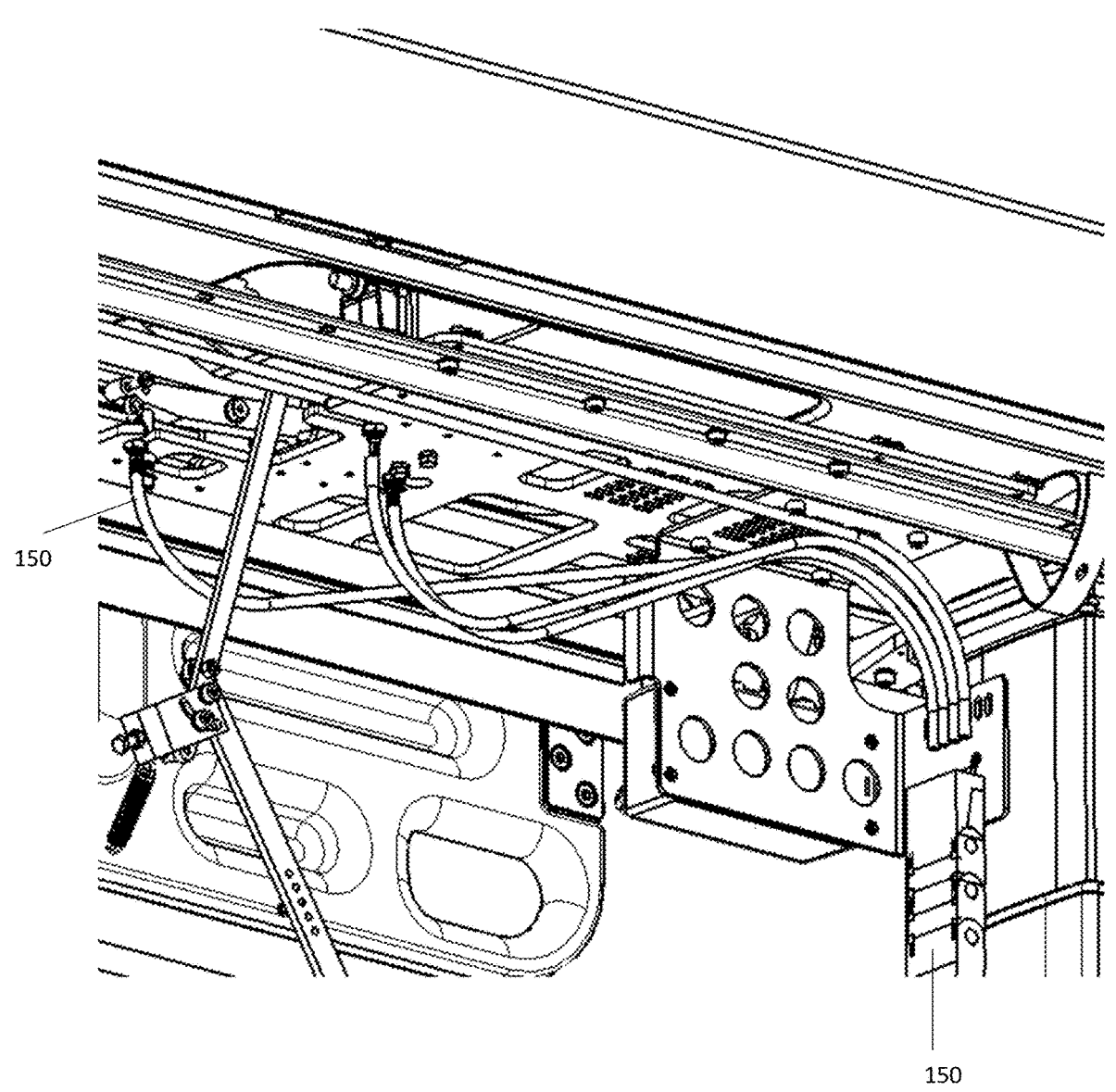
FIG. 16 is a diagram illustrating a cutaway closeup perspective view of a cable, such as an interlock cable, for a docking module, of a smart system, implementable with a medical transporter, in accordance with an embodiment of the present disclosure.

Referring to FIG. 16, this diagram illustrates, in a cutaway closeup perspective view, a cable 150, such as an interlock cable, for a docking module D, of a smart system, implementable with a medical transporter 100, wherein the cable is 150 routed to a base B of the transporter 100, in accordance with an embodiment of the present disclosure. The cable 150 is routable through the frame F, a cable chain 151, and positioned proximate an input/output.

Figure 17A:
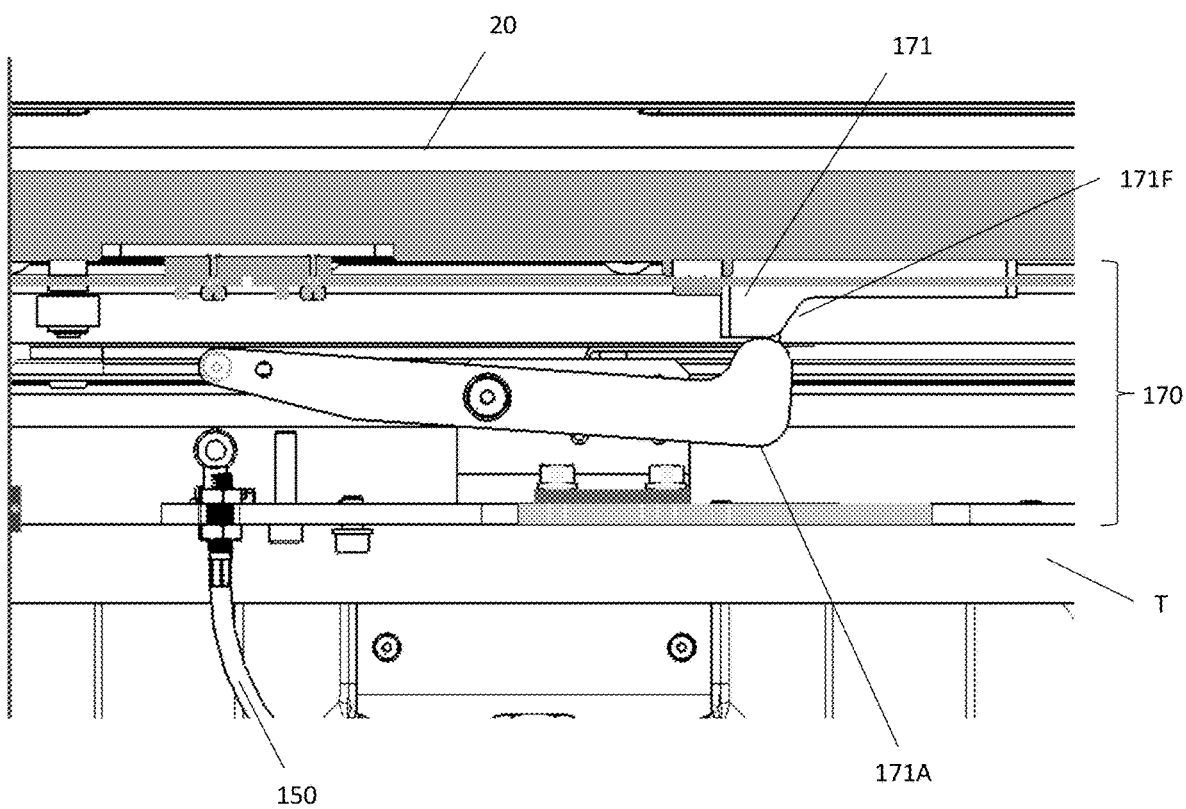
FIG. 17A is a diagram illustrating a cutaway side view of a bed-dock interlock operable with a docking module, in accordance with an embodiment of the present disclosure.

Referring to FIG. 17A, this diagram illustrates, in a cutaway side view, a bed-dock interlock 170, comprising an interlock arm 171a, the bed-dock interlock 170 operable with a docking module D of a smart system and implementable with the medical transporter 100, wherein a tension is applied to a cable 150, wherein the cable 150 is pulled upward, wherein a plunger is retracted to permit undocking of the transporter 100, and wherein a bed 20 is in a retracted position, in accordance with an embodiment of the present disclosure. By default, undocking of the transporter 100 from an imaging apparatus I is prevented unless the bed 20 is fully retracted.

Figure 17B:
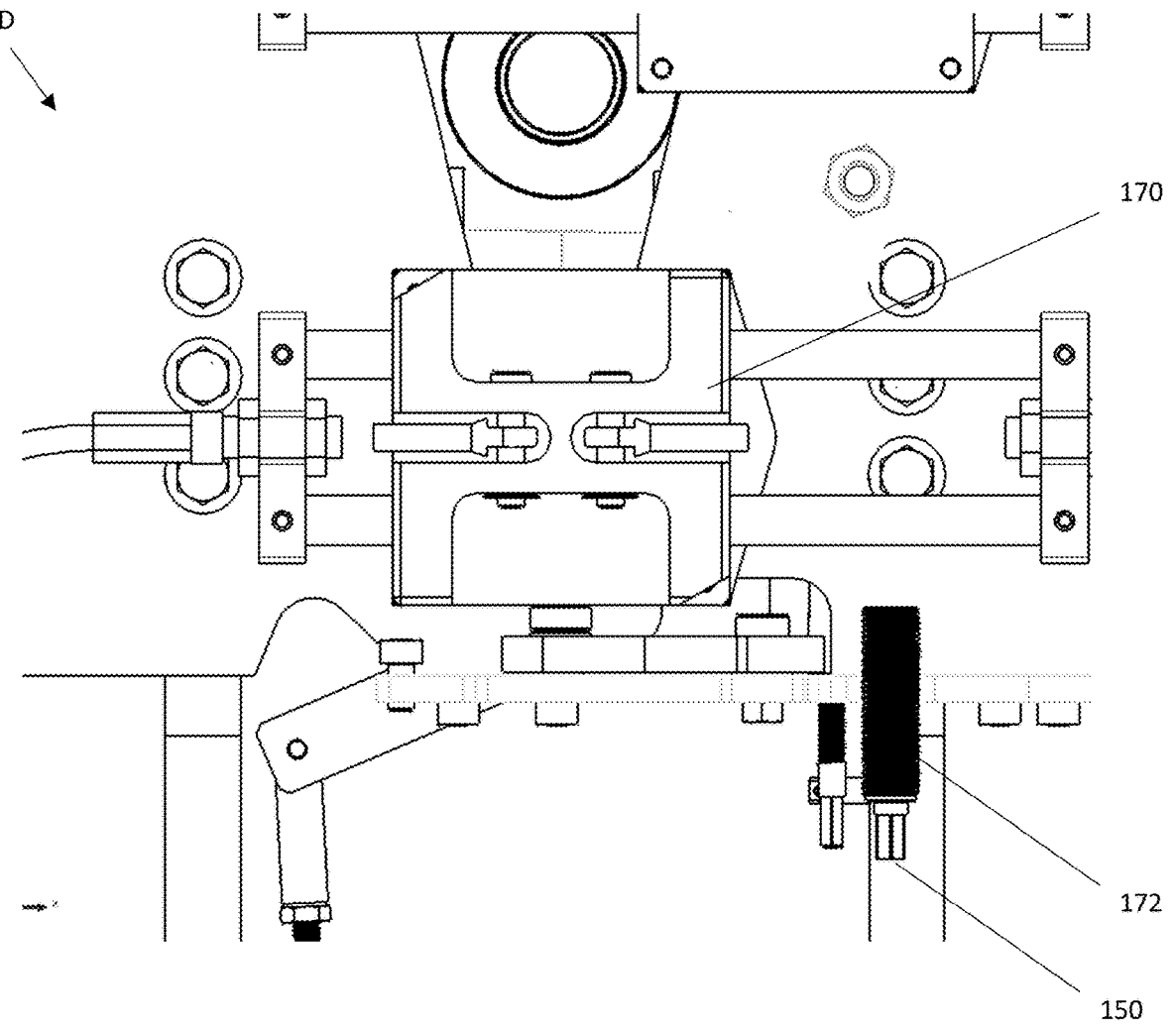
FIG. 17B is a diagram illustrating a plan view of the docking module operable with the bed-dock interlock, as shown in FIG. 17A, in accordance with an embodiment of the present disclosure.

Referring to FIG. 17B, this diagram illustrates, in a plan view, the docking module D of a smart system, operable with the bed-dock interlock 170, as shown in FIG. 17A, wherein the tension is applied to the cable 150, wherein the cable 150 is pulled upward, wherein the plunger (not shown) is retracted to permit undocking of the transporter 100, and wherein the bed 20 is in a retracted position, in accordance with an embodiment of the present disclosure. When the bed 20 is in its retracted position, the bed-dock interlock arm 170a is pushed downward by a face 171f of a stopper block 171, which causes the cable 150 to be pulled upward, whereby a plunger at the dock module D (FIG. 15) retracts inward, thereby permitting a sliding block 227 (FIG. 23A) to move freely for unlatching the bed 20 and undocking the transporter 100.

Figure 17C:
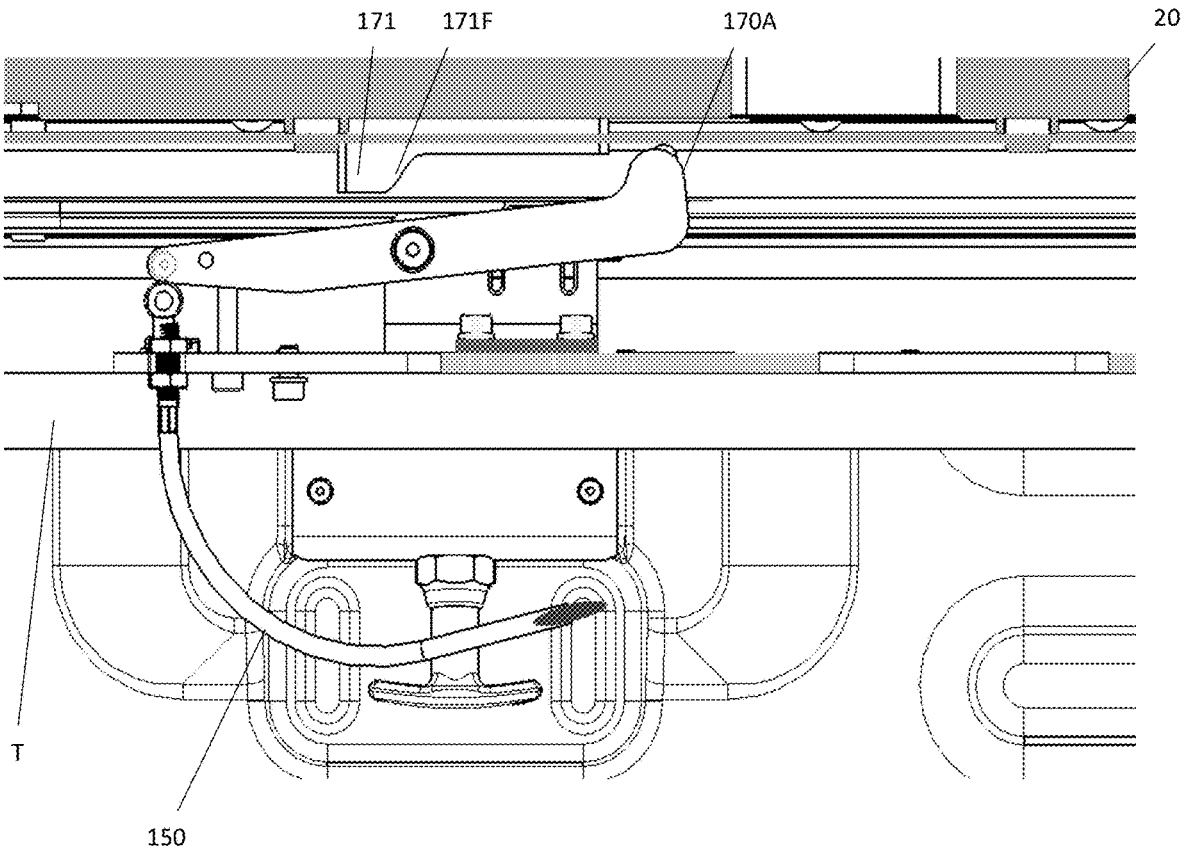
FIG. 17C is a diagram illustrating a cutaway side view of the bed-dock interlock operable with a docking module, as shown in FIG. 17A, in accordance with an embodiment of the present disclosure.

Referring to FIG. 17C, this diagram illustrates, in a cutaway side view, the bed-dock interlock 170, comprising an interlock arm 170a, the bed-dock interlock 170 operable with a docking module D, as shown in FIG. 17A, wherein the tension is released from the cable 150, wherein the plunger (not shown) is extended to prevent undocking of the transporter 100, and wherein the bed 20 is in an extended position, in accordance with an embodiment of the present disclosure. When the bed 20 is in its extended position, the bed-dock interlock arm 170a becomes disengaged with the face 171f of the stopper block 171 and moves to a parallel/relaxed position, thereby releasing the tension in the cable 150 which will cause the compression spring (not shown) in a plunger mechanism (not shown) to extend, thereby locking against the face 171f of the stopper block 171 and preventing the transporter 100 from undocking. More specifically, the spring in the plunger will always be extended which will prevent undocking, unless the bed 20 is fully retracted and the cable 150 is pulled back on the plunger mechanism, thereby compressing the spring thereof.

Figure 17D:
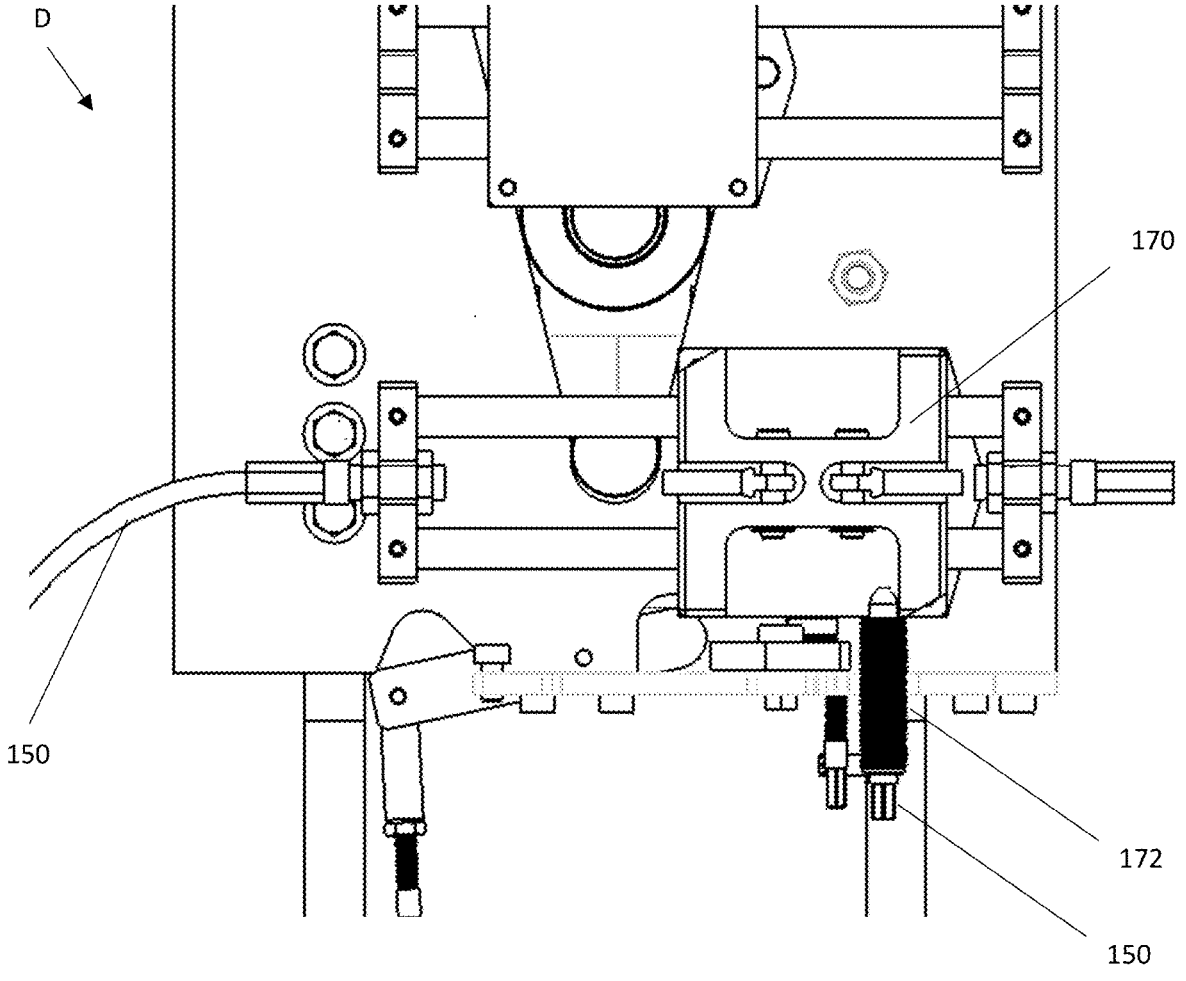
FIG. 17D is a diagram illustrating a plan view of the docking module operable with the bed-dock interlock, as shown in FIG. 17, in accordance with an embodiment of the present disclosure.

Referring to FIG. 17D, this diagram illustrates, in a plan view, the docking module D operable with the bed-dock interlock 170, as shown in FIG. 17B, wherein the tension is released from the cable 150, wherein the plunger 172 is extended to prevent undocking of the transporter 100, and wherein the bed 20 is in an extended position, in accordance with an embodiment of the present disclosure.

Figure 18A:
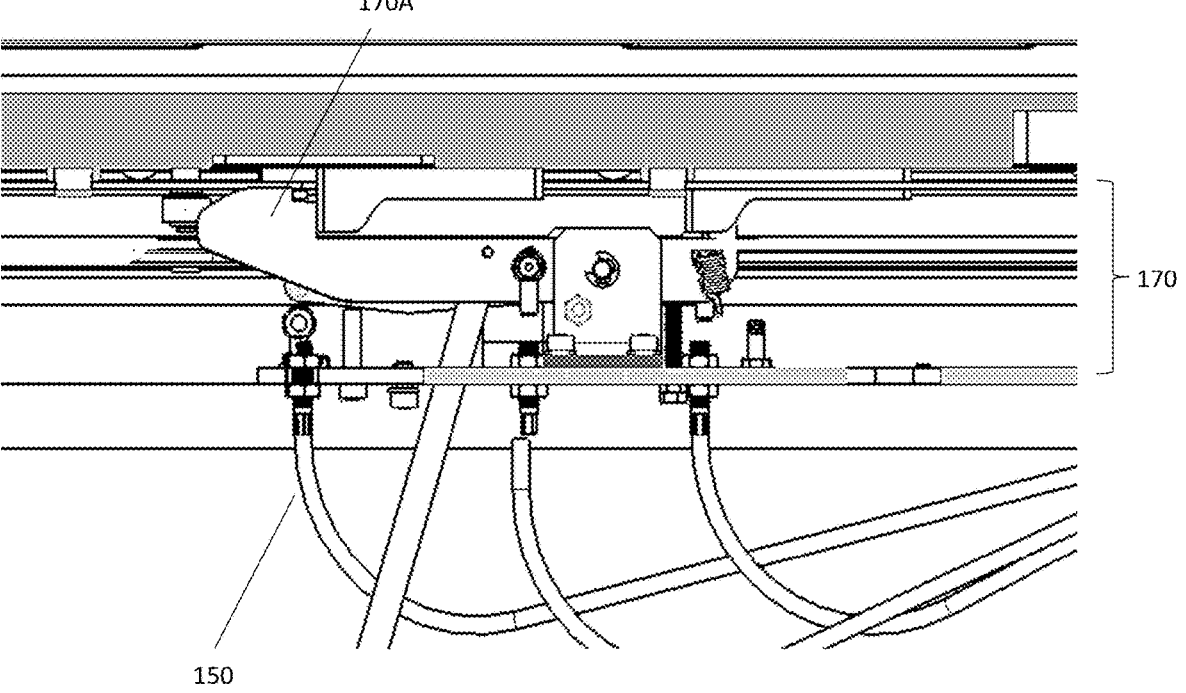
FIG. 18A is a diagram illustrating a cutaway side view of the dock-bed top interlock operable with a docking module, in accordance with an embodiment of the present disclosure.

Referring to FIG. 18A, this diagram illustrates, in a cutaway side view, the dock-bed interlock 170, comprising an interlock arm 170a, the bed-dock interlock 170 operable with a docking module D, as shown in FIG. 17C, wherein a tension is released from the cable 150, wherein a lever of the interlock sub-assembly 130 (as shown in FIG. 13A) is disengaged, such as by way of a primary spring, to lock the interlock sub-assembly 130, and wherein the bed 20 is prevented from extending in relation to the table T, in accordance with an embodiment of the present disclosure. The smart system prevents extension of the bed 20 beyond a boundary defined by the base B (bed 20 remains fully retracted) when the transporter 100 is undocked, even when the transporter 100 is disposed over an approximately 10-mm threshold.

Figure 18B:
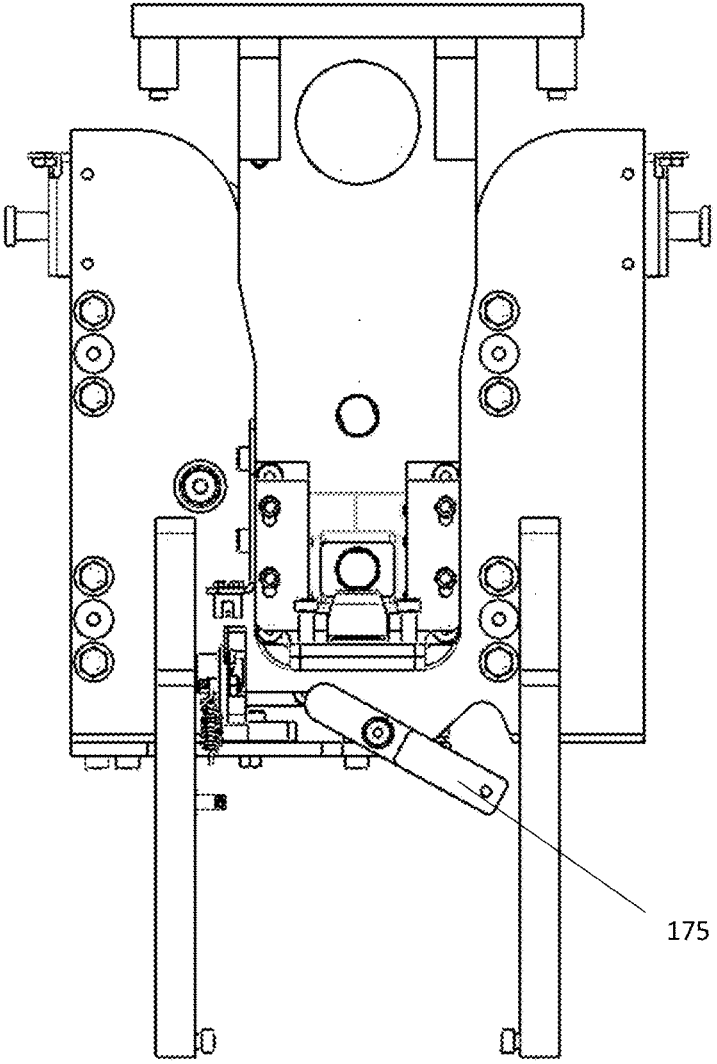
FIG. 18B is a diagram illustrating a plan view of the docking module operable with the dock-bed top interlock, as shown in FIG. 18A, in accordance with an embodiment of the present disclosure.

Referring to FIG. 18B, this diagram illustrates, in a plan view, the docking module D operable with the bed-dock interlock 170, as shown in FIG. 1D, wherein a lever 175 of the interlock sub-assembly 130 is disengaged, such as by way of a primary spring, to lock the interlock sub-assembly 130, and wherein the bed 20 is prevented from extending in relation to the table T, in accordance with an embodiment of the present disclosure. When the transporter 100 is undocked, the lever 175 at the base of the docking module D is in a relaxed and disengaged state. The extension spring at an end of one of the interlock arms 170a retracts by default to its free length and causes such interlock arm 170a to remain in a locked and parallel configuration as such interlock arm locks against the stopper block 171 to prevent the bed 20 from extending.

Figure 18C:
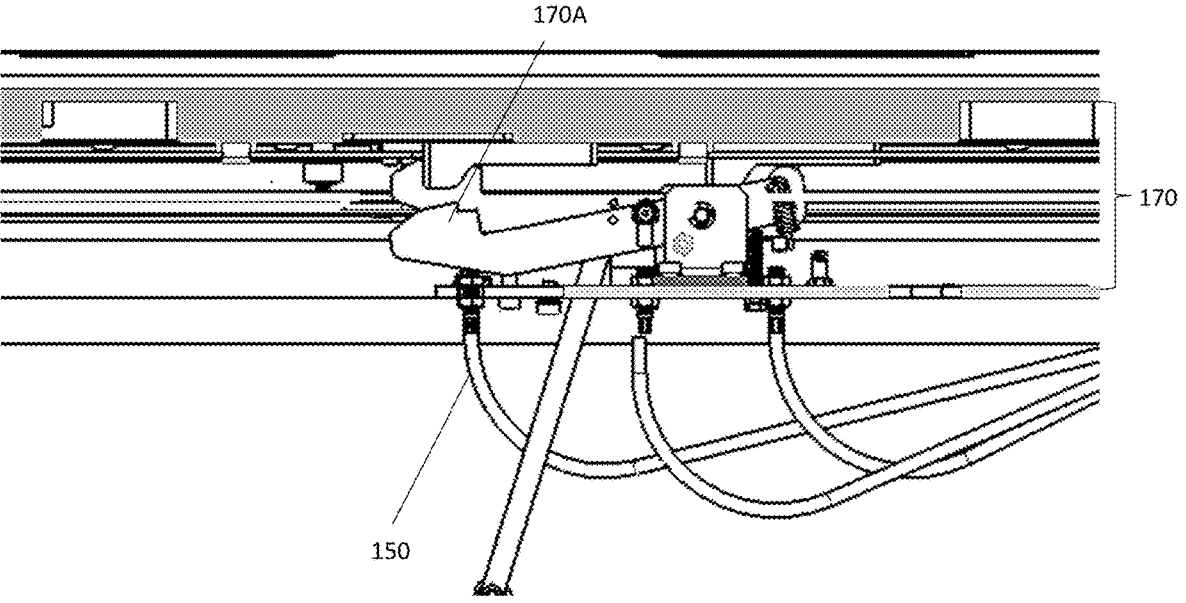
FIG. 18C is a diagram illustrating a cutaway side view of the dock-bed top interlock operable with a docking module, as shown in FIG. 18A, in accordance with an embodiment of the present disclosure.

Referring to FIG. 18C, this diagram illustrates, in a cutaway side view, the bed-dock interlock 170, comprising an interlock arm 170a, the bed-dock interlock 170 operable with a docking module D, as shown in FIG. 18A, wherein the tension is applied to the cable 150, wherein the lever 175 of an interlock sub-assembly 130 is engaged, such as by way of a primary spring (not shown), wherein an interlock arm 170a is pulled to unlock the interlock sub-assembly 130, wherein the bed 20 is permitted to extend in relation to the table T, and wherein the transporter 100 is dockable, in accordance with an embodiment of the present disclosure.

Figure 18D:
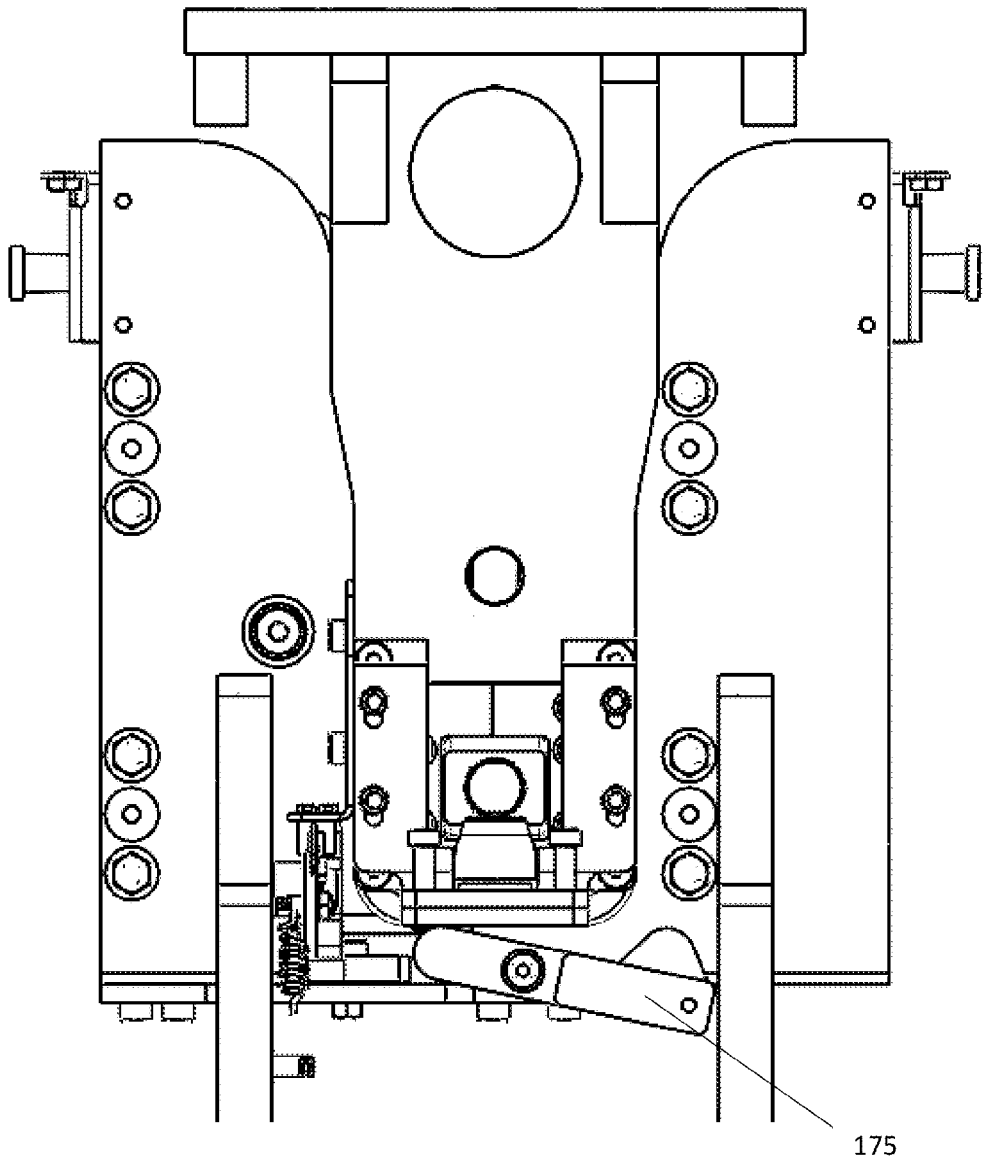
FIG. 18D is a diagram illustrating a plan view of the docking module operable with the dock-bed top interlock, as shown in FIG. 18A, in accordance with an embodiment of the present disclosure.

Referring to FIG. 18D, this diagram illustrates, in a plan view, the docking module D operable with the bed-dock interlock 170, as shown in FIGS. 18B, wherein the tension is applied to the cable 150, wherein the lever 175 of an interlock sub-assembly 130 is engaged, such as by way of a primary spring (not shown), wherein an interlock arm 170a is pulled to unlock the interlock sub-assembly 130, wherein the bed 20 is permitted to extend in relation to the table T, and wherein the transporter 100 is dockable, in accordance with an embodiment of the present disclosure. When the transporter 100 is docked and the scanner side of the docking module D pushes against the lever 175, the other end of the lever 175 pulls on the cable 150, thereby causing the interlock arm 170A to be pulled downward against the extension spring action, and thereby releasing the bed 20 and allowing it to extend.

Figure 19A:
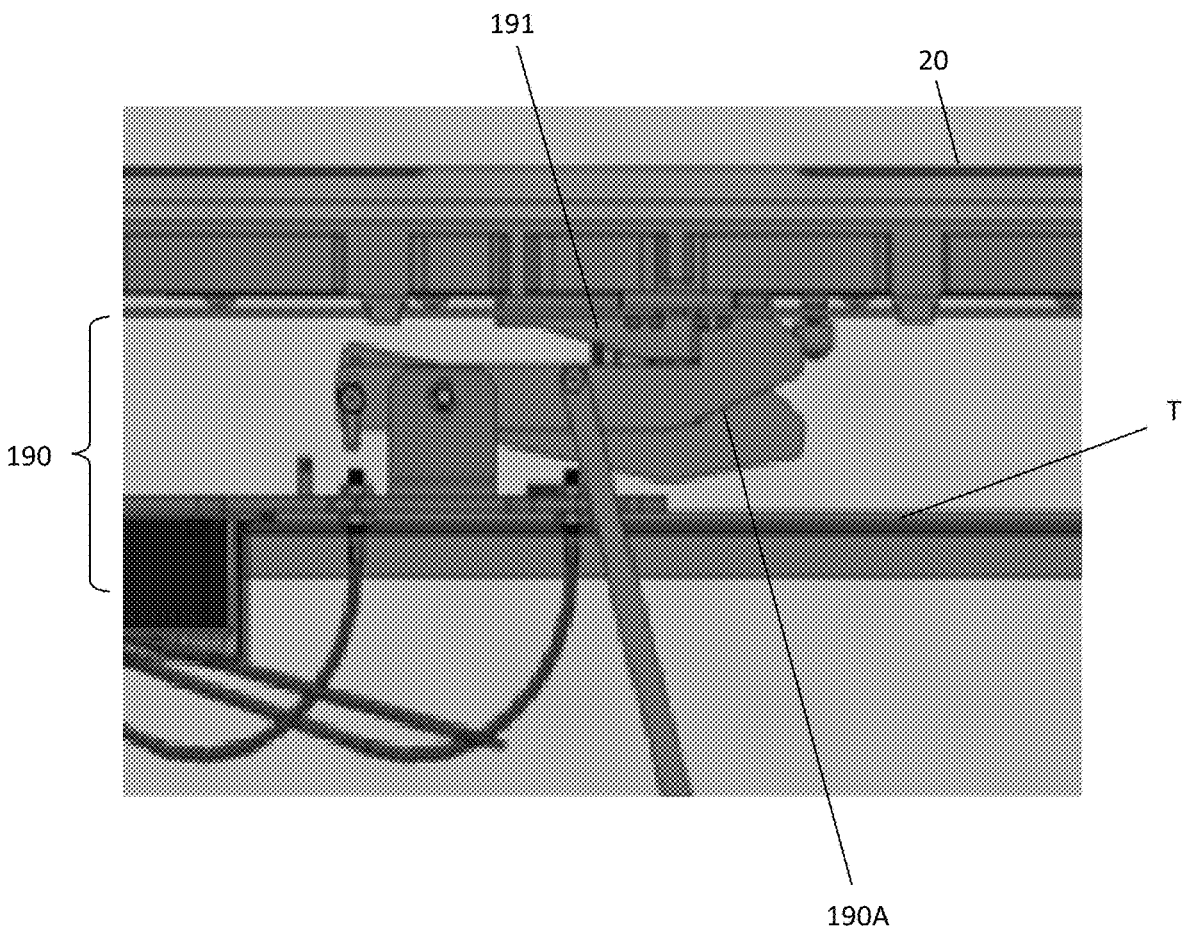
FIG. 19A is a diagram illustrating a cutaway side view of a height-bed interlock operable with the docking module, in accordance with an embodiment of the present disclosure.

Referring to FIG. 19A, this diagram illustrates, in a cutaway side view, a height-bed interlock 190, comprising an interlock arm 190a, the height-bed interlock 190 operable with a docking module D of a smart system (which may also operate independently of the dock), implementable with the medical transporter 100, wherein, when the bed 20 is disposed below the scanning height $E_s$, the interlock arm 190a engages with a stopper block 191 to prohibit extending the bed 20, in accordance with an embodiment of the present disclosure. The smart system for the transporter 100, by default, prevents the bed 20 from extending, except when the elevation of the bed 20 is at a scanning position. The height-bed interlock 190 is configured, such that, at below the scanning height $E_s$, the interlock arm 190 is pushed upward into a parallel position and engages with the stopper block 191 to prevent the bed 20 from extending. At the scanning height $E_s$, the interlock arm 190a is pulled downward, thereby releasing the bed 20 and allowing the bed 20 to extend.

Figure 19B:
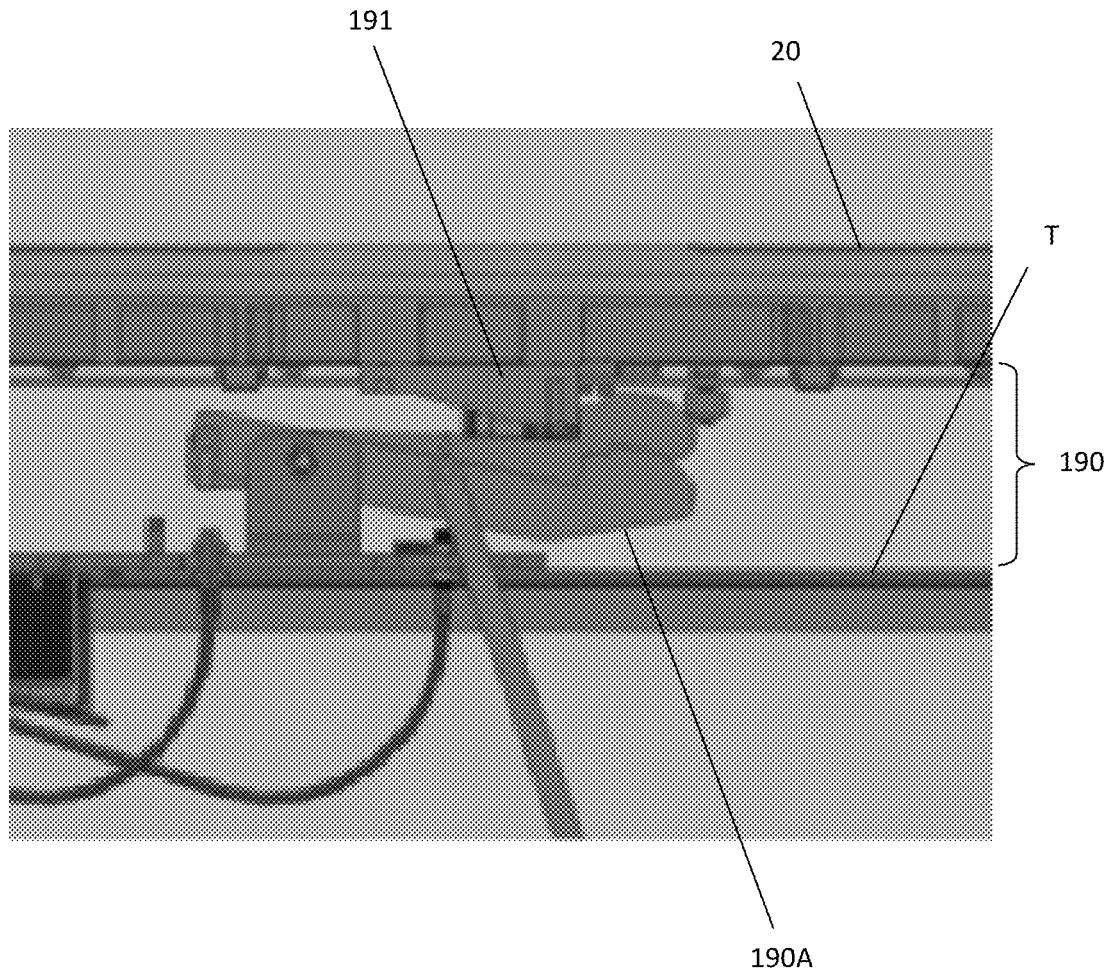
FIG. 19B is a diagram illustrating a cutaway side view of the height-bed interlock operable with the docking module, as shown in FIG. 19A, in accordance with an embodiment of the present disclosure.

Referring to FIG. 19B, this diagram illustrates, in a cutaway side view, the height-bed interlock 190, comprising an interlock arm 190a, the height-bed interlock 190 operable with a docking module D of the smart system, implementable with the medical transporter 100, as shown in FIG. 19A, wherein, when the bed 20 is at the scanning height $E_s$, the interlock arm 190a disengages with a stopper block 191 to permit extending the bed 20, in accordance with an embodiment of the present disclosure.

Figure 20A:
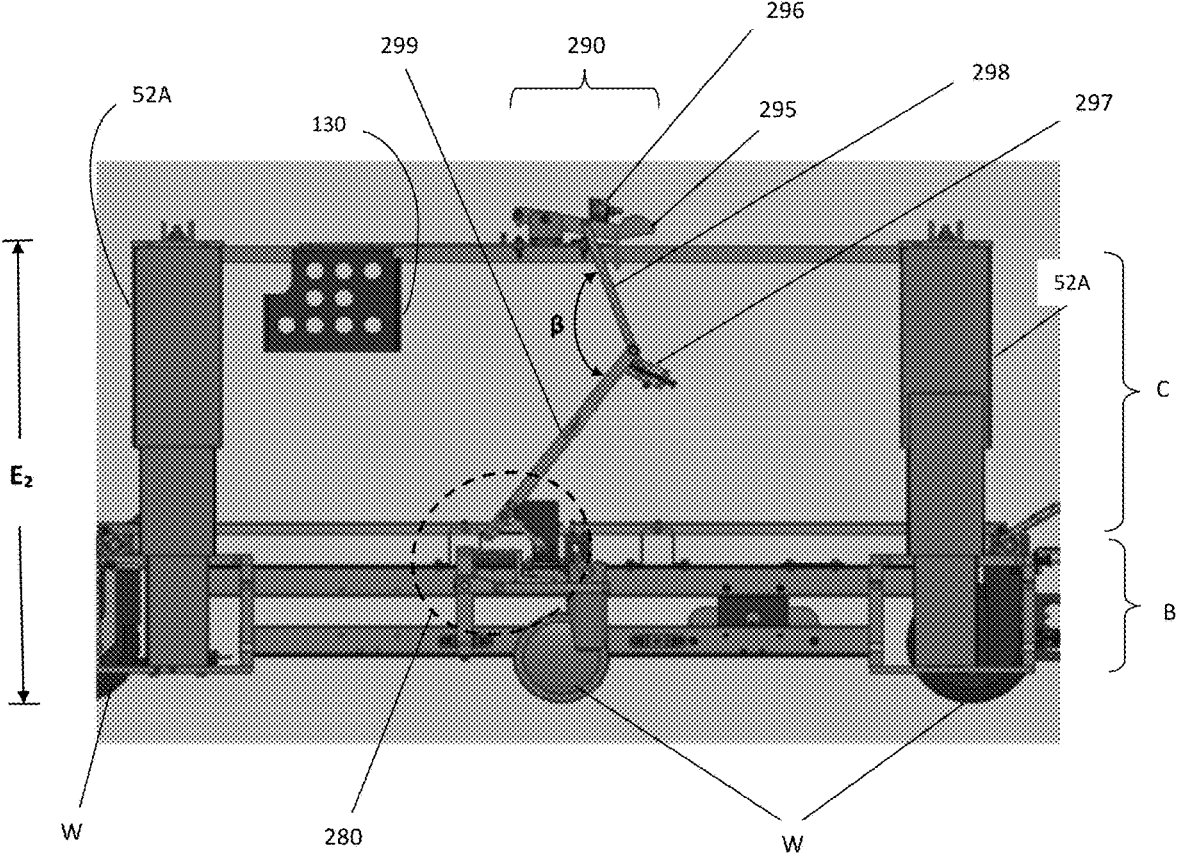
FIG. 20A is a diagram illustrating a cutaway side view of a medical transporter, implemented with a smart system, the smart system comprising a docking system, the docking system, a latching system, a weighing system, and a lifting system, in accordance with an embodiment of the present disclosure.
Figure 20B:
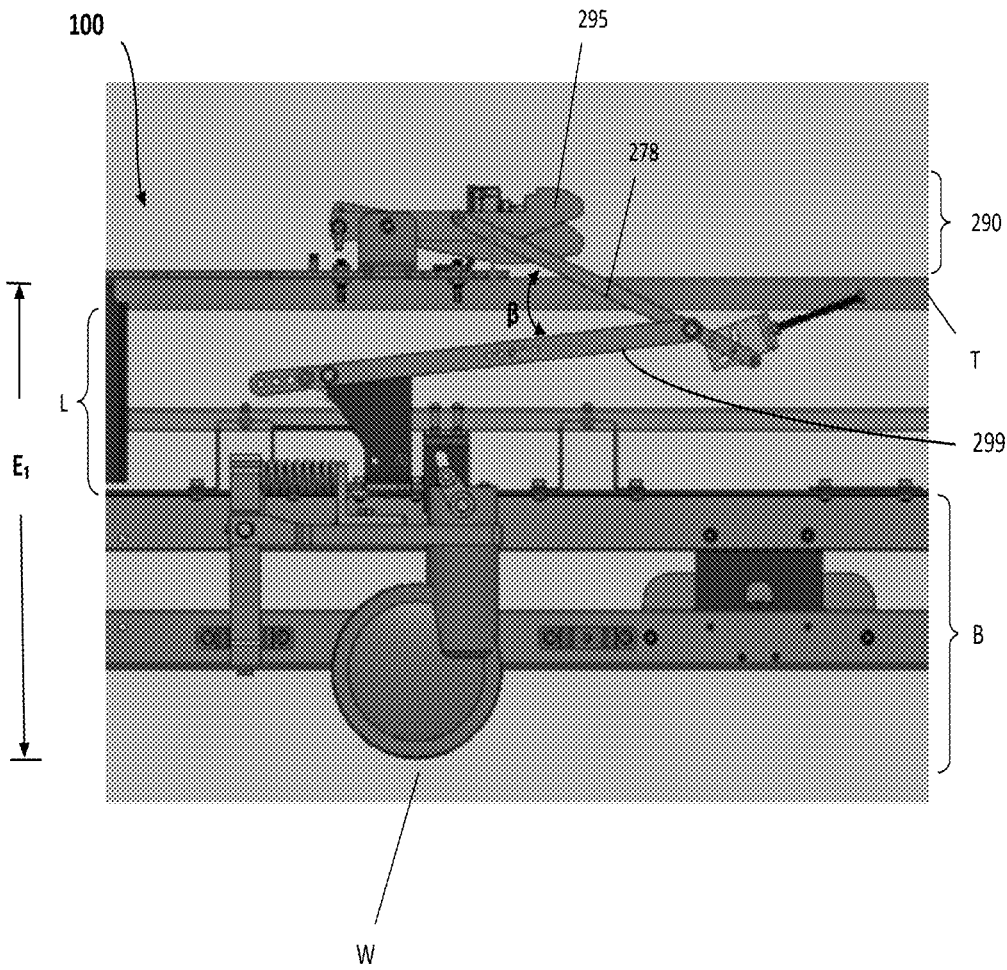
FIG. 20B is a diagram illustrating a cutaway side view of the medical transporter, as shown in FIG. 20A, implemented with a smart system, the smart system comprising a docking system, the docking system, a latching system, a weighing system, and a lifting system, accordance with an embodiment of the present disclosure.

According to the disclosure, FIGS. 20A and 20B show the height-bed interlock input. Wherein the linkages shown actuates the height-bed interlock lever (295 or 190A in FIGS. 19A and 19B). Referring to FIG. 20A, this diagram illustrates, in a cutaway side view, a medical transporter 100 the implemented with a smart system, the smart system comprising a docking system, the docking system comprising a docking module D, a latching system, the latching system comprising a latching mechanism, a weighing system, the weighing system comprising a weighing mechanism 51, and a lifting system, the lifting system comprising a lifting mechanism 52, the latching system comprising a plurality of interlocks, in accordance with an embodiment of the present disclosure. The pluralist of interlocks comprising at least a height-bed interlock 290. When the bed 20 is disposed at a scanning height $E_s$, or approximately e.g., =/–10 mm from the scanning height $E_s$, the interlock arm 295 (or 190A) disengages with a stopper block 296 to permit extending the bed 20 in relation to the table T, and wherein the smart system further comprises an adjustable braking mechanism 297. For example, the smart system further comprises a height-bed interlock 280, a linkage mechanism comprising two linkage arms 298, 299, an adjustable brake mechanism 297 and two extension springs (not shown). The extension springs are configured to have a strength capable of retaining the linkage mechanism in an extended position, thereby counteracting weight of the linkage mechanism. The adjustable brake mechanism 297 is configured, such that, at a scanning height $E_s$, the linkage mechanism locks, actuates, and pulls the interlock arm 295 downward to release the bed 20 in relation to the table T.

Referring to FIG. 20B, this diagram illustrates, in a cutaway side view, the medical transporter 100, as shown in FIG. 20A, wherein, when the bed 20 is disposed below the scanning height $E_s$, the interlock arm 295 engages with a stopper block 296 to prohibit extending the bed 20 in relation to the table T, wherein a linkage arm 298 actuates the interlock arm 295, thereby retracting the interlock arm 295 to its original position, and thereby prohibiting extending the bed 20 in relation to the table T, in accordance with an embodiment of the present disclosure. The linkage mechanism is configured to dispose the linkage arm 298 in relation to the linkage arm 299 at an angle β and to naturally collapse when the bed 20 is lowered below the scanning height $E_s$, e.g., when lowering the table T in relation to the base B is desired, wherein a lowering motion triggers applying a force to push the interlock arm 295 upwards into an engaged state. By default, at any height lower that the scanning height $E_s$, the extension springs are configured to retract to their original length, and thus, hold the linkage mechanism in an extended position; and the interlock arm 295 is then pushed up to its original retracted position. The linkage arms 298, 299 will pull the interlock arm 295 down only when the table T, effectively, the bed 20, is disposed at an elevation $E_2$ that is compatible with (approximating, but not necessarily exactly equal to, depending on patent factors, e.g., weight, shape, orientation, etc.) the scanning height $E_s$ of the imaging apparatus I.

Figure 21A:
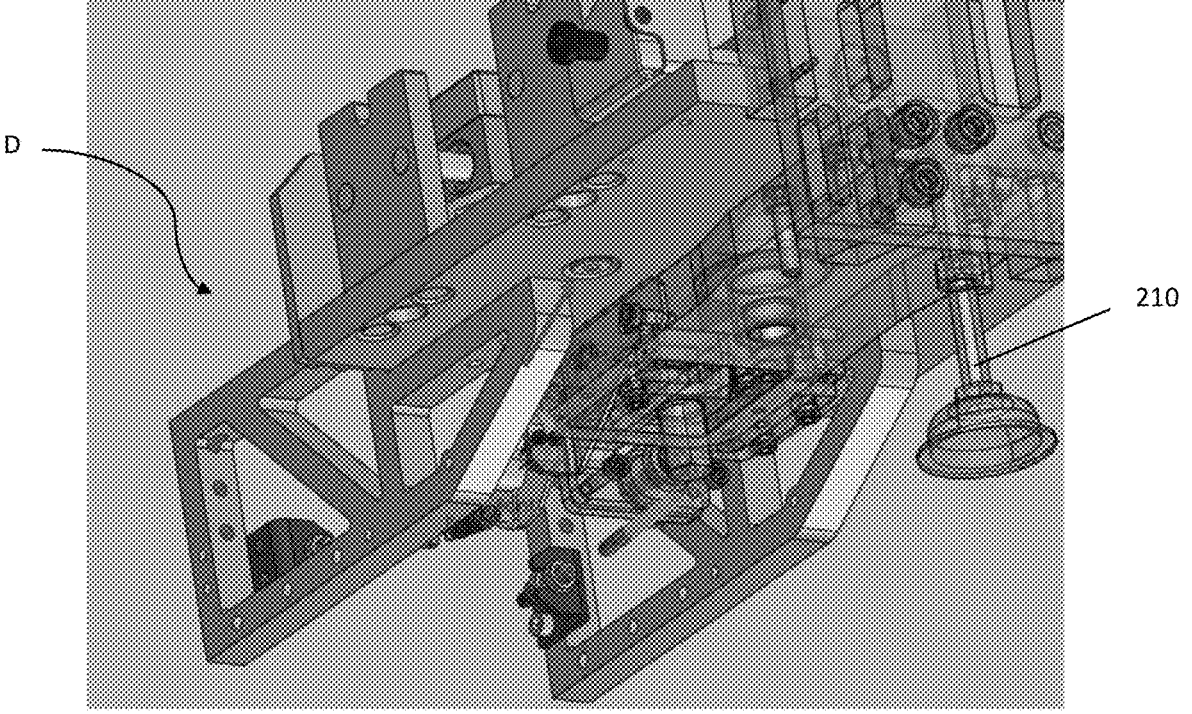
FIG. 21A is a diagram illustrating a cutaway perspective view of a docking module further comprising a secondary undock feature configured to permit manually undocking the transporter from medical equipment, in accordance with an embodiment of the present disclosure.

Referring to FIG. 21A, this diagram illustrates, in a cutaway perspective view, a docking module D further comprising a secondary undock feature 210, such as a set screw, e.g., a shoulder screw, by example only, configured to permit manually undocking the transporter 100 from medical equipment, such as an imaging apparatus I, e.g., an MRI machine, in accordance with an embodiment of the present disclosure. The secondary undock feature 210 is configured to permit manually undocking the transporter 100 from the medical equipment, e.g., by service personnel. The secondary undock feature 210 can be used to undock the transporter 100 if the primary undock mechanism of the docking module D malfunctions. The secondary undock feature 210 is configured for activation by way of a hexagonal key, e.g., a 6-mm hex key, for example, to manually rotate a dock actuator linkage. According to FIG. 21A and FIG. 21C, the secondary undock is configured as an alternate way to actuate the lever that moves the docking elements.

Figure 21B:
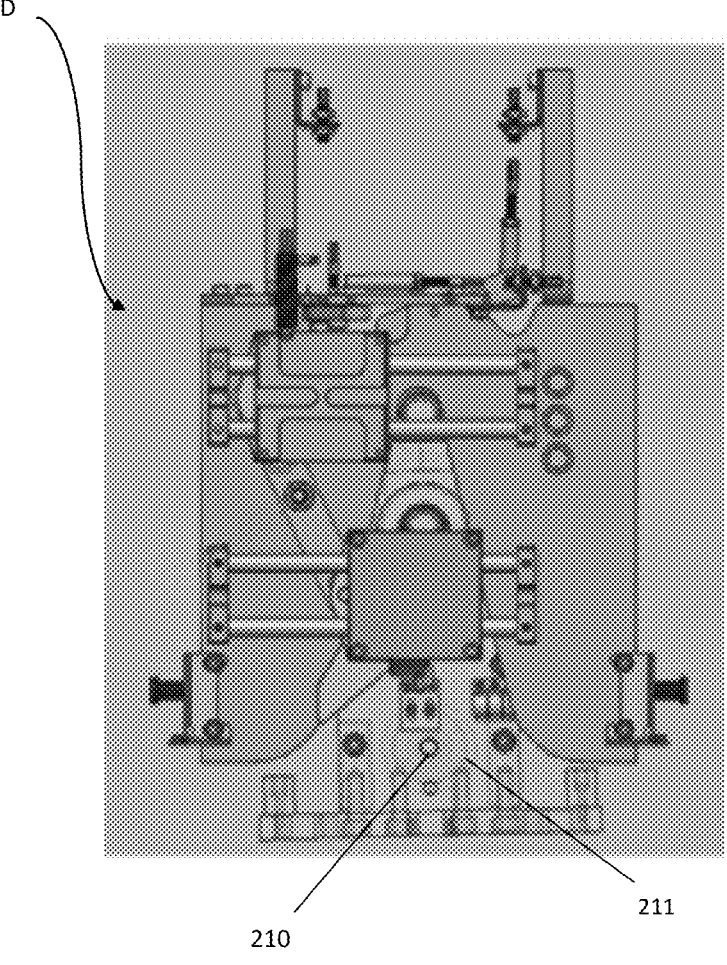
FIG. 21B is a diagram illustrating a top view of the docking module further comprising the secondary undock feature configured to permit manually undocking the transporter from medical equipment, as shown in FIG. 21A, in accordance with an embodiment of the present disclosure.

Referring to FIG. 21B, this diagram illustrates, in a top view, the docking module D further comprising the secondary undock feature 210, such as the set screw, e.g., the shoulder screw, configured to permit manually undocking the transporter 100 from medical equipment, such as an imaging apparatus I, e.g., an MRI machine, as shown in FIG. 21A, in accordance with an embodiment of the present disclosure. From the top of the docking module D, a distal end of the secondary undock feature 210 may be disposed through a plate 211.

Figure 21C:
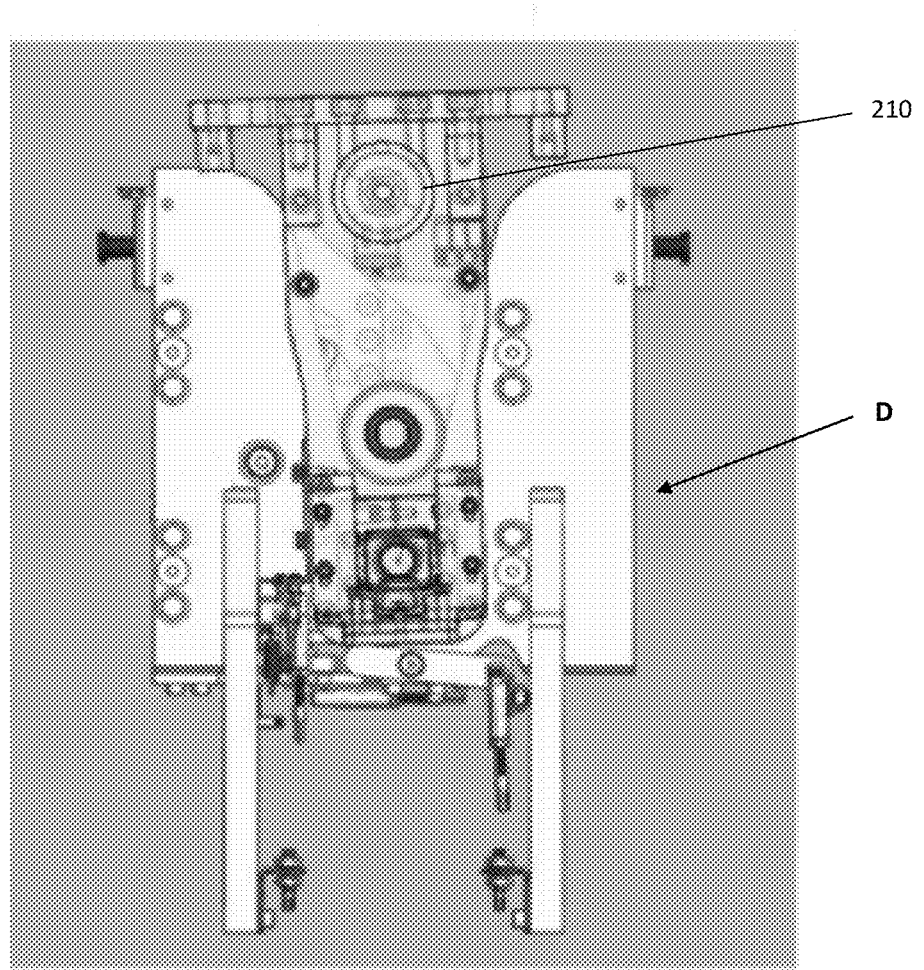
FIG. 21C is a diagram illustrating a bottom view of the docking module further comprising the secondary undock feature configured to permit manually undocking the transporter from medical equipment, as shown in FIG. 21A, in accordance with an embodiment of the present disclosure.

Referring to FIG. 21C, this diagram illustrates, in a bottom view, the docking module D further comprising the secondary undock feature 210, such as the set screw, e.g., the shoulder screw, configured to permit manually undocking the transporter 100 from medical equipment, such as an imaging apparatus I, e.g., an MRI machine, as shown in FIG. 21A, in accordance with an embodiment of the present disclosure. From the bottom of the docking module D, a proximal end (or head) of the secondary undock feature 210 is visibly exposed for ready use by service personnel.

Figure 22A:
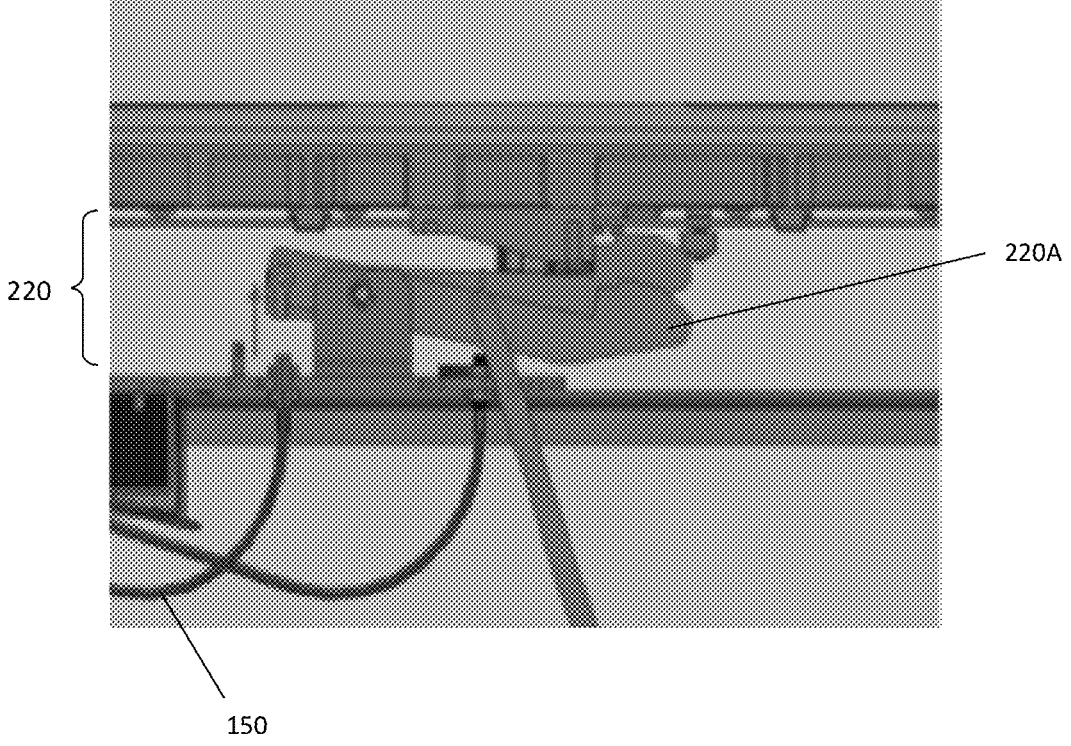
FIG. 22A is a diagram illustrating a cutaway side view of a height-bed interlock comprising a height-bed interlock arm, the height-bed interlock operable with a sensor of the docking module, the sensor configured to sense elevation of the bed, in accordance with an embodiment of the present disclosure.

Referring to FIG. 22A, this diagram illustrates, in a cutaway side view, a height-sensor interlock 220 comprising an interlock arm 220a, the height-sensor interlock 220 operable with a sensor 221 (shown in FIG. 22B) of the docking module D, the sensor 221 configured to sense elevation of the bed 20. When the bed 20 is disposed at the scanning height E, the cable 150 is pulled upward as the interlock arm 220a is pulled downward, in accordance with an embodiment of the present disclosure. The docking system, comprising the docking module D, is configured to report to a controller of the smart system when the transporter 100 is secured in relation to the imaging apparatus I and is disposed at an elevation $E_2$ that is compatible with the scanning height $E_s$ of the imaging apparatus I. This requirement covers both height alignment and proper docking engagement (docked and locked). By example only, the imaging apparatus I has two photo-interrupter sensors (not shown) that must both be tripped in order for the imaging apparatus I to recognize that the transporter 100 is at the proper elevation, docked, and locked. At scanning height, the height-sensor interlock arm 220a is downwardly pulled via the linkage system. The other end of the interlock arm 220a is coupled with a cable 150 that is upwardly pulled, whereby tension causes a sensor plate 222 of the sensor 221 that is disposed at the docking module D to rotate clockwise, thereby tripping the sensor 221 to indicate that the elevation $E_2$ is compatible with the scanning height $E_s$ (FIG. 22B).

Figure 22B:
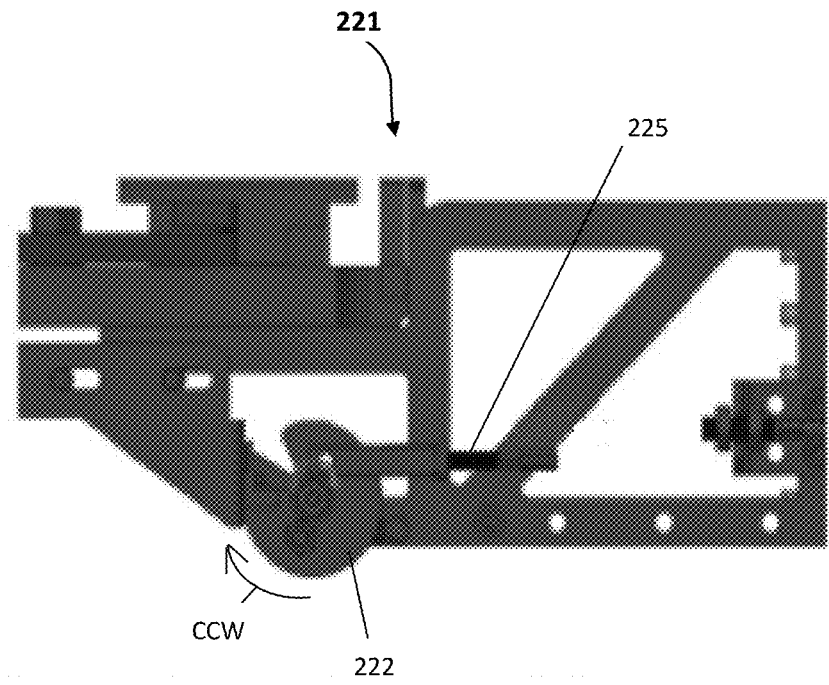
FIG. 22B is a diagram illustrating a detailed closeup side view of a sensor, operable with the height-bed interlock comprising the height-bed interlock arm, as shown in FIG. 22A, in accordance with an embodiment of the present disclosure.

Referring to FIG. 22B, this diagram illustrates, in a detailed closeup side view, a sensor 221, operable with the height-sensor interlock 220 comprising the height-bed interlock arm 220a, as shown in FIG. 22A, wherein the sensor 221 further comprises a sensor plate 222, a detector 223, and an indicator 224, wherein the sensor plate 222 is configured to rotate clockwise, such as in a direction CW, e.g., by way of a spring 225, wherein, when the sensor 221 is rotated clockwise, such as in a direction CW, the detector 223 is triggered to detect elevation of the bed 20 and to indicate when the elevation of the bed 20 is compatible with the scanning height $E_s$, in accordance with an embodiment of the present disclosure.

Figure 22C:
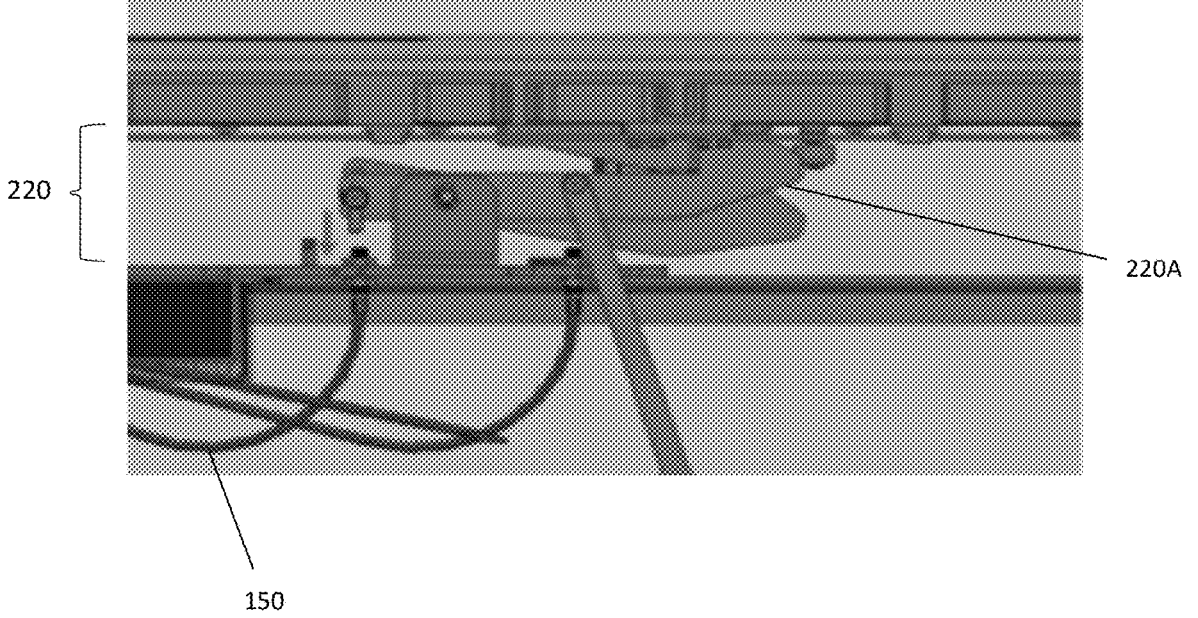
FIG. 22C is a diagram illustrating a cutaway side view of the height-bed interlock comprising the height-bed interlock arm, the height-bed interlock operable with a sensor of the docking module, the sensor configured to sense elevation of the bed, as shown in FIG. 22A, in accordance with an embodiment of the present disclosure.

Referring to FIG. 22C, this diagram illustrates, in a cutaway side view, the height-sensor interlock 220 comprising an interlock arm 220a, the height-sensor interlock 220 operable with a sensor 221 of the docking module D, the sensor 221 configured to sense elevation of the bed 20, as shown in FIG. 22A, wherein, when the bed 20 is disposed below the scanning height $E_s$, the cable 150 is pulled downward as the height-bed interlock arm 220 is pushed downward, in accordance with an embodiment of the present disclosure. Below the scanning height $E_s$, the height-bed interlock is pushed upward, thereby releasing the tension in the cable 150. The spring 225 that is coupled with the sensor plate 222 springs retracts to its original position, thereby causing the sensor plate 222 to rotate back counterclockwise, such as in a direction CCW, to its original state and to deactivate the photo-interrupter sensor.

Figure 22D:
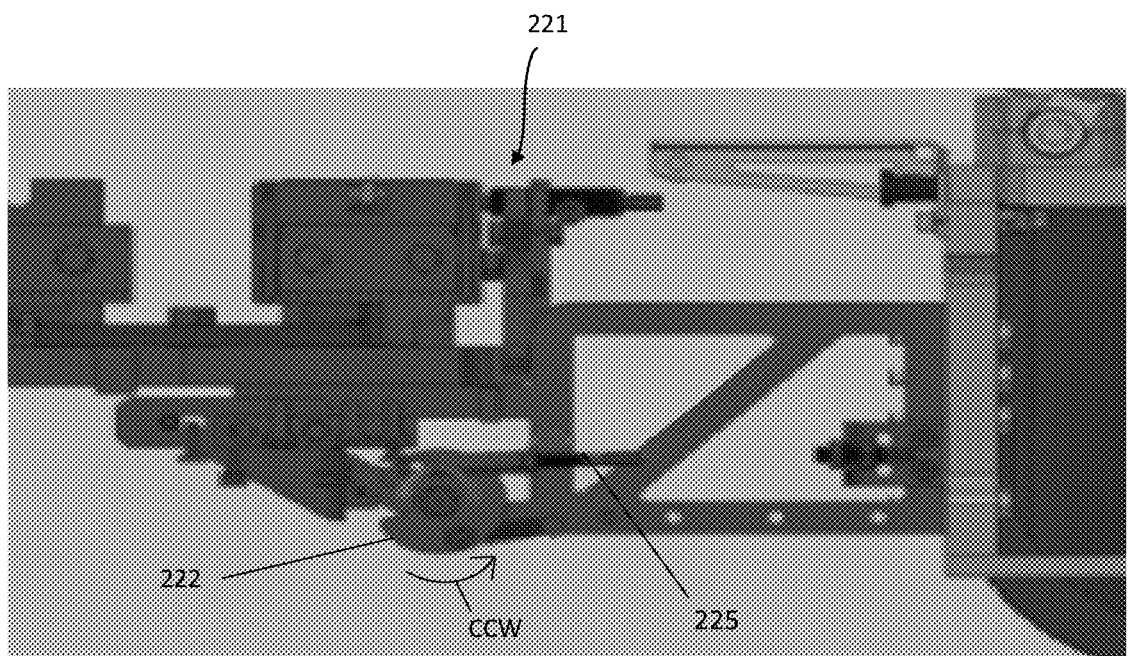
FIG. 22D is a diagram illustrating a detailed closeup side view of the sensor, operable with the height-bed interlock comprising the height-bed interlock arm, as shown in FIG. 22C, in accordance with an embodiment of the present disclosure.

Referring to FIG. 22D, this diagram illustrates, in a detailed closeup side view, the height-sensor interlock 220 comprising an interlock arm 220a, the height-sensor interlock 220 operable with a sensor 221 of the docking module D, the sensor 221 configured to sense elevation of the bed 20, as shown in FIG. 22C, wherein the sensor plate 222 is further configured to rotate counter-clockwise, such as in a direction CCW, e.g., by way of the spring 225, wherein, when the sensor plate 222 is rotated counter-clockwise, such as in a direction CCW, the detector 223 is triggered and detects the elevation of the bed 20 and the indicator 224 is triggered to indicate when the elevation of the bed 20 returns to an elevation below the scanning height $E_s$, in accordance with an embodiment of the present disclosure.

Figure 23:
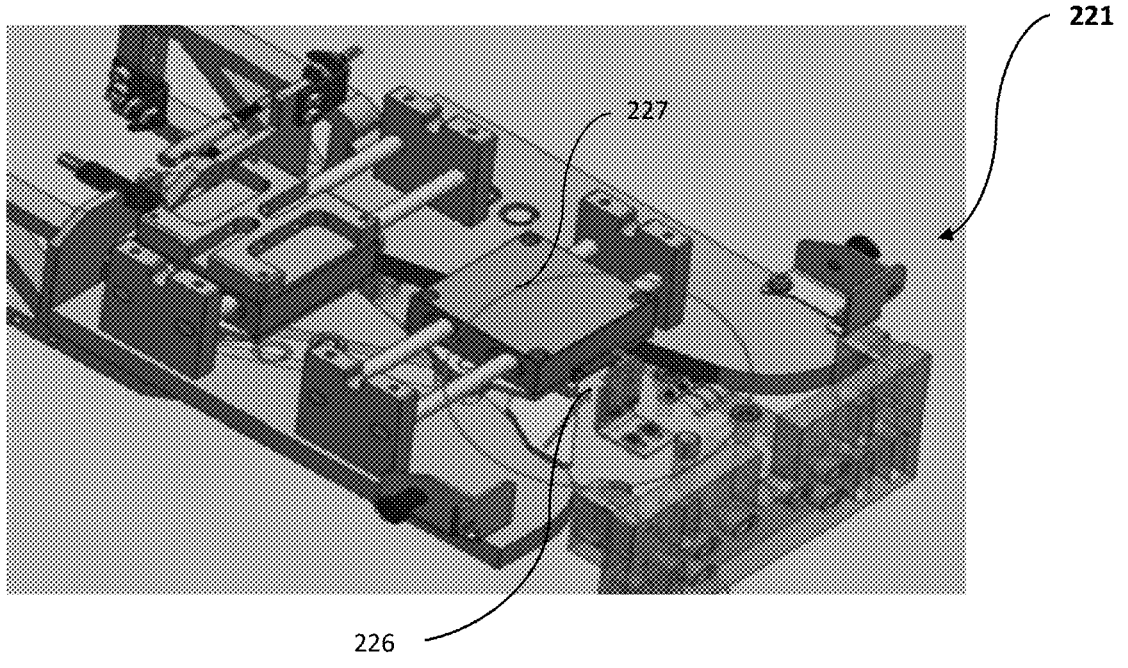
FIG. 23 is a diagram illustrating a perspective view of a sensor, comprising a bracket configured to move on a sliding block to trigger another sensor disposed on a scanner side dock, in accordance with an embodiment of the present disclosure.

Referring to FIG. 23, this diagram illustrates, in a perspective view, a sensor 221 of a docking module D, comprising a bracket 226 configured to move on a sliding block 227 to trigger another sensor (not shown) disposed on a scanner side dock, such as disposed in relation to a receiver portion R of the imaging apparatus I, to indicate that the transporter 100 is in a docked position, in accordance with an embodiment of the present disclosure. For example, the other sensor (on the imaging apparatus side) comprises a photo-interrupter sensor that is activated when the dock sliders (on the imaging apparatus side) move into the "docked" position. Signals from both sensors, e.g., the sensor 221 on the transporter 100 side and the other sensor on the imaging apparatus I side, are received by a controller or a processor of the smart system operable with the transporter 100. The signals are combined with an "AND" function only when both sensors are interrupted, whereby t the imaging apparatus I registers the transporter 100 as being "docked."

Figure 24A:
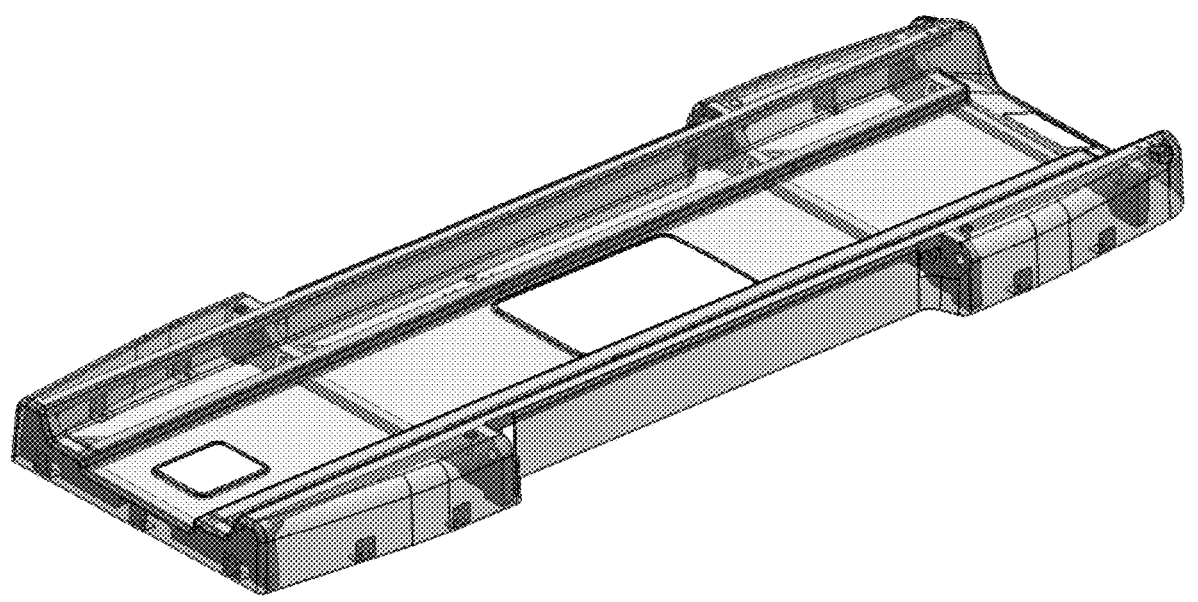
FIG. 24A is a diagram illustrating a perspective view of an upper enclosure of a transporter, in accordance with an embodiment of the present disclosure.

Referring to FIG. 24A, this diagram illustrates, in a perspective view, an upper enclosure 240 configured to accommodate an upper frame 245 (FIG. 24B) of the transporter 100, in accordance with an embodiment of the present disclosure. The upper enclosure 240 may be at least one of molded and bonded, such as being formed on a negative tool (not shown). The upper enclosure 240 is reconfigured to accommodate coupling of at least one handle H, at least one bumper (not shown), and at least one side-rail 22 with the upper frame 245.

Figure 24B:
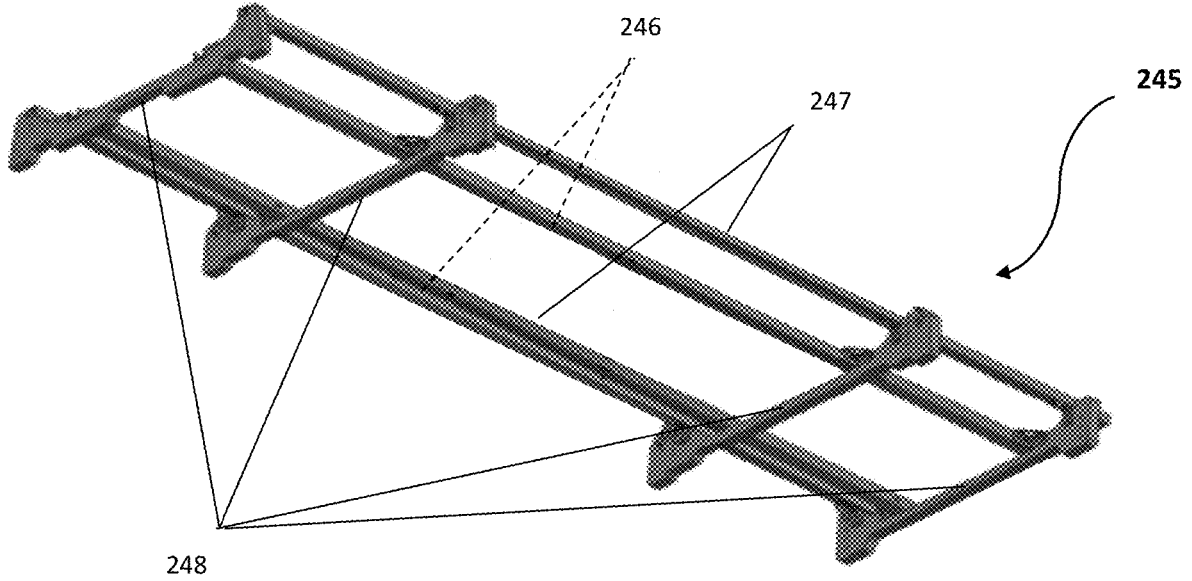
FIG. 24B is a diagram illustrating a perspective view of an upper frame of a transporter, in accordance with an embodiment of the present disclosure.

Referring to FIG. 24B, this diagram illustrates, in a perspective view, an upper frame 245 of a transporter 100, the upper frame 245 comprising a plurality of frame members, the plurality of frame members comprising a main frame member 246, auxiliary frame members 247, and ribs 248, in accordance with an embodiment of the present disclosure. The upper frame 245 may be fabricated, per-assembled, and then at least one of molded and bonded to the upper enclosure 240. The upper frame 245 is further configured to couple with at least one of: at least one handle H, at least one bumper 241, and at least one side-rail 22. The at least one handle H comprises at least one of a tubular reconfiguration and a bent configuration. The scale of the weighing mechanism 51, may be coupled with, or integrated with, the upper frame 245.

Figure 25:
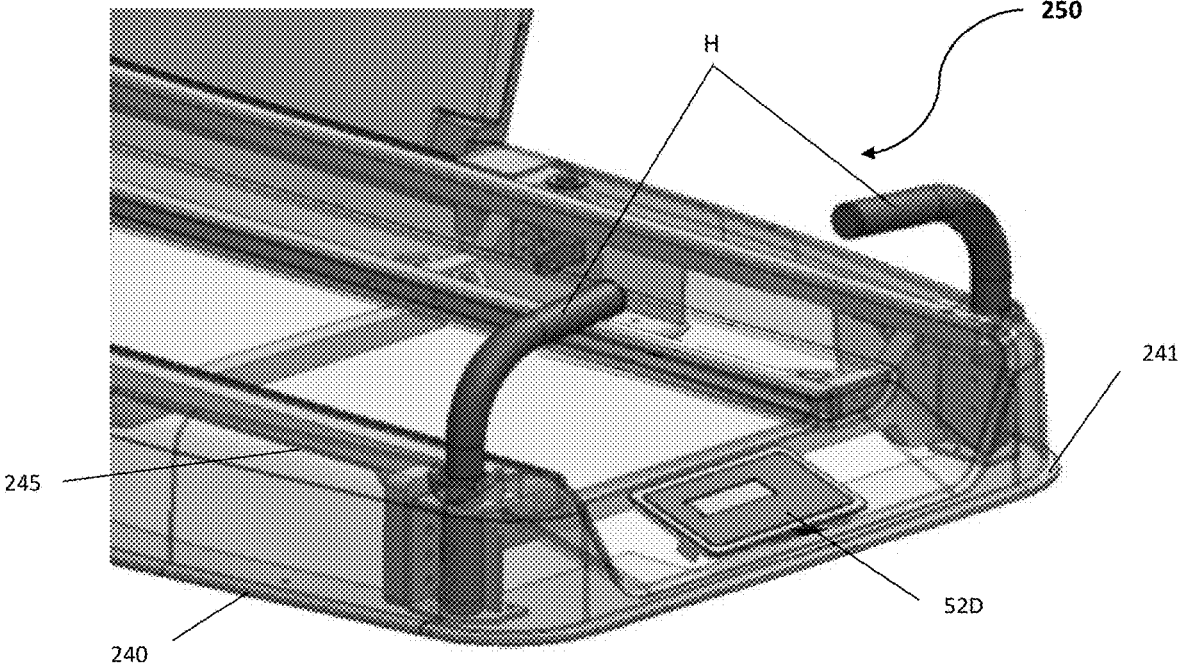
FIG. 25 is a diagram illustrating a cutaway perspective view of an upper assembly of a transporter, in accordance with an embodiment of the present disclosure.

Referring to FIG. 25, this diagram illustrates, in a cutaway perspective view, an upper assembly 250 of a transporter 100, in accordance with an embodiment of the present disclosure. The upper assembly 250 comprises the upper enclosure 240 (FIG. 24A) and the upper frame 245 (FIG. 24B). The upper assembly 250 is configured to couple with, and/or mount in relation to, a plurality of load cells, such as four load cells, of the weighing system of the smart system. The upper assembly 250 is further configured to accommodate a scale display 52D.

Figure 26:
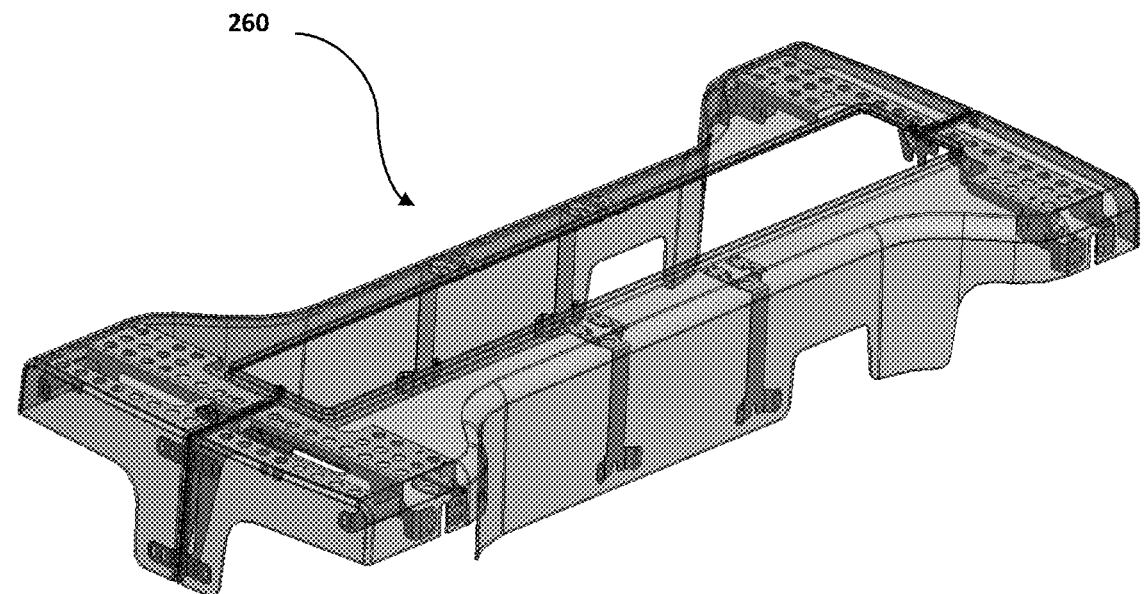
FIG. 26 is a diagram illustrating a perspective view of a skirt enclosure assembly of a transporter, in accordance with an embodiment of the present disclosure.

Referring to FIG. 26, this diagram illustrates, in a perspective view, a skirt enclosure 260 of a transporter 100, in accordance with an embodiment of the present disclosure. The skirt enclosure 260 may be molded, such as being formed on a positive tool (not shown). The skirt enclosure 260 is configured to be one of the components to be lastly installed and to be independently removable without significant disassembly during fabrication of the transporter 100.

Figure 27:
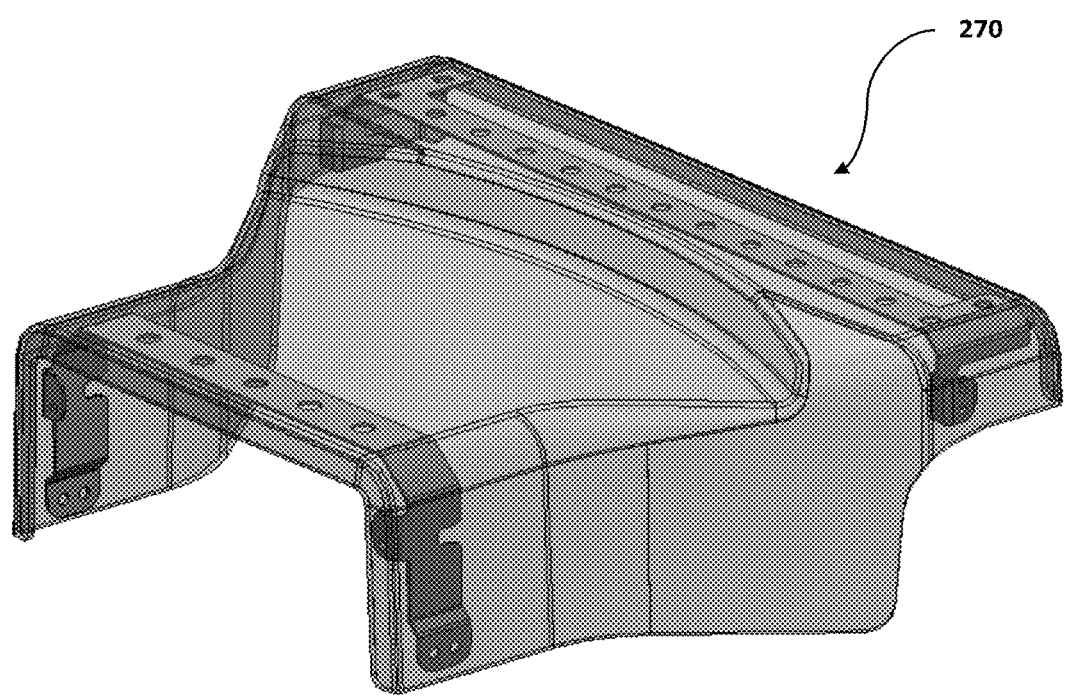
FIG. 27 is a diagram illustrating a perspective view of a dock enclosure of a transporter, in accordance with an embodiment of the present disclosure.

Referring to FIG. 27, this diagram illustrates, in a perspective view, a dock enclosure 270 of a transporter 100, in accordance with an embodiment of the present disclosure. The dock enclosure 270 may be molded, such as being formed on a positive tool (not shown). The dock enclosure 270 is configured to be one of the components to be lastly installed and to be independently removable without significant disassembly during fabrication of the transporter 100.

Figure 28A:
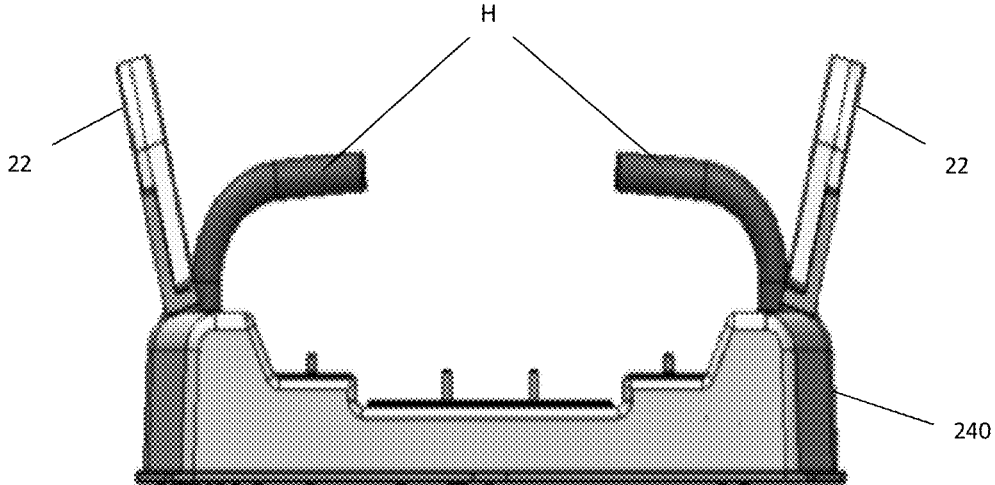
FIG. 28A is a diagram illustrating a front view of an upper assembly of a transporter, as shown in FIG. 25, comprising at least one side rail disposed in a first position, in accordance with an embodiment of the present disclosure.

Referring to FIG. 28A, this diagram illustrates, in a front view, an upper assembly 250 of a transporter 100, as shown in FIG. 25, the upper assembly 250 configured to accommodate at least one side-rail 22 in a first position, such as a deployed position, e.g., when the transporter 100 is in use when a patient P is loaded on the bed 20, in accordance with an embodiment of the present disclosure. By example only, the at least one side-rail 22 comprises a twin-sheet thermo-formed enclosure with machined hinges configured to facilitate rotation of the at least one side-rail 22. By example only, the at least one side-rail 22 further comprises at least one plunger, e.g., two spring-plungers (not shown) configured to simultaneously actuate via the at least one corresponding handle H, thereby locking the at least one side-rail 22 into one of the three positions: an undeployed position, an interim position, and a deployed position. The at least one side-rail 22 is configured to couple with the upper frame 245 as part of the upper frame sub-assembly. The at least one side-rail 22 is configured to be independently removable for easy servicing with minimal disassembly of other parts.

Figure 28B:
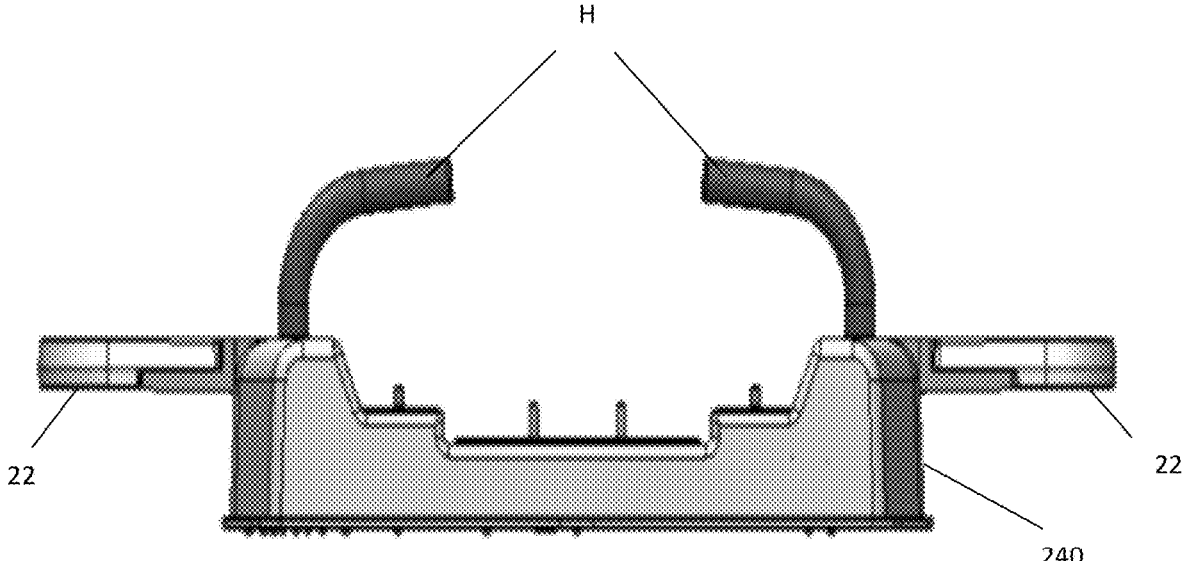
FIG. 28B is a diagram illustrating a front view of an upper assembly of a transporter, as shown in FIG. 25, comprising at least one side rail disposed in a second position, in accordance with an embodiment of the present disclosure.

Referring to FIG. 28B, this diagram illustrates, in a front view, the upper assembly 250 of a transporter 100, as shown in FIG. 25, the upper assembly 250 configured to accommodate at least one side-rail 22 in a second position, such as an interim position, e.g., when the transporter is in use while loading or offloading a patient P on the bed 20, in accordance with an embodiment of the present disclosure.

Figure 28C:
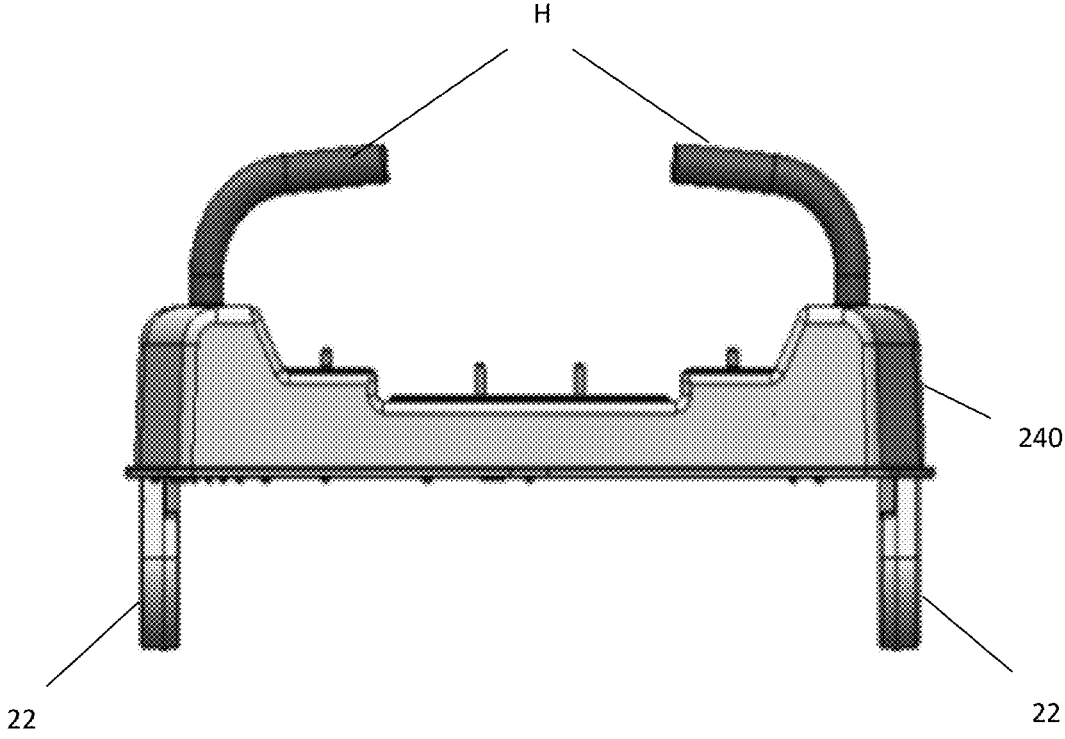
FIG. 28C is a diagram illustrating a front view of an upper assembly of a transporter, as shown in FIG. 25, comprising at least one side rail disposed in a third position, in accordance with an embodiment of the present disclosure.

Referring to FIG. 28C, this diagram illustrates, in a front view, the upper assembly 250 of a transporter 100, as shown in FIG. 25, the upper assembly 250 configured to accommodate at least one side-rail 22 in a third position, such as an undeployed position, e.g., when the transporter is not in use or prior to loading of a patient P on the bed 20, in accordance with an embodiment of the present disclosure.

Referring to FIG. 29, this flow diagram illustrates a method M1 of fabricating a medical transporter 190, in accordance with an embodiment of the present disclosure. The method M1 comprises: providing a frame 191, as indicated by block 2901; providing at least one side-rail 192 operably coupled with the frame 191, as indicated by block 2902; providing at least one lift member 192 operably coupled with the frame 191, as indicated by block 2903; providing at least one actuator 194 operably coupled with the at least one lift member 192, providing the at least one actuator 194 comprising configuring the at least one actuator 194 to adjust an elevation of the frame 191 by actuating the at least one lift member 193, as indicated by block 2904; providing a docking mechanism 195 operable with the frame 191 for facilitating docking of the frame 191 in relation to an imaging apparatus I, as indicated by block 2905; and providing a weighing mechanism 196, providing the weighing mechanism 196 comprising at least one of operably coupling the weighing mechanism 196 with the frame 191 and integrating the weighing mechanism 196 with the frame 191, as indicated by block 2906, whereby a patient P is weighable, and whereby elevation of the frame 191 is electronically adjustable.

Still referring to FIG. 29, in the method M1, at least one of: providing the frame 191, as indicated by block 2901, comprises providing at least one of aluminum, an aluminum alloy, and a composite material; and providing the frame 191, as indicated by block 2901, comprises configuring the frame 191 by using finite element modeling. The method M1 further comprises providing at least one enclosure 197 configured to accommodate the at least one lift member, as indicated by block 2907, wherein providing the at least one enclosure 197, as indicated by block 2907, comprises providing at least one of a polymer, a composite, an acrylonitrile butadiene styrene (ABS) polymer, a polycarbonate (PC) polymer, and a thermo-formed ABS-PC polymer composite. The method M1 further comprises providing a plurality of casters 198 operably coupled with the frame 191, as indicated by block 2908, wherein providing the plurality of casters 198 comprises disposing at least one caster 198 of the plurality of casters 198 in relation to a center-line of the frame 191 and configuring the at least one caster 198 to facilitate steering of the frame 191.

Still referring to FIG. 29, in the method M1, providing the at least one actuator 194, as indicated by block 2904, comprises providing the at least one actuator 194 being powered by an electrical power supply (not shown). Providing the at least one actuator 194, as indicated by block 2904, comprises providing the at least one actuator 194 being powered by an electrical power supply comprising at least one of a battery, a rechargeable battery, and a removable rechargeable battery. Providing the at least one side-rail 192, as indicated by block 2902, comprises providing at least one of a polymer, a composite, an acrylonitrile butadiene styrene (ABS) polymer, a polycarbonate (PC) polymer, and a thermo-formed ABS-PC polymer composite. Providing the at least one side-rail, as indicated by block 2902, further comprises providing at least one latch 199 configured to register, secure, and release the at least one side-rail 192 in relation to the frame 191. Providing the docking mechanism 195, as indicated by block 2905, comprises optimizing the docking mechanism 195 for Design for Manufacturing (DFM), whereby energy transfer is optimized, and whereby a force required to dock the frame 191 is minimized.

Referring to FIG. 30, this flow diagram illustrates a method M2 of weighing a patient P and automatically adjusting elevation of a frame 191 by way of a medical transporter 190, in accordance with an embodiment of the present disclosure. The method M2 comprises: providing a medical transporter 190, as indicated by block 3000, providing the medical transporter 190 comprising: providing a frame 191, as indicated by block 3001; providing at least one side-rail 192 operably coupled with the frame 191, as indicated by block 3002; providing at least one lift member 192 operably coupled with the frame 191, as indicated by block 3003; providing at least one actuator 194 operably coupled with the at least one lift member 192, providing the at least one actuator 194 comprising configuring the at least one actuator 194 to adjust an elevation of the frame 191 by actuating the at least one lift member 193, as indicated by block 2104; providing a docking mechanism 195 operable with the frame 191 for facilitating docking of the frame 191 in relation to an imaging apparatus I, as indicated by block 3005; and providing a weighing mechanism 196, providing the weighing mechanism 196 comprising at least one of operably coupling the weighing mechanism 196 with the frame 191 and integrating the weighing mechanism 196 with the frame 191, as indicated by block 3006, whereby a patient P is weighable, and whereby elevation of the frame 191 is electronically adjustable; and activating the medical transporter, as indicated by block 2109, thereby weighing the patient P, and thereby electronically adjusting elevation of the frame 191.

Still referring to FIG. 30, in the method M4, at least one of: providing the frame 191, as indicated by block 2101, comprises providing at least one of aluminum, an aluminum alloy, and a composite material; and providing the frame 191, as indicated by block 3001, comprises configuring the frame 191 by using finite element modeling. The method M3 further comprises providing at least one enclosure 197 configured to accommodate the at least one lift member, as indicated by block 3007, wherein providing the at least one enclosure 197, as indicated by block 3007, comprises providing at least one of a polymer, a composite, an acrylonitrile butadiene styrene (ABS) polymer, a polycarbonate (PC) polymer, and a thermo-formed ABS-PC polymer composite. The method M2 further comprises providing a plurality of casters 198 operably coupled with the frame 191, as indicated by block 3008, wherein providing the plurality of casters 198 comprises disposing at least one caster 198 of the plurality of casters 198 in relation to a center-line of the frame 191 and configuring the at least one caster 198 to facilitate steering of the frame 191.

Still referring to FIG. 30, in the method M2, providing the at least one actuator 194, as indicated by block 3004, comprises providing the at least one actuator 194 being powered by an electrical power supply (not shown). Providing the at least one actuator 194, as indicated by block 3004, comprises providing the at least one actuator 194 being powered by an electrical power supply comprising at least one of a battery, a rechargeable battery, and a removable rechargeable battery. Providing the at least one side-rail 192, as indicated by block 3002, comprises providing at least one of a polymer, a composite, an acrylonitrile butadiene styrene (ABS) polymer, a polycarbonate (PC) polymer, and a thermo-formed ABS-PC polymer composite.

Providing the at least one side-rail, as indicated by block 3002, further comprises providing at least one latch 199 configured to register, secure, and release the at least one side-rail 192 in relation to the frame 191. Providing the docking mechanism 195, as indicated by block 3005, comprises optimizing the docking mechanism 195 for design for manufacturing (DFM), whereby energy transfer is optimized, and whereby a force required to dock the frame 191 is minimized.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

What is claimed:
1. A medical transporter apparatus, comprising:
a frame;
at least one side-rail operably coupled with the frame;
at least one lift member operably coupled with the frame;
at least one actuator operably coupled with the at least one lift member, the at least one actuator configured to adjust an elevation of the frame by actuating the at least one lift member;
a docking mechanism operable with the frame for facilitating docking of the frame in relation to an imaging apparatus; and
a weighing mechanism, the weighing mechanism being at least one of operably coupled with the frame and integrated with the frame; and
a controller in communication with the weighing mechanism and the actuator;
wherein the controller is configured to:
receive weight data from the weighing mechanism;
determine whether the apparatus satisfies a set of interlocks comprising a dock-bed interlock, a bed-dock interlock, a height-bed interlock, a bed-height interlock, and a dock-latch interlock; and
while the interlocks are satisfied, dynamically control the actuator based on the weight data to adjust the elevation of the frame.

2. The apparatus of claim 1, wherein the weighing mechanism comprises a plurality of load cells disposed proximate corners of a table of the apparatus.

3. The apparatus of claim 1, wherein the interlocks comprise a height-sensor interlock including a flag configured to interrupt a photo-interrupter sensor disposed on a scanner-side dock when the frame is at a scanning height.

4. The apparatus of claim 1, further comprising
a bed switch configured such that the actuator is enabled only when a bed is fully retracted.

5. The apparatus of claim 4, wherein the weighing mechanism is deactivated when the bed is extended and retains a tare value through deactivation.

6. The apparatus of claim 1, wherein the docking mechanism is user-actuated by dock and undock foot pedals.

7. The apparatus of claim 1, wherein the frame is supported by casters including a centrally-mounted directionally-locking caster for steering, switchable by foot pedals.

8. The apparatus of claim 1, wherein the at least one actuator is powered by an electrical power supply, the electrical power supply comprises at least one of a battery, a rechargeable battery, and a removable rechargeable battery.

9. The apparatus of claim 1, further comprising an emergency release configured to unlatch the bed from a patient positioner to permit manual removal.

10. The apparatus of claim 1, wherein the at least one enclosure configured to accommodate the lift member comprises at least one of a polymer, a composite, an acrylonitrile butadiene styrene (ABS) polymer, a polycarbonate (PC) polymer, and a thermo-formed ABS-PC polymer composite.

11. The apparatus of claim 1, wherein the at least one side-rail further comprises at least one latch configured to register, secure, and release the at least one side-rail in relation to the frame.

12. The apparatus of claim 1, wherein the the apparatus is powered by at least one removable rechargeable battery for the lift and scale subsystems.

13. A method of operating a medical transporter apparatus, comprising the steps of:
providing a medical transporter apparatus, the medical transporter apparatus comprising:
a frame;
an actuator;
a docking mechanism;
a weighing mechanism; and
a controller;
docking the medical transporter apparatus to an imaging apparatus;
receiving, at the controller, weight data from the weighing mechanism;
evaluating, at the controller, whether a set of interlocks comprising at least a dock-bed interlock, a bed-dock interlock, a height-bed interlock, a bed-height interlock, and a dock-latch interlock are satisfied, including interrupting a photo-interrupter sensor on a scanner-side dock at the scanning height; and
while the interlocks are satisfied, dynamically adjusting an elevation of the frame by actuating the at least one actuator based on the weight data.

* * * * *